US009556434B2

(12) United States Patent
Hastings

(10) Patent No.: US 9,556,434 B2
(45) Date of Patent: Jan. 31, 2017

(54) ANTISENSE OLIGONUCLEOTIDES THAT TARGET A CRYPTIC SPLICE SITE IN USH1C AS A THERAPEUTIC FOR USHER SYNDROME

(71) Applicant: ROSALIND FRANKLIN UNIVERSITY OF MEDICINE AND SCIENCE, North Chicago, IL (US)

(72) Inventor: Michelle L Hastings, Lake Bluff, IL (US)

(73) Assignee: Rosalind Franklin University of Medicine and Science, North Chicago, IL (US)

( * ) Notice: Subject to any disclaimer, the term of this patent is extended or adjusted under 35 U.S.C. 154(b) by 0 days.

(21) Appl. No.: 14/705,579

(22) Filed: May 6, 2015

(65) Prior Publication Data

US 2015/0315590 A1 Nov. 5, 2015

Related U.S. Application Data

(63) Continuation of application No. 14/176,722, filed on Feb. 10, 2014, now abandoned, which is a continuation of application No. 13/461,565, filed on May 1, 2012, now Pat. No. 8,648,053, which is a continuation-in-part of application No. 13/277,975, filed on Oct. 20, 2011, now abandoned.

(60) Provisional application No. 61/481,613, filed on May 2, 2011, provisional application No. 61/394,973, filed on Oct. 20, 2010.

(51) Int. Cl.
| | | |
|---|---|---|
| C07H 21/04 | (2006.01) | |
| C12N 15/113 | (2010.01) | |
| A61K 31/712 | (2006.01) | |
| A61K 31/7115 | (2006.01) | |
| A61K 31/7125 | (2006.01) | |

(52) U.S. Cl.
CPC ........... *C12N 15/113* (2013.01); *A61K 31/712* (2013.01); *A61K 31/7115* (2013.01); *A61K 31/7125* (2013.01); *C12N 2310/11* (2013.01); *C12N 2320/33* (2013.01)

(58) Field of Classification Search
None
See application file for complete search history.

(56) References Cited

U.S. PATENT DOCUMENTS

| | | |
|---|---|---|
| 3,687,808 A | 8/1972 | Merigan et al. |
| 4,845,205 A | 7/1989 | Huynh Dinh et al. |
| 5,034,506 A | 7/1991 | Summerton et al. |
| 5,130,302 A | 7/1992 | Spielvogel et al. |
| 5,134,066 A | 7/1992 | Rogers et al. |
| 5,166,315 A | 11/1992 | Summerton et al. |
| 5,175,273 A | 12/1992 | Bischofberger et al. |
| 5,185,444 A | 2/1993 | Summerton et al. |
| 5,367,066 A | 11/1994 | Urdea et al. |
| 5,432,272 A | 7/1995 | Benner |
| 5,457,187 A | 10/1995 | Gmeiner et al. |
| 5,459,255 A | 10/1995 | Cook et al. |
| 5,484,908 A | 1/1996 | Froehler et al. |
| 5,502,177 A | 3/1996 | Matteucci et al. |
| 5,525,711 A | 6/1996 | Hawkins et al. |
| 5,552,540 A | 9/1996 | Haralambidis |
| 5,587,469 A | 12/1996 | Cook et al. |
| 5,594,121 A | 1/1997 | Froehler et al. |
| 5,596,091 A | 1/1997 | Switzer |
| 5,614,617 A | 3/1997 | Cook et al. |
| 5,645,985 A | 7/1997 | Froehler et al. |
| 5,681,941 A | 10/1997 | Cook et al. |
| 5,698,685 A | 12/1997 | Summerton et al. |
| 5,750,692 A | 5/1998 | Cook et al. |
| 5,763,588 A | 6/1998 | Matteucci et al. |
| 5,830,653 A | 11/1998 | Froehler et al. |
| 6,005,096 A | 12/1999 | Matteucci et al. |
| 6,268,490 B1 | 7/2001 | Imanishi et al. |
| 6,444,465 B1 | 9/2002 | Wyatt et al. |
| 6,525,191 B1 | 2/2003 | Ramasamy |
| 6,670,461 B1 | 12/2003 | Nielsen et al. |
| 6,770,748 B2 | 8/2004 | Imanishi et al. |
| 6,794,499 B2 | 9/2004 | Wengel et al. |
| 7,034,133 B2 | 4/2006 | Wengel et al. |
| 7,053,207 B2 | 5/2006 | Wengel |
| 7,399,845 B2 | 7/2008 | Seth et al. |
| 7,427,672 B2 | 9/2008 | Imanishi et al. |
| 7,741,457 B2 | 6/2010 | Swayze et al. |

(Continued)

FOREIGN PATENT DOCUMENTS

| | | |
|---|---|---|
| WO | WO 99/14226 | 3/1999 |
| WO | WO 2004/106356 | 12/2004 |

(Continued)

OTHER PUBLICATIONS

Baux et al. (Human Mutation Mutation in Brief #1012, 29:E76-E87, 2008).*
Albaek et al., "Analogues of a Locked Nucleic Acid with Three-Carbon 2',4'-Linkages: Synthesis by Ring-Closing Metathesis and Influence of Nucleic Acid Duplex Stability" J. Org. Chem. (2006) 71:7731-7740.
Ayuso et al., "Retinitis pigmentosa and allied conditions today: a paradigm of translational research" Genome Med. (2010) 2(5):34.
Braasch et al., "Novel Antisense and Peptide Nucleic Acid Strategies for Controlling Gene Expression" Biochemistry (2002) 41(14): 4503-4510.
Braasch et al., "Locked nucleic acid (LNA): fine-tuning the recognition of DNA and RNA" Chem. Biol. (2001) 8:1-7.

(Continued)

*Primary Examiner* — Kimberly Chong
(74) *Attorney, Agent, or Firm* — McDonnell Boehnen Hulbert & Berghoff LLP

(57) ABSTRACT

The present invention provides a method for treating Usher's syndrome in a human subject including administering to the human subject an oligonucleotide having 8 to 30 linked nucleosides having a nucleobase sequence comprising a complementary region comprising at least 8 contiguous nucleobases complementary to a target region of equal length within exon 3 of an Usher RNA transcript.

15 Claims, 16 Drawing Sheets

(56) References Cited

U.S. PATENT DOCUMENTS

| | | | |
|---|---|---|---|
| 8,501,805 B2 | 8/2013 | Seth et al. | |
| 8,530,640 B2 | 9/2013 | Seth et al. | |
| 8,546,556 B2 | 10/2013 | Seth et al. | |
| 8,648,053 B2 | 2/2014 | Hastings | |
| 2004/0171570 A1 | 9/2004 | Allerson et al. | |
| 2004/0241651 A1* | 12/2004 | Olek | C07K 14/4703 435/6.16 |
| 2005/0009771 A1 | 1/2005 | Levanon et al. | |
| 2005/0130923 A1 | 6/2005 | Bhat et al. | |
| 2006/0003953 A1* | 1/2006 | Bennett | C07H 21/04 514/44 A |
| 2007/0287831 A1 | 12/2007 | Seth et al. | |
| 2008/0039618 A1 | 2/2008 | Allerson et al. | |
| 2008/0194503 A1 | 8/2008 | Monia et al. | |
| 2009/0088721 A1 | 4/2009 | de Bizemont et al. | |
| 2009/0163435 A1 | 6/2009 | Bader et al. | |
| 2010/0190841 A1 | 7/2010 | Farrar et al. | |
| 2010/0203076 A1 | 8/2010 | Fotin-Mleczek et al. | |
| 2011/0021605 A1 | 1/2011 | Schulte et al. | |
| 2012/0149757 A1 | 6/2012 | Krainer et al. | |
| 2014/0114057 A1 | 4/2014 | Hastings et al. | |

FOREIGN PATENT DOCUMENTS

| | | |
|---|---|---|
| WO | WO 2005/021570 | 3/2005 |
| WO | WO 2007/134181 | 11/2007 |
| WO | WO 2008/049085 | 4/2008 |
| WO | WO 2008/101157 | 8/2008 |
| WO | WO 2008/150729 | 12/2008 |
| WO | WO 2008/154401 | 12/2008 |
| WO | WO 2009/006478 | 1/2009 |
| WO | 2012/151324 A1 | 11/2012 |
| WO | WO 2012/151324 | 11/2012 |

OTHER PUBLICATIONS

Crooke et al., "Pharmacokinetic Properties of Several Novel Oligonucleotide Analogs in mice" J. Pharmacol. Exp. Ther. (1996) 277(2):923-937.

Elayadi et al., "Application of PNA and LNA oligomers to chemotherapy" Curr. Opinion Invens. Drugs (2001) 2:558-561.

Englisch et al., "Chemically Modified Oligonucleotides as Probes and Inhibitors" Agnew Chem. Int. Ed. Engl. (1991) 30:613-629.

Freier et al., "The ups and downs of nucleic acid duplex stability: structure-stability studies on chemically-modified DNA:RNA duplexes" Nucleic Acids Research (1997) 25(22):4429-4443.

Frieden et al., "Expanding the design horizon of antisense oligonucleotides with alpha-L-LNA" Nucleic Acids Research (2003) 31(21):6365-6372.

Gibbs et al., "Function of MYO7A in the Human RPE and the Validity of Shaker1 Mice as a Model for Usher Syndrome 1B" Investigative Ophthalmology & Visual Science (2010) 51(2):1130-1135.

Goldmann et al. "Beneficial read-through of a USH1C nonsense mutation by designed aminoglycoside NB30 in the retina." Invest Ophthalmol Vis Sci. (2010) 51(12):6671-6680.

Jodelka et al., "Antisense oligonucleotide correction of splicing in a mouse model of Usher 1-5 syndrome." 2010 Rustbelt RNA Meeting. RRM, retrieved from the Internet Jan. 29, 2014: <http://www.rustbeltrna.org/2010/talks.php?all>]; Abstract.

Kabanov et al., "A new class of antivirals: antisense oligonucleotides combined with a hydrophobic substituent effectively inhibit influenza virus reproduction and synthesis of virus-specific proteins in MDCK cells" FEBS Lett. (1990) 259:327.

Koshkin et al., "LNA (locked nucleic acids): Synthesis of the adenine, cytosine, guanine, 5-methylcytosine, thymine and uracil bicyclonucleoside monomers, oligomerisation, and unprecedented nucleic acid recognition" Tetrahedron (1998) 54:3607-3630.

Kroschwitz, "Polynucleotides" Concise Encyclopedia of Polymer Science and Engineering (1990) John Wiley & Sons, NY pp. 858-859.

Kumar et al., "The first analogues of LNA (locked nucleic acids): phosphorothioate-LNA and 2'-thio-LNA" Bioorg Med Chem Lett. (1998) 8:2219-2222.

Lentz et al., "Ush1c216A knock-in mouse survives Katrina." Mutat Res. (2007) 616(1-2):139-144.

Letsinger et al., "Cholestexyl-conjugated oligonucleotides: Synthesis, properties, and activity as inhibitors of replication of human immunodeficiency virus in cell culture" PNAS (1989) 86:6553-6556.

Leumann et al., "DNA Analogues: From Supramolecular Principles to Biological Properties" Bioorganic & Medicinal Chemistry (2002) 10:841-854.

Lopez et al., "Mutational frequencies in usherin(USH2A gene) in 26 Colombian individuals with Usher syndrome type II" Biomedica. (2011) 31(1 ):82-90. [Article in Spanish].

Manoharan et al., "Chemical Modifications to Improve Uptake and Bioavailability of Antisense Oligonucleotides" Ann. N.Y. Acad. Sci. (1992) 660:306.

Manoharan et al., "Introduction of a Lipophilic Thioether Tether in the Minor Groove of Nucleic Acids for Antisense Applications" Bioorg. Med. Chem. Lett. (1993) 3(12):2765-2770.

Manoharan et al., "Cholic Acid-Oligonucleotide Conjugates for Antisense Applications" Bioorg. Med. Chem. Lett. (1994) 4:1053-1060.

Manoharan et al., "Oligonucleotide Conjugates: Alteration of the Pharmacokinetic Properties of Antisense Agents" Nucleosides & Nucleotides (1995) 14(3-5):969-973.

Manoharan et al., "Lipidic Nucleic Acids" Tetrahedron Lett. (1995) 36(21):3651-3654.

McCaffrey et al., "Blocking Cryptic Splicing in Usher syndrome using antisense oligonucleotides." The Association for Research in Vision and Opthalmology, Abstract, May 3, 2011, Ft. Lauderdale, FL.

Millan et al., "An Update on the Genetics of Usher Syndrome" Journal of Ophthalmology (2011), Article ID 417217, 1-8.

Mishra et al., "Improved leishmanicidal effect of phosphorotioate antisense oligonucleotides by LDL-mediated delivery" Biochim. Biophys. Acta (1995) 1264:229-237.

Oberhauser et al., "Effective incorporation of 2'-O-methyl-oligoribonucleotides into liposomes and enhanced cell association through modifications with thiocholesterol" Nucl. Acids Res. (1992) 20(3):533-538.

Orum et al., "Locked nucleic acids: A promising molecular family for gene-function analysis and antisense drug development" Curr. Opinion Mol. Ther. (2001) 3(3):239-243.

Saison-Behmoaras et al., "Short modified antisense oligonucleotides directed against Ha-ras point mutation induce selective cleavage of the mRNA and inhibit 124 cells proliferation" EMBO J. (1991) 10(5):1111-1118.

Sanghvi, Chapter 15, Antisense Research and Applications, Crooke and Lebleu ed., CRC Press (1993).

Shea et al., "Synthesis, hybridization properties and antiviral activity of lipid-oligodeoxynucleotide conjugates" Nucl. Acids Res. (1990) 18(13):3777-3783.

Singh et al., "LNA (locked nucleic acids): synthesis and high-affinity nucleic acid recognition" Chem. Commun. (1998) 455-456.

Singh et al., "Synthesis of 2'-amino-LNA: A novel conformationally restricted high-affinity oligonucleotide analogue with a handle" J. Org. Chem. (1998) 63: 10035-10039.

Srivastava et al., "Five- and Six-Membered Conformationally Locked 2',4'-Carbocyclic ribo-Thymidines: Thymidines: Synthesis, Structure, and Biochemical Studies" J. Am. Chem. Soc. (2007) 129(26):8362-8379.

Svinarchuk et al., "Inhibition of HIV proliferation in MT-4 cells by antisense oligonucleotide conjugated to lipophilic groups" Biochimie (1993) 75:49-54.

Vache et al., "Usher syndrome type 2 caused by activation of an USH2A pseudoexon: implications for diagnosis and therapy." Hum Mutat. (2012) 33(1):104-108.

Verpy et al., "A defect in harmonin, a PDZ domain-containing protein expressed in the inner ear sensory hair cells, underlies Usher syndrome type 1C" Nat. enet. (2000) 26(1):51-55.

(56) References Cited

OTHER PUBLICATIONS

Wahlestedt et al., "Potent and nontoxic antisense oligonucleotide containing locked nucleic acids" Proc. Natl. Acad. Sci. USA (2000) 97: 5633-5638.

Zhou et al., "Fine Tuning of Electrostatics around the Internucleotidic Phosphate through Incorporation of Modified 2',4'-Carbocyclic-LNAs and -ENAs Leads to Significant Modulation of Antisense Properties" J. Org. Chem. (2009) 74:118-134.

El-Amraoui, et al., "Usher I Syndrome: Unraveling the Mechanisms that Underlie the Cohesion of the Growing Hair Bundle in Inner Ear Sensory Cells", Journal of Cell Science, vol. 118, pp. 4593-4603, The Company of Biologists, 2005.

Hastings, et al., "Control of Pre-mRNA Splicing by the General Splicing Factors PUF60 and U2AF65", www.plosone.org, Issue 6, e538, Jun. 2007.

Kral, et al., "Profound Deafness in Childhood", The New England Journal of Medicine, vol. 365(15), pp. 1438-1450, Massachusetts Medical Society, Oct. 7, 2010.

Goemans, et al., "Systemic Administration of PRO051 in Duchenne's Muscular Dystrophy", New Engl J. of Med., vol. 364, pp. 1513-1522, NEJM.org, Apr. 21, 2011.

Lentz, et al., "Ush1 c216A Knock-in Mouse Survives Katrina", Mutation Research, vol. 616, pp. 139-144, sciencedirect.com, 2007.

Hastings, et al., "Tetracyclines That Promote SMN2 Exon 7 Splicing as Therapeutics for Spinal Muscular Atrophy", Sci. Transl Med. vol. 1, 5ra 12, stm.sciencemag.org, Nov. 4, 2009.

Verpy, et al., "A Defect in Harmonin, a PDZ Domain-containing Protein Expressed in the Inner Ear Sensory Hair Cells, Underlies Usher Syndrome Type 1C", Nature America Inc., http://genetics.nature.com, vol. 26, pp. 51-55, Sep. 2000.

Morton, et al., "New Hearing Screening—A Silent Revolution", Massachusetts Medical Society, N. Engl J. of Med., vol. 354, pp. 2151-2164, www.NEJM.org., May 18, 2006.

Hua et al., "Antisense Correction of SMN2 splicing in the CNS Rescues Necrosis in a Type III SMA Mouse Model", Genes Dev., vol. 24, pp. 1634-1644, Cold Spring Harbor Laboratory Press, Jul. 12, 2010.

\* cited by examiner

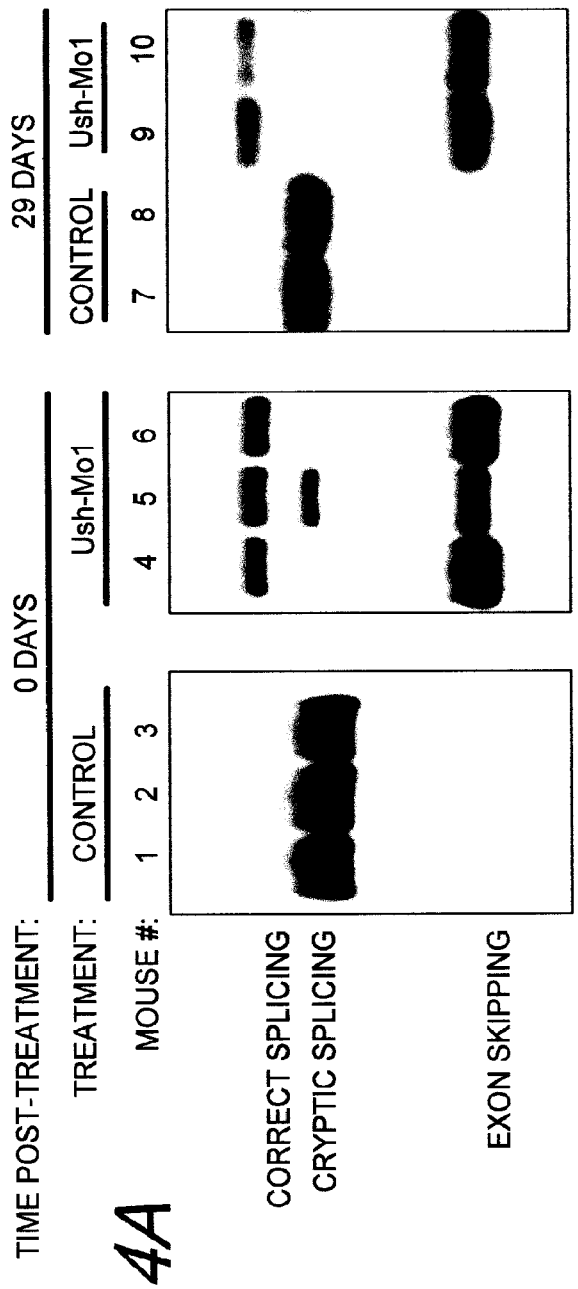
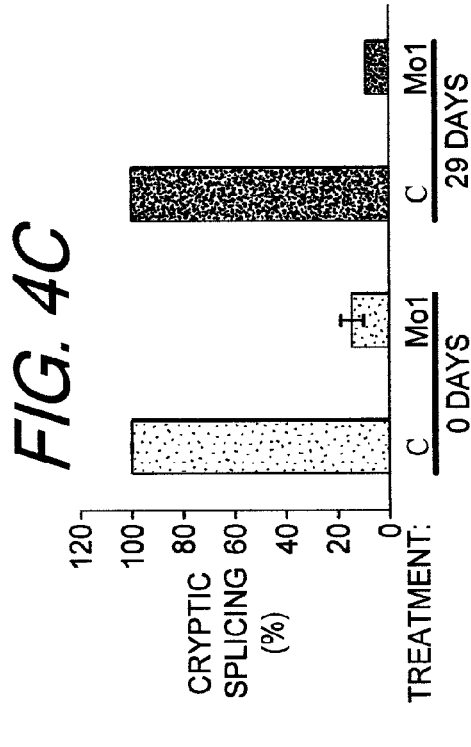
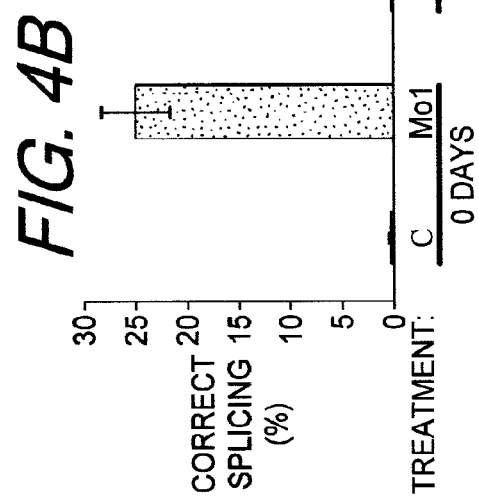
FIG. 4A
FIG. 4B
FIG. 4C

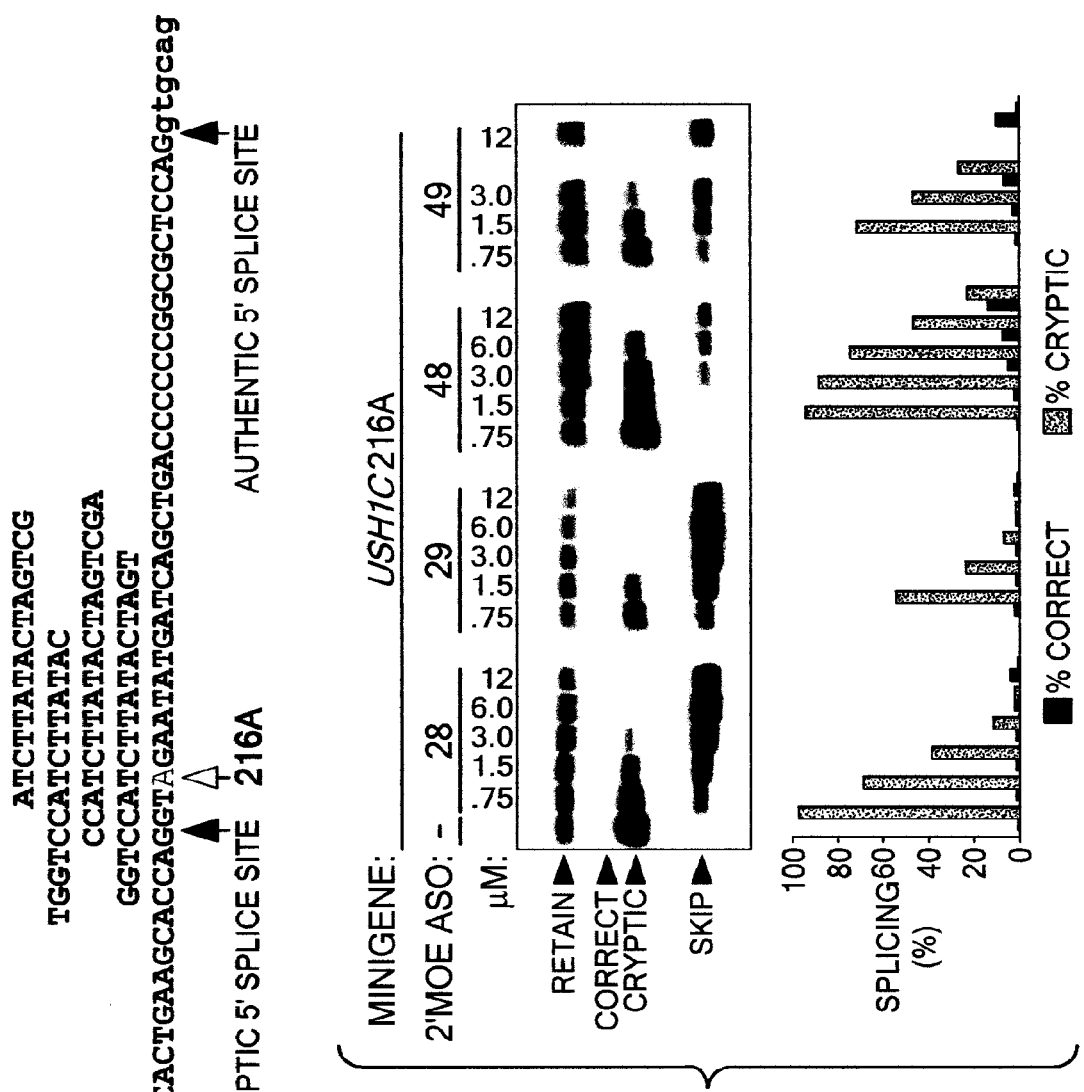

US 9,556,434 B2

ANTISENSE OLIGONUCLEOTIDES THAT TARGET A CRYPTIC SPLICE SITE IN USH1C AS A THERAPEUTIC FOR USHER SYNDROME

REFERENCE TO RELATED APPLICATIONS

This application is a continuation of U.S. patent application Ser. No. 14/176,722, filed Feb. 10, 2014 (abandoned), which is a continuation of U.S. patent application Ser. No. 13/461,565, filed May 1, 2012, now U.S. Pat. No. 8,648,053, which is a continuation in part of U.S. patent application Ser. No. 13/277,975, filed Oct. 20, 2011 (abandoned), which claims priority to U.S. Provisional Patent Application No. 61/394,973, filed Oct. 20, 2010, and U.S. Provisional Patent Application No. 61/481,613, filed May 2, 2011, and the disclosure of all are incorporated herein in their entirety by reference and made a part hereof.

SEQUENCE LISTING

The instant application contains a Sequence Listing which has been submitted in ASCII format via EFS-Web and is hereby incorporated by reference in its entirety. Said ASCII copy, created on Jan. 6, 2012, is named 11246115.txt and is 89,844 bytes in size.

FEDERALLY SPONSORED RESEARCH OR DEVELOPMENT

Not Applicable.

BACKGROUND OF THE INVENTION

Technical Field

The present invention provides a therapeutic treatment of Usher syndrome by administering to a person in need thereof an antisense oligonucleotide (ASO) that targets the RNA transcripts of the Ush1c gene to correct defective splicing associated with the disease. More particularly, certain ASOs 8-30 mer in size of the present invention base-pair with regions in exon 3 and intron 2 of the Ush1c gene to correct for loss of gene function due to mutations in the Ush 1c gene.

Background Art

Usher syndrome is the leading genetic cause of combined blindness and deafness. Usher syndrome is an autosomal recessive disorder characterized by hearing impairment and retinitis pigmentosa (for review, Keats and Corey, 1999). Usher syndrome is the most common genetic disease that involves both hearing and vision loss. Currently, there is no cure for this debilitating disease that affects approximately 4 in every 100,000 births. There are three types of Usher syndrome that are classified by disease severity. Usher syndrome type 1 (Usher I) is the most severe form and is characterized by severe hearing loss and vestibular dysfunction at birth. Ush1 individuals begin to develop vision problems in early adolescence that progress rapidly to complete blindness. There are five genes that have been associated with Usher I: Ush1C, MYO7A, CDH23, PCDH15 and SANS.

Gene therapy is an attractive approach for Usher syndrome treatment. All types of Usher syndrome appear to be inherited recessively and caused by loss of gene function, suggesting that correction of gene expression would be therapeutic. In addition, because of the early hearing loss, Usher syndrome patients could be treated therapeutically prior to retinal degeneration. Traditional gene therapy approaches based on gene delivery is problematic for many of the Usher genes as they are very large. Therapeutic approaches using small molecules that can directly alter gene expression are attractive possibilities that have been largely undeveloped for Usher syndrome. One reason for the lack of progress in the development of therapeutics for Usher syndrome has been the lack of mouse models that accurately represent the human disease. Prior art mouse models for the disease faithfully manifest the hearing and balance disorders found in Usher syndrome but do not exhibit retinal degeneration.

A mouse model of the present invention for Usher syndrome develops both hearing and visual deficiencies characteristic of Usher syndrome. This mouse model is based on a mutation in the USH1C gene, USH1C216A, that results in the activation of a cryptic 5' splice site that is used preferentially over the normal 5' splice site. Splicing from the cryptic site produces a truncated mRNA and protein product. This mouse model provides an ideal tool to investigate therapeutic strategies for Usher syndrome and other diseases associated with mutations in splice sites. The present invention provides ASOs that promote correct splicing of the Ush1c216A gene and restore proper Ush1c expression in vitro and in vivo.

BRIEF DESCRIPTION OF THE DRAWINGS

FIG. 3A shows the results of a reverse transcription and polymerase chain reaction (RT-PCR) analysis of the splicing of Ush1c exon 3 and cells derived from Usher patients with the Ush1c216A mutation after the cells were treated with control ASO (−) or Ush1c_MO1 and demonstrating that the antisense oligonucleotides targeting Ush1 CG216A cryptic splice site redirects splicing to the major splice site that generates mRNA coding for full-length Ush1C (harmonin) protein. FIG. 3B quantifies the "correct"/ "cryptic" ratio for each lane in FIG. 3A.

FIGS. 4A-C. FIG. 4A shows the results of a RT-PCR analysis of the splicing of a Ush1c exon 3 in kidney tissue of Ush1C216A mice injected with Ush1c_MO1 to redirect splicing to the splice site that generates mRNA coding for the full-length protein. FIG. 4B quantifies the percentage of "correct" splicing shown in FIG. 4A. FIG. 4C quantifies the percentage of "cryptic" splicing shown in FIG. 4A.

FIG. 5A is a schematic of the Ush1c.216a plasmid and splicing of the transcripts from the minigene following treatment with ASOs. FIG. 5B shows RT-PCR analysis of RNA isolated from cells transfected with the minigene.

FIGS. 7A-G. FIG. 7A is a schematic representation of USH1C exons 2-4 gene structure, RNA splicing and protein products. Exons are represented by boxes and lines are introns. Diagonal lines indicate splicing pathways. The locations of the 216A mutation and the cryptic splice site are labeled. FIG. 7B (top) is a diagram of ASOs used in walk mapped onto the position of complementarity on USH1C. FIG. 7B (bottom) show radioactive RT-PCR of RNA isolated from HeLa cells transfected with USH1C.216A minigene and indicated ASO at a final concentration of 50 nM.

RNA spliced forms are labeled. Retain refers to transcripts with intron 3 retained and skip indicates exon 3 skipping. Quantitation of % correct splicing in graph is calculated as [(correct/(correct+cryptic+skip)]*100 and similarly for % cryptic. FIG. 7C shows sequence and USH1C target region (SEQ ID NO: 64) of ASO 2'MOE-29 (Sequence ID No. 33). FIG. 7 also discloses sequences for 2'MOE-49, 2'MOE-48 and 2'MOE-28 as SEQ ID NOS 59, 53 and 32, respectively. FIG. 7D (top) RT-PCR analysis of RNA isolated from an Ush1c.216AA knock-in mouse kidney cell line treated with increasing concentrations of 2'MOE-29 (Sequence ID No. 33) targeted to the Ush1c.216AA cryptic splice site. (bottom) Quantitation of splicing in treated cells represented as the % of correct splicing [correct/(correct+cryptic+skip)]× 100 or cryptic splicing [cryptic/(correct+cryptic+skip)]× 100. FIG. 7E shows Western blot analysis of harmonin protein in lysates from cells treated with increasing concentrations of 2'MOE-29 (Sequence ID No. 33). FIG. 7F shows RT-PCR analysis of RNA isolated from kidneys of adult Ush1c 216AA mice treated with different doses of 2'MOE-29 (Sequence ID No. 33). 2'MOE was administered by interperitoneal injection twice a week for two weeks. After treatment regimen, total RNA samples were prepared from kidney isolated 24 hours and analyzed by radioactive RT-PCR. Samples from individual representative mice are shown. Graph shows quantitation of Ush1c splicing to the correct splice site [correct splicing/(correct+skipping+cryptic)×100]. An asterisk (*) indicates a significantly higher percentage of correct splicing in 2'MOE-29 treated samples compared to vehicle (n=3, two-tailed Student's t-test). FIG. 7G shows RT-PCR analysis of RNA isolated from kidneys of P35 mice that were injected with 300 mg/kg of 2'MOE-29 (Sequence ID No. 33) or a control 2'MOE (2'MOE-C) at P5. Ush1c spliced products are indicated and quantitated as described above. Error bars, SEM.

FIG. 8A shows and open-field pathway trace of mice at age P22. Results from a representative mouse in each group are shown. FIG. 8B shows bar graphs quantifying the number of rotations in 120 sec. p value was calculated using the two-tailed student t-test.

FIG. 9A show representative audiograms from 8 kHz stimulus of 216AA mutant mice injected with mismatch control ASO (2'MOE-C, left panel), 216AA mice injected with USH1C ASO (2'MOE-29 (Sequence ID No. 33), middle panel) or heterozygote 216GA ctl mice injected with mismatch control (2'MOE-C, right panel) at P5. FIG. 9B shows the average ABR thresholds to BBN or pure tones ranging in frequency from 8 to 32 kHz in 216AA mutant mice (AA, 2'MOE-C), 216AA treated with 2'MOE-29 (AA, 2'MOE-29) or 2'MOE-C treated heterozygous or wildtype mice (GA/GG). >error bars=SEM; n>8. FIG. 9C shows the average ABR thresholds to 8 kHz in 216AA mice treated with 2'MOE-C or 2'MOE-29 or control mice (GA) at 1, 2, and 3 months of age. FIG. 9D shows RT-PCR analysis of cochlea RNA isolated at P32-P35 from mice treated with control or USH1C 2'MOE at P3-5. Spliced products are labeled. FIG. 9E show Western blot analysis of harmonin in cochlea isolated at P32-35 from mice that were treated at P5. Different isoforms of harmonin expressed from USH1C are indicated. Blots were also probed with a β-actin-specific antibody for a loading reference.

DETAILED DESCRIPTION OF THE INVENTION

Figure 1:
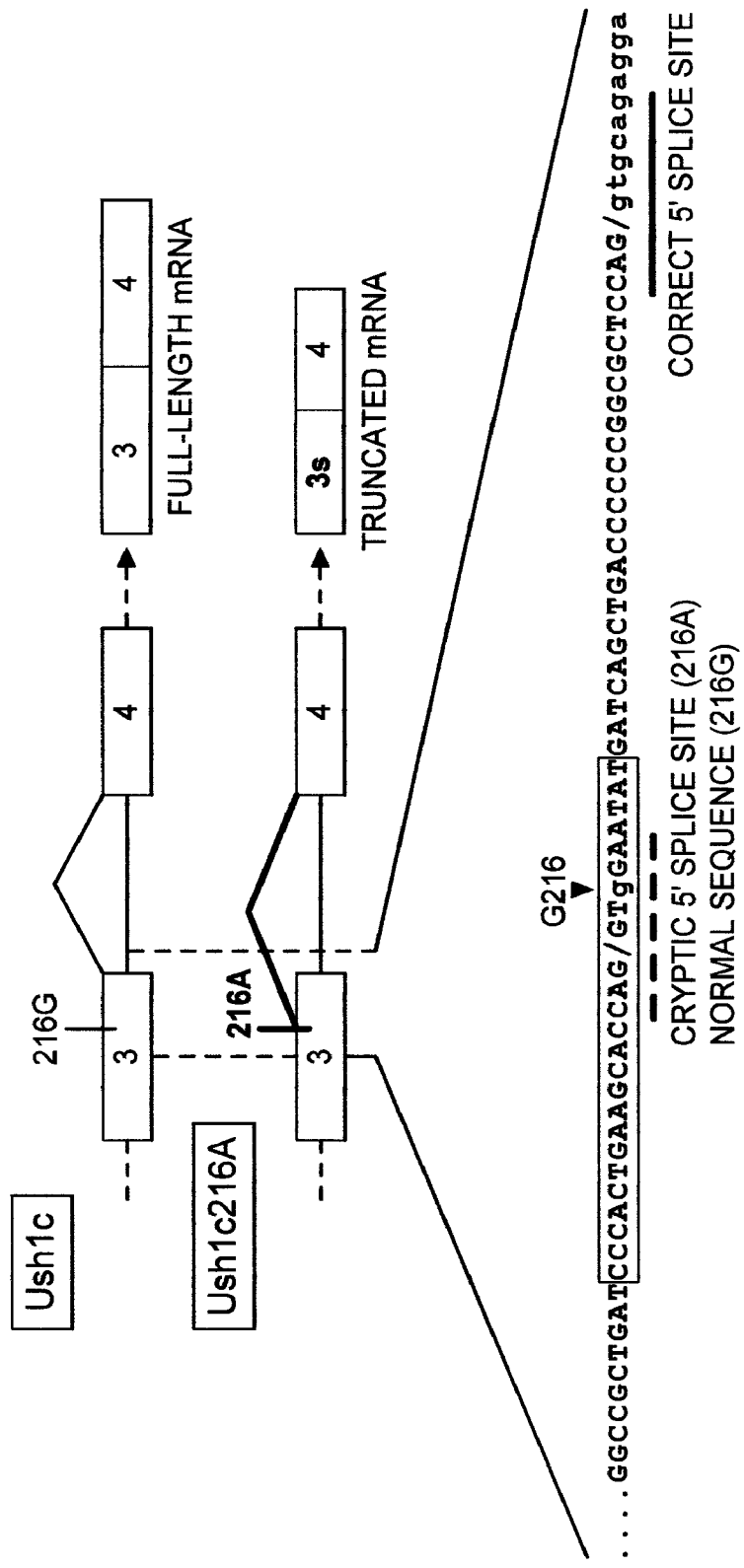
FIG. 1 is a representation of the splicing of an Ush1c gene (SEQ ID NO: 63) which provides a full-length mRNA and a mutant Ush1c216A gene that produces a truncated mRNA.

While this invention is susceptible of embodiment in many different forms, there is shown in the drawings, and will be described herein in detail, specific embodiments thereof with the understanding that the present disclosure is to be considered as an exemplification of the principles of the invention and is not intended to limit the invention to the specific embodiments illustrated.

The present invention provides therapeutic treatment of Usher syndrome by administering an effective amount of an antisense oligonucleotide (ASO) to Usher patients with the Ush1C216A mutation. A recently developed mouse model (Lentz et al., 2006) for Usher syndrome based on an Acadian Usher mutation in Ush1c gene, harmonin has been used to develop a therapeutic treatment for human patients. As used herein, "Ush 1 c gene" means a gene described in Lentz, J, Pan, F, Ng, S S, Deininger, P, Keats, B. 2007. Ush1c216A knock-in mouse survives Katrina. Mutat. Res. 616: 139-144 and having a sequence [ENSG00000006611 Accession number] provided herein as SEQ ID NO. 1, or a variant thereof. In certain embodiments, an Usher gene is at least 90% identical to Accession Number ENSG00000006611, set forth as SEQ ID NO 1.

FIG. 1 shows the Ush1c216A mutation is located in exon 3 of the gene and creates a cryptic 5' splice site which is used preferentially over the correct splice site (Bitner-Glindzicz et al., 2000; Verpy et al., 2000; Lentz et al., 2004). The resulting mRNA is out of frame and codes for a truncated protein product. The Ush1c216A mouse has the 216A mutation knocked into the mouse Ush1c gene. Mice homozygous for the Ush1c216A mutation exhibit classic circling behavior indicative of severe vestibular dysfunction and deafness. The mice also show evidence of retinal degeneration.

Pre-mRNA Splicing

Pre-mRNA splicing involves the precise and accurate removal of introns from the pre-messenger RNA and the ligation of exons together after intron removal to generate the mature mRNA which serves as the template for protein translation. Pre-mRNA splicing is a two-step reaction carried out by a spliceosome complex comprising protein and small RNA components which recognize conserved sequence elements within the introns and exons of the RNA. Recognition of these sequence elements, including the 5' splice site, 3' splice site and branch point sequence, is the primary mechanism directing the correct removal of introns.

Splicing requires direct base-pairing between small nuclear RNA (snRNA) components of the spliceosome and the splice site nucleotides of the mRNA. This interaction can be easily disrupted by gene mutations or by artificial blocking using short oligonucleotides complementary to the RNA. Such so called antisense oligonucleotides (ASOs), when designed to be complementary to a splice sites, will compete for base-pairing with the snRNAs, thereby blocking an essential step in splicing at the site. In this way, antisense oligonucleotides can potently block unwanted splicing or redirect splicing to alternative splice sites.

Therapeutic Perspectives

Mutations that alter pre-mRNA splicing are found in more than 50% of genes associated with deafness. Developing methods to manipulate splicing will benefit the development of therapies for all disease-associated mutations that affect splicing. Although disease-causing mutations that disrupt splicing are common, there are relatively few tools available to study these types of defects in vivo. Only a handful of animal models for disease have been developed that are based on splicing mutations. Animal models for SMA that reproduce the exact splicing defect in SMA in humans have been instrumental in the forward progress that has been made in developing potential therapeutics for the disease (Hua et al., 2010). Many of these therapies are based on either small molecule compounds or ASOs that alter the splicing pattern of the pre-mRNA (Sumner 2006).

ASOs have been effectively used to alter pre-mRNA splicing (for review, Aartsma-Rus & van Ommen 2007; Smith et al., 2006). ASOs targeted to cryptic splice sites created by mutations in the ATM gene were recently demonstrated to effectively redirect splicing to the correct splice site and improve protein expression (Du et al., 2007). The first clinical trials based on ASO-induced skipping of exons as a therapy for Duchenne muscular dystrophy (DMD) have shown success in increasing dystrophin protein levels in muscle cells surrounding the site of injection (van Deutekom et al., 2008). ASO-based therapies may provide a customizable approach to mutation-based treatments for disease. The effectiveness of ASOs in modulating splicing in a therapeutically beneficial manner has been demonstrated for a number of diseases.

One preferred form of the invention provides a therapeutic treatment of human subjects having Usher syndrome by administering to the human subject an ASO oligonucleotide having 8 to 30 linked nucleosides having a nucleobase sequence comprising a complementary region comprising at least 8 contiguous nucleobases complementary to a target region of equal length within exon 3 of an Usher transcript.

In a preferred form of the invention, suitable ASOs when administered to a patient in need thereof will promote the correct splicing of the USH1C216A transcript to provide an mRNA which serves as the template for transcribing the full-length, harmonin protein. More preferably, suitable ASOs will complementary base pair to an effective number of nucleotides of exon 3 of the pre-mRNA transcript of the USH1C216A mutation to redirect the splicing from the cryptic 5' splice site to the major 5' splice site. In a more preferred form of the invention, suitable ASOs will complementary base pair to consecutive nucleotides of exon 3 and have a length of 8 to 30 mer, more preferably 15 to 30 mer, even more preferably 15 to 27 mer and most preferably 15-25 mer or any range or combination of ranges therein.

Suitable ASOs can be chemically modified to be different from their natural nucleic acid structure to prevent enzymatic degradation, triggering of the innate immune response or inflammation response. Chemical modifications can be nucleoside modification (i.e., to the sugar moiety and or to the nucleobase moiety) and/or modifications to internucleoside linkages. In one preferred form of the invention, suitable ASOs have their nucleic acid bases bound to a morpholine ring instead of a ribose ring and are linked through a non-ionic phosphorodiamidate groups instead of an anionic phosphodiester group. These modified oligonucleotides are available from Gene Tools under the tradename MORPHOLINO.

Other suitable modifications include replacing the ribose rings with furanosyl or substituted furanosyl rings where the substituents, in some instances but not necessarily, form bridges within the furanosyl ring to form bicyclic sugars or bridges to other ring structures to form tricyclic sugars. Nucleosides that contain bicyclic and tricylic sugar moieties shall be referred to respectively as bicyclic nucleosides and tricyclic nucleosides and those that contain a single ring may be referred to as monocyclic. It is also contemplated replacing the oxygen atom in the furanosyl with a non-oxygen atom such as carbon, sulfur or nitrogen. In a more preferred form of the invention, the furanosyl 2'-position will have a 2-methoxy ethyl ether substituent with the following structure —O $CH_2CH_2OCH_3$ ("2'-MOE"). Suitable chemically modified ASOs are available from Isis Pharmaceuticals, Inc.

It is also contemplated that the ASOs may have conjugate groups attached thereto, as is well known in the art, to provide a desired property or characteristic such as pharmacodynamics, pharmacokinetics, stability, targeting, binding, absorption, cellular distribution, cellular uptake, charge and clearance.

The present invention further provides therapeutic dosage forms for delivery to a human subject. It is contemplated that the ASOs described herein can be delivered by any suitable route of administration including parenteral, oral, injection, transdermal, intramuscular, topical, or other route of administration known to those skilled in the art. In a most preferred form of the invention the ASO is injected directly into the eye or ear or both of the human subject.

Morpholino Oligonucleotides Examples

Example 1

Development of an Ush1c216a Splicing System to Test ASOs and Small Molecules

The present invention provides an Ush1c and Ush1c216A minigene comprising exon 3, intron 3 and exon 4 of the Ush1c gene. These minigenes are used as templates to create wild-type and G216A mutant Ush1c mRNA that can be spliced in HeLa nuclear extract. The splicing of these transcripts in HeLa nuclear extract results in faithful recapitulation of the expected full-length splicing of the wild-type gene and cryptic splicing from the G216A mutated transcript. These results demonstrate that this cell-free system can be used to accurately model normal and disease-associated splicing caused by the G216A mutation.

Figure 2:
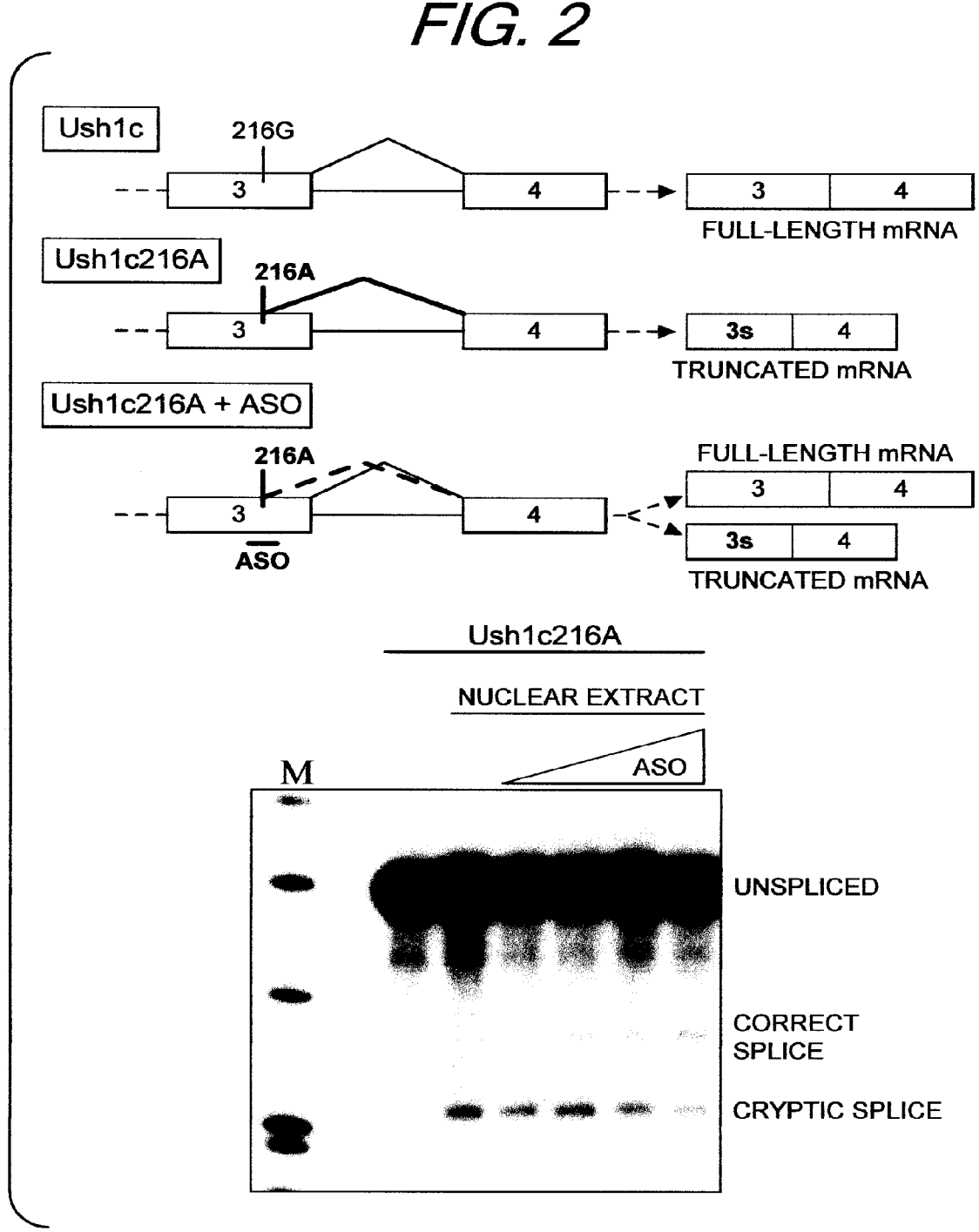
FIG. 2 is a representation of a cell-free splicing analysis of Ush1c and Ush1c216A exon 3 in HeLa nuclear extract.

We next tested several ASOs targeted to the cryptic 5' splice site in the cell-free splicing system and assessed switching from the use of the cryptic 5' splice site to the correct 5' splice site. FIG. 2 shows these ASOs effectively increased splicing to the correct 5' splice site in a dose-dependent manner. These results demonstrate the utility of the cell-free splicing system for testing ASOs and the ability to modulate the use of the cryptic and normal 5' splice site using ASOs.

Example 2

ASOs that Improve Ush1c216a Splicing in Cell Culture

The effectiveness of ASOs in achieving splice-site switching in cultured cells was tested. An Ush1c minigene expression system was created to test the effect of the ASOs on the splicing mutant Ush1c gene transcripts in cells. The ASOs effectively correct the defective splicing and result in the generation of normally spliced mRNA.

We have also developed cell lines from the tissues of Ush1C 216A mice that carry the human mutation that creates the cryptic splice sites. The ASOs potently redirect splicing to the correct splice site thereby rescuing Ush1c expression.

Figure 3A:
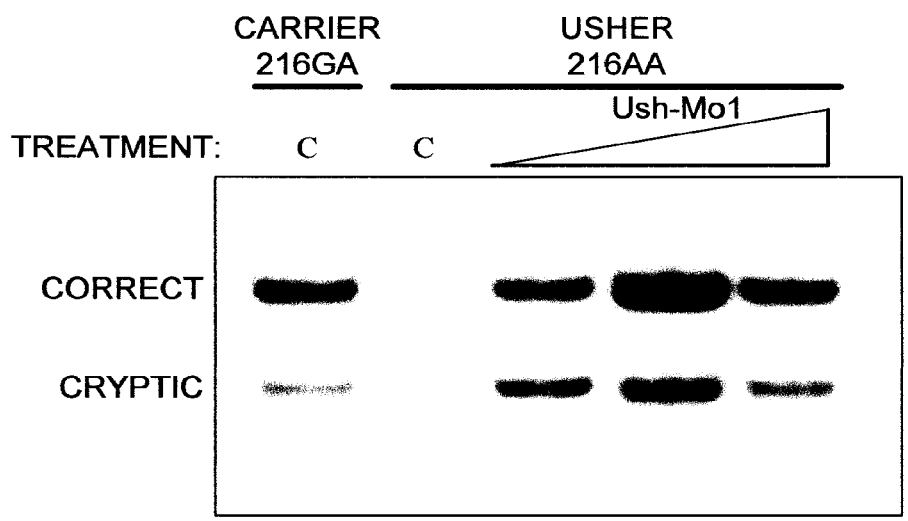
FIGS. 3A-B.
Figure 3B:
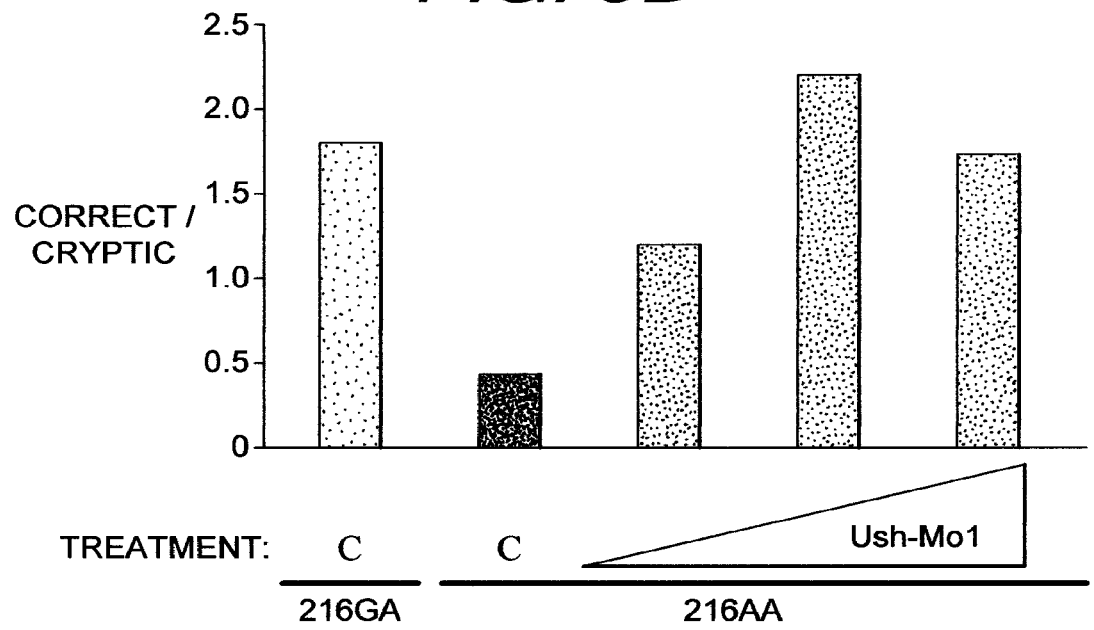

FIG. 3 shows that we have successfully corrected splicing of Ush1C 216A mRNA arising from the human Ush1C216A gene in cell lines derived from a patient with Usher Syndrome carrying the Ush1C216A mutation in the Ush1C gene.

Example 3

Correction of Ush1c216A Exon 3 Cryptic Splicing in Mice Using Optimized ASOs The ASOs that we have utilized shown in Table 1,2 to target cryptic splicing in Usher syndrome shown herein have been tested in an Ush1c.216a minigene expression system (Table 1) and in the Ush1c216A knock-in Usher syndrome mouse model (Table 2). FIG. 4 shows that the preliminary results indicate that the ASOs correct splicing in the cells of a number of tissues such as the kidney, and that this effect can last for at least 29 days after the final treatment.

TABLE 1

Modulation of Ush1c.216A splicing of RNA transcripts from a Ush1c.216A minigene.

| MORPHOLINO NO | Start Site | Sequence | Region | % cryptic splicing | SEQ ID NO |
|---|---|---|---|---|---|
| Ush1C_MO1 | 138577 | AGCTGATCATATT CTACCTGGTGCT | USH1C Exon 3 (G to A mt) | 2.84 | 2 |
| Ush1C_MO2 | 138569 | ATATTCCACCTGG TGCTTCAGTGGG | USH1C exon 3 (G/A mt) | 5.75 | 3 |

TABLE 2

Modulation of Ush1c.216A splicing in mice kidney using vivo-morpholinos

| MORPHOLINO NO | Start Site | Sequence | Region | % cryptic splicing | SEQ ID NO |
|---|---|---|---|---|---|
| N/A | N/A | N/A | control treated | 99.543 | N/A |
| Ush1C_MO1 | 138577 | AGCTGATCATA TTCTACCTGGT GCT | USH1 C exon 3 (G to A mt) | 11.45 | 4 |

Isis Pharmaceutical 2'-MOE Examples

Example 4

Ush1c.216a Minigene

Figure 5A:
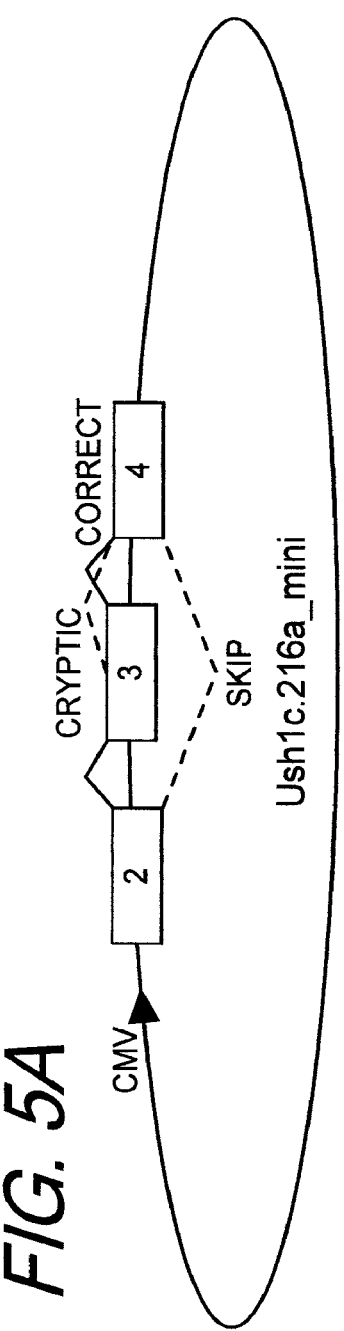
FIGS. 5A-B.
Figure 5B:
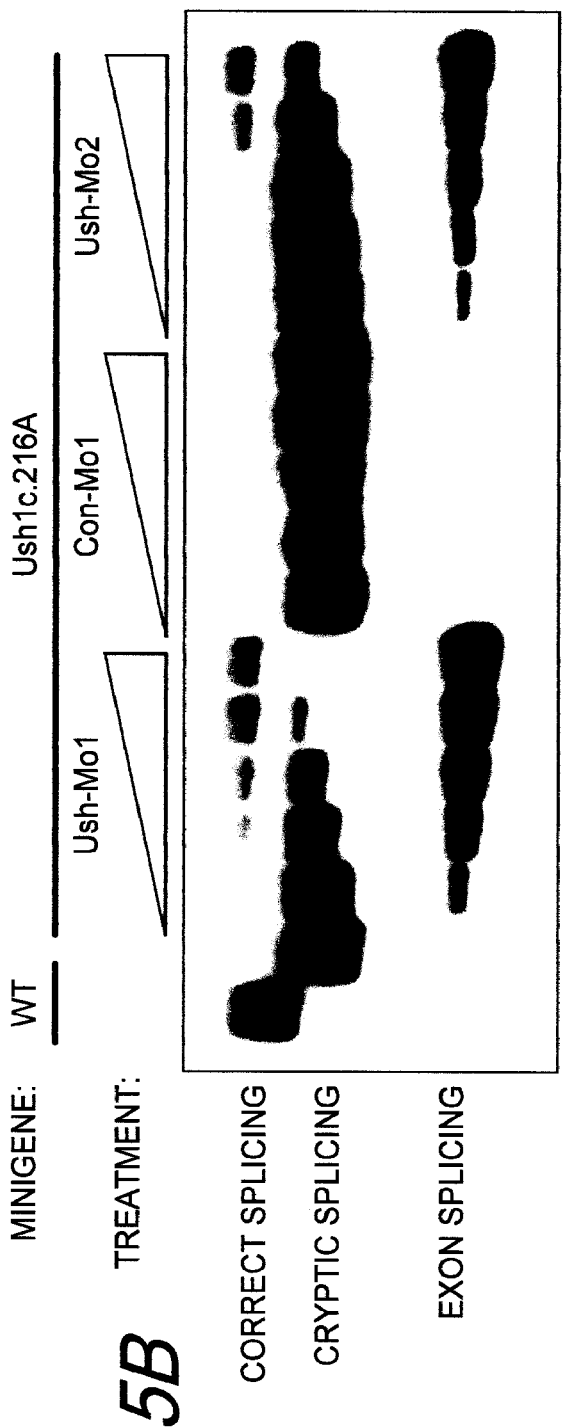

A plasmid comprising an Usher 1C minigene having a 216A mutation (Ush1c.216a) was prepared using standard molecular biology techniques. The Ush1c.216a plasmid included exons 2, 3, and 4, and introns 2 and 3. The minigene was under control of the CMV promoter. A schematic of the Ush1c.216a plasmid appears in FIG. 5.

Example 5

Antisense Modulation of Usher RNA Transcript Splicing

Antisense oligonucleotides complementary to different regions of the Usher transcript were tested for their ability to modulate splicing of RNA transcripts expressed from the Usher minigene. Antisense oligonucleotides comprising 2'MOE modified nucleosides (Tables 3,4) in which each nucleoside of the oligonucleotides was a 2'-MOE modified nucleoside and internucleoside linkages were phosphorothioate linkages. All of the nucleobases were unmodified and cytosine bases were 5-meC.

To test the ability of the antisense oligonucleotides to modulate Usher transcript splicing, HeLa cells were co-transfected with the Ush1c.216a plasmid from Example 4 and an antisense oligonucleotide (or no antisense oligonucleotide in the case of the untreated control). The results are summarized in Tables 3,4). The start site is the position relative to 13475 of SEQ ID NO 1.

TABLE 3

Modulation of USH1C pre-mRNA splicing by Isis 18 nucleotide 2'-MOE modified oligonucleotides shown 5' to 3' direction.

| ISIS NO | Start Site | Sequence | Region | % cryptic splicing | SEQ ID NO |
|---|---|---|---|---|---|
| N/A | N/A | N/A | Untreated Control | 100 | N/A |
| 527106 | 138475 | ACGGCCACGTCCAT GGTC | USH1C exon 3 | 13.39 | 5 |
| 527107 | 138480 | CGAGCACGGCCACG TCCA | USH1C exon 3 | 6.29 | 6 |
| 527108 | 138485 | TCCCACGAGCACGG CCAC | USH1C exon 3 | 9.93 | 7 |
| 527109 | 138490 | AGGTCTCCCACGAG CACG | USH1C exon 3 | 32.49 | 8 |
| 527110 | 138495 | GCTTCAGGTCTCCC ACGA | USH1C exon 3 | 34.79 | 9 |
| 527111 | 138500 | GACCAGCTTCAGGT CTCC | USH1C exon 3 | 64.21 | 10 |
| 527112 | 138505 | TTGATGACCAGCTT CAGG | USH1C exon 3 | 23.89 | 11 |
| 527113 | 138510 | GTTCATTGATGACC AGCT | USH1C exon 3 | 34.68 | 12 |
| 527114 | 138515 | GCTGGGTTCATTGA TGAC | USH1C exon 3 | 41.71 | 13 |
| 527115 | 138520 | AGACGGCTGGGTTC ATTG | USH1C exon 3 | 12.15 | 14 |
| 527116 | 138525 | GAGGCAGACGGCTG GGTT | USH1C exon 3 | 36.97 | 15 |
| 527117 | 138530 | AAACAGAGGCAGAC GGCT | USH1C exon 3 | 26.32 | 16 |
| 527118 | 138535 | GCATCAAACAGAGG CAGA | USH1C exon 3 | 22.23 | 17 |
| 527119 | 138540 | GAATGGCATCAAAC AGAG | USH1C exon 3 | 29.63 | 18 |
| 527120 | 138545 | CGGCCGAATGGCAT CAAA | USH1C exon 3 | 63.65 | 19 |
| 527121 | 138550 | ATCAGCGGCCGAAT GGCA | USH1C exon 3 | 15.79 | 20 |

TABLE 3-continued

Modulation of USH1C pre-mRNA splicing by Isis 18 nucleotide 2'-MOE modified oligonucleotides shown 5' to 3' direction.

| ISIS NO | Start Site | Sequence | Region | % cryptic splicing | SEQ ID NO |
|---|---|---|---|---|---|
| 527122 | 138555 | GTGGGATCAGCGGC CGAA | USH1C exon 3 | 57.54 | 21 |
| 527123 | 138560 | CTTCAGTGGGATCA GCGG | USH1C exon 3 | 5.27 | 22 |
| 527124 | 138563 | TGCTTCAGTGGGAT CAGC | USH1C exon 3 | 3.61 | 23 |
| 527125 | 138566 | TGGTGCTTCAGTGG GATC | USH1C exon 3 | 9.68 | 24 |
| 527126 | 138569 | ACCTGGTGCTTCAG TGGG | USH1C exon 3 | 21.75 | 25 |
| 527127 | 138569 | ATATTCTACCTGGT GCTTCAGTGGG | USH1C exon 3 (G to A mt) | 16.77 | 26 |
| 527128 | 138571 | CTACCTGGTGCTTC AGTG | USH1C exon 3 (G to A mt) | 22.39 | 27 |
| 527129 | 138573 | TTCTACCTGGTGCT TCAG | USH1C exon 3 (G to A mt) | 24.45 | 28 |
| 527130 | 138576 | ATATTCTACCTGGT GCTT | USH1C exon 3 (G to A mt) | 14.89 | 29 |
| 527131 | 138577 | AGCTGATCATATTC TACCTGGTGCT | USH1C exon 3 (G to A mt) | 2.35 | 30 |
| 527132 | 138579 | ATCATATTCTACCT GGTG | USH1C exon 3 (G to A mt) | 12.13 | 31 |
| 527133 | 138581 | TGATCATATTCTAC CTGG | USH1C exon 3 (G to A mt) | 2.85 | 32 |
| 527134 | 138584 | AGCTGATCATATTC TACC | USH1C exon 3 (G to A mt) | 2.70 | 33 |
| 527135 | 138586 | TCAGCTGATCATAT TCTA | USH1C exon 3 (G to A mt) | 19.98 | 34 |
| 527136 | 138589 | GGGTCAGCTGATCA TATT | USH1C exon 3 | 98.82 | 35 |
| 527137 | 138591 | GGGGGTCAGCTGAT CATA | USH1C exon 3 | 99.28 | 36 |
| 527138 | 138593 | CGCCGGGGGGTCAG CTGA | USH1C exon 3 | 99.60 | 37 |
| 527139 | 138598 | TGGAGCGCCGGGGG GTCA | USH1C exon 3 | 90.93 | 38 |
| 527140 | 138603 | GCACCTGGAGCGCC GGGG | USH1C exon 3/ intron3 | 97.59 | 39 |
| 527141 | 138608 | CCTCTGCACCTGGA GCGC | USH1C exon 3/ intron3 | 99.81 | 40 |
| 527142 | 138613 | GGCTTCCTCTGCAC CTGG | USH1C exon 3/ intron3 | 99.54 | 41 |
| 527143 | 138618 | CTGGTGGCTTCCTC TGCA | USH1C intron 3 | 97.64 | 42 |
| 527144 | 138623 | CCAGCCTGGTGGCT TCCT | USH1C intron 3 | 96.34 | 43 |
| 527145 | 138628 | TGCCTCCAGCCTGG TGGC | USH1C intron 3 | 94.86 | 44 |
| 527146 | 138633 | CCCCCTGCCTCCAG CCTG | USH1C intron 3 | 96.78 | 45 |
| 527147 | 138638 | CTCCACCCCTGCC TCCA | USH1C intron 3 | 98.2 | 46 |
| 527148 | 138643 | GATCTCTCCACCCC CTGC | USH1C intron 3 | 97.94 | 47 |
| 527149 | 138648 | AGGGTGATCTCTCC ACCC | USH1C intron 3 | 97.82 | 48 |
| 527150 | 138653 | CGCCCAGGGTGATC TCTC | USH1C intron 3 | 94.03 | 49 |
| 527151 | 138658 | TGCCCCGCCCAGGG TGAT | USH1C intron 3 | 97.74 | 50 |
| 527152 | 138663 | AGCACTGCCCCGCC CAGG | USH1C intron 3 | 97.83 | 51 |

TABLE 4

Modulation of USH1C pre-mRNA splicing by Isis 2'-MOE modified 15 nucleotide oligonucleotides shown in 5' to 3' direction.

| ISIS NO | Start Site | Sequence | Target | % cryptic splicing | SEQ ID NO |
|---|---|---|---|---|---|
| 535400 | 138579 | ATATTCTAC CTGGTG | USH1C exon 3 (G to A mt) | 53.03 | 52 |
| 535401 | 138580 | CATATTCTA CCTGGT | USH1C exon 3 (G to A mt) | 61.03 | 53 |
| 535402 | 138581 | TCATATTCT ACCTGG | USH1C exon 3 (G to A mt) | 66.12 | 54 |
| 535403 | 138582 | ATCATATTC TACCTG | USH1C exon 3 (G to A mt) | 41.61 | 55 |
| 535404 | 138583 | GATCATATT CTACCT | USH1C exon 3 (G to A mt) | 22.64 | 56 |

TABLE 4-continued

Modulation of USH1C pre-mRNA splicing by Isis 2'-MOE modified 15 nucleotide oligonucleotides shown in 5' to 3' direction.

| ISIS NO | Start Site | Sequence | Target | % cryptic splicing | SEQ ID NO |
|---------|-----------|----------|--------|--------------------|-----------|
| 535405  | 138584    | TGATCATATTCTACC | USH1C exon 3 (G to A mt) | 27.35 | 57 |
| 535406  | 138585    | CTGATCATATTCTAC | USH1C exon 3 (G to A mt) | 20.08 | 58 |
| 535407  | 138586    | GCTGATCATATTCTA | USH1C exon 3 (G to A mt) | 16.79 | 59 |
| 535408  | 138587    | AGCTGATCATATTCT | USH1C exon 3 (G to A mt) | 72.49 | 60 |
| 535409  | 138588    | ATCATATTCTAC | USH1C exon 3 (G to A mt) | 98.38 | 61 |

Example 6

Antisense Modulation of Usher Transcript

Figure 6:
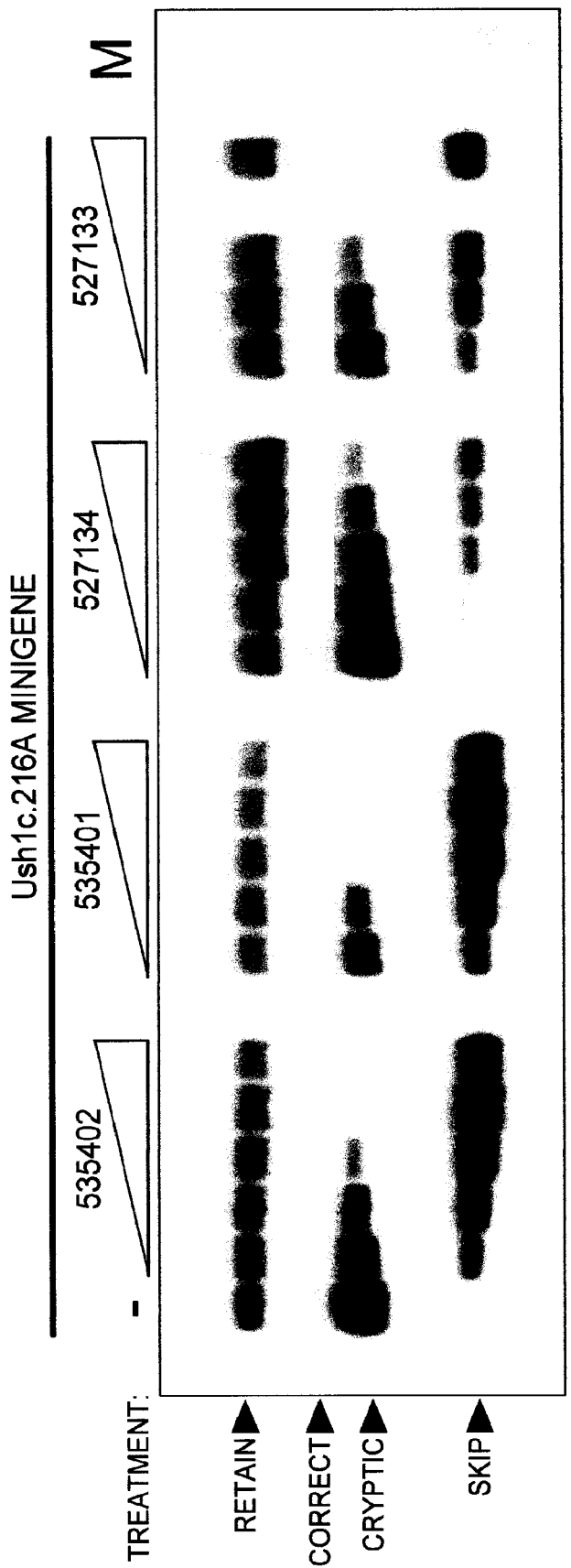
FIG. 6 summarizes the results of RT-PCR of four 2' MOE oligonucleotides.

Four of the antisense oligonucleotides above were separately tested at varying doses (0 (control), 5 nM, 10 nM, 20 nM, 40 nM, and 80 nM). Each antisense oligonucleotide reduced the amount of cryptic spliced transcript and increased the amount of correctly spliced or exon 3-skipped transcript in a dose-dependent manner. RNA was collected and analyzed by RT-PCR. Results are summarized in FIG. 6.

Example 7

In Vivo Modulation of the Usher Transcript

Mice having the 216A mutation in their Ush1c gene have been described. Such mice have congenital hearing loss and retinal degeneration. Four of the above described antisense oligonucleotides are shown in their 3' to 5' direction in FIG. 7C (527133, 527134, 535401, and 535407 (Sequence ID Nos. 32, 33, 53 and 59 respectively)) were administered to such mice to test their ability to modulate splicing in vivo. Doses of 50 mg/kg were administered by intraperitoneal injection twice each week for two weeks. Two days after the final injection, the mice were euthanized and RNA was isolated from various tissues. RNA was analyzed by radiolabeled RT-PCR. Splicing modulation was detected in the tissues of treated mice.

Example 8

Correction of Hearing and Vestibular Dysfunction in a Mouse Model for Deafness

Figure 7A:
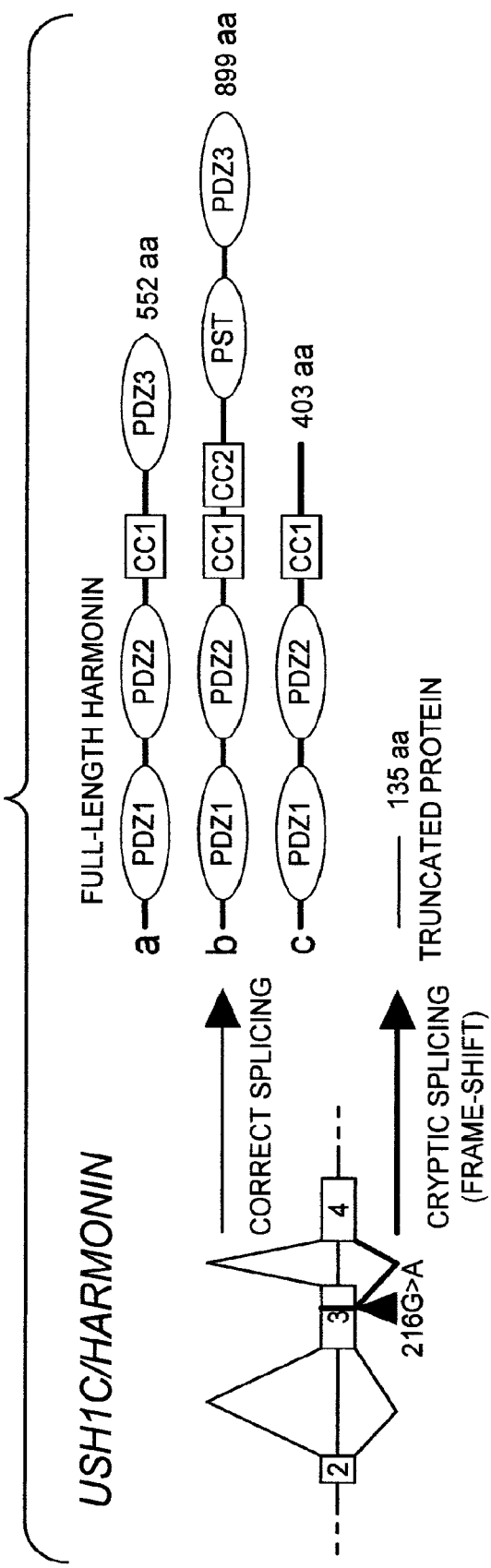

Hearing defects are present in approximately 1 in 500 newborns, and in developed countries, frequently result from single locus gene mutations[1,2]. Here, we use a mouse model of congenital, inherited deafness to investigate a potential cure for hearing loss and vestibular dysfunction using an antisense oligonucleotide splice targeting approach. Mice homozygous for the Ush1c.216A mutation (216AA), which causes Usher syndrome in humans, exhibit circling behavior indicative of severe vestibular dysfunction and deafness[3]. ASOs were designed to specifically redirect splicing of USH1C 216A RNA transcripts from a cryptic splice site, which is activated by the mutation, to the authentic site (FIG. 7A). ASOs were optimized in cell-free and cellular assays and are shown to correct splicing of the disease 216A RNA in an Usher syndrome patient cell line. A single treatment of ASOs in 216AA neonate mice corrects splicing in the cochlea, eliminates vestibular dysfunction and restores hearing to a level comparable to wild-type mice. Our results indicate a cure for deafness and vestibular dysfunction in mice using ASOs, demonstrating that hearing can be treated by correction of gene expression at an early stage in development.

Figure 7B:
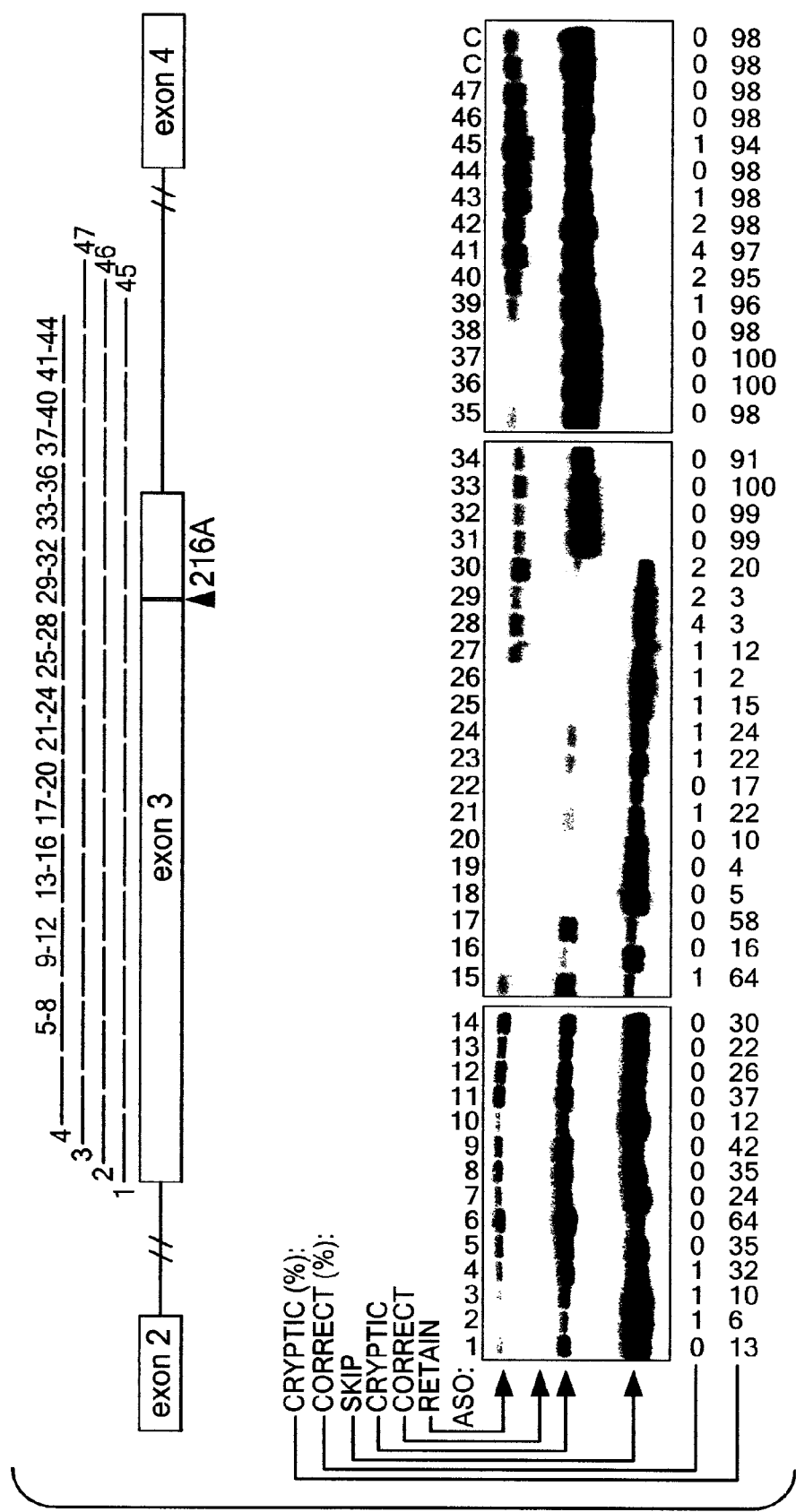

To identify ASOs that can block splicing at the cryptic splice site created by the 216A mutation, we constructed an USH1c minigene (FIG. 5) comprising exons 2-4 and the intervening introns of human USH1C 216G (WT) or 216A cloned into an expression plasmid. The minigene plasmids and ASOs with 2'-O-methoxyethyl (2'-MOE) sugar modifications and a phosphodiester backbone were transfected into cells and splicing was analyzed after 48 hours by radiolabeled, reverse-transcription PCR (RT-PCR) analysis of isolated RNA. Forty-seven 2'-MOE 18-mer ASOs complementary to regions in exon 3 and the 5' end of intron 3 as set forth in Table 3 above were tested and ten 2'-MOE 15-mer ASOs as shown in Table 4. The ASOs start with the first position of exon 3, with overlapping ASOs providing coverage in 5-nucleotide increments (FIG. 7B). The premise of these experiments is that there may be exonic splicing enhancers or silencers that could be targeted to modulate splicing of the cryptic or correct splice site. ASOs targeted to the region surrounding the 216A mutation strongly blocked cryptic splicing and promoted correct splicing. Many of the ASOs-targeted to regions throughout the exon also caused skipping of exon 3. The mRNA lacking exon 3 encodes a full-length protein lacking 48 amino acids flanking the N-terminus of the first PDZ domain of the protein. ASOs identified as 2'MOE 28 and 29 in FIG. 7C correspond to Isis Nos. 527133 and 527134 (Sequence ID Nos. 32 and 33) in Table 3 were most effective at correcting splicing and blocking cryptic splicing (FIG. 7B).

Optimal ASO concentrations for blocking cryptic splicing and restoring correct splicing was tested using the USH1C minigene expression system described above and treating cells with increasing concentrations of 2'MOEs that were most effective in the ASO walk experiments (2'MOE-28, 29 or Sequence ID Nos. 32 and 33) along with shorter versions of these ASOs (2'MOE-48,49, Isis Nos. 535401 and 535407, Sequence ID Nos. 53 and 59 respectively in Table 4) (FIG. 7C). All of the 2'MOE ASOs blocked cryptic, with cryptic splicing nearly abolished in samples treated with 12 µM ASO (FIG. 7D).

Figure 7E:
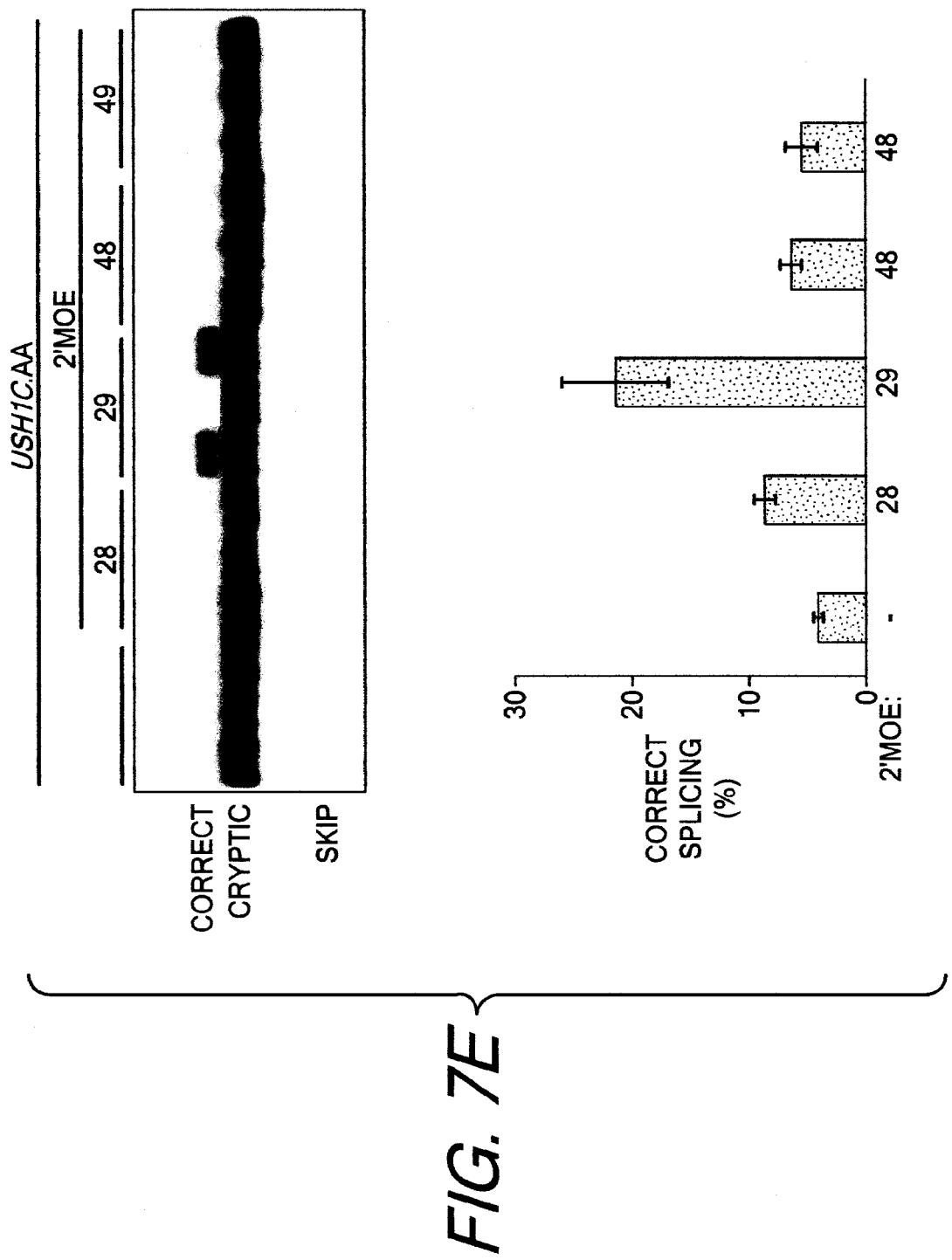
Figure 7F:
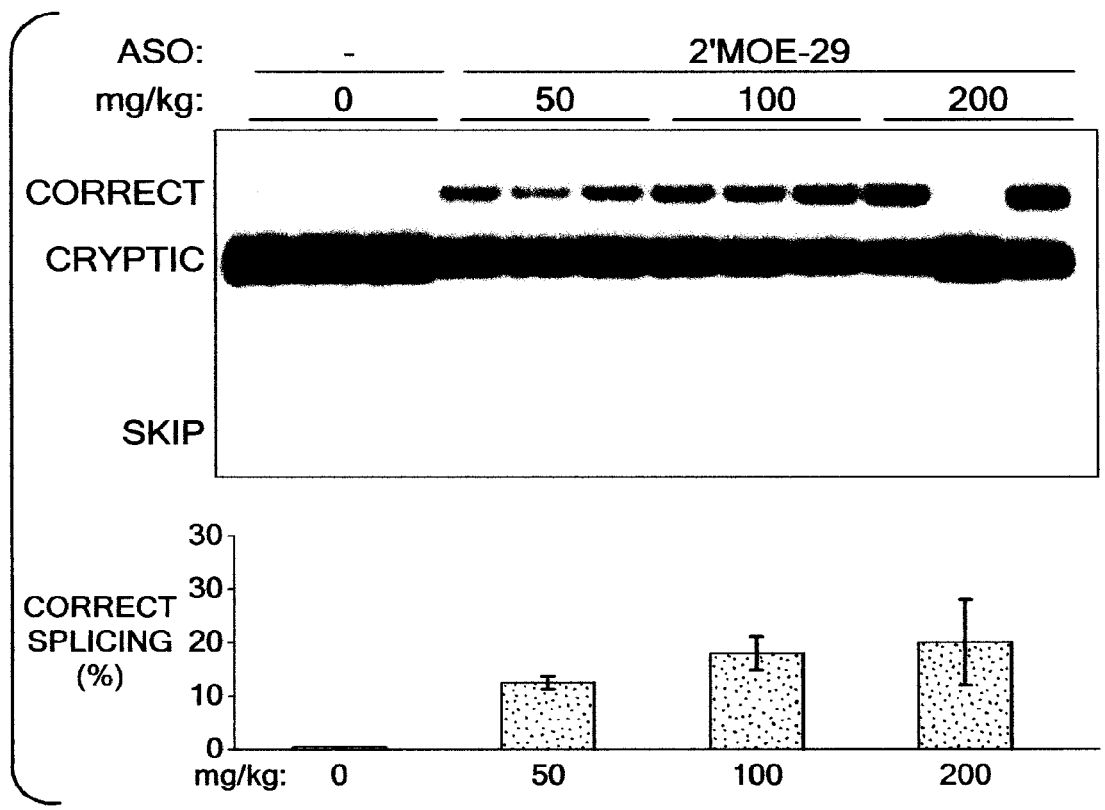
Figure 7G:
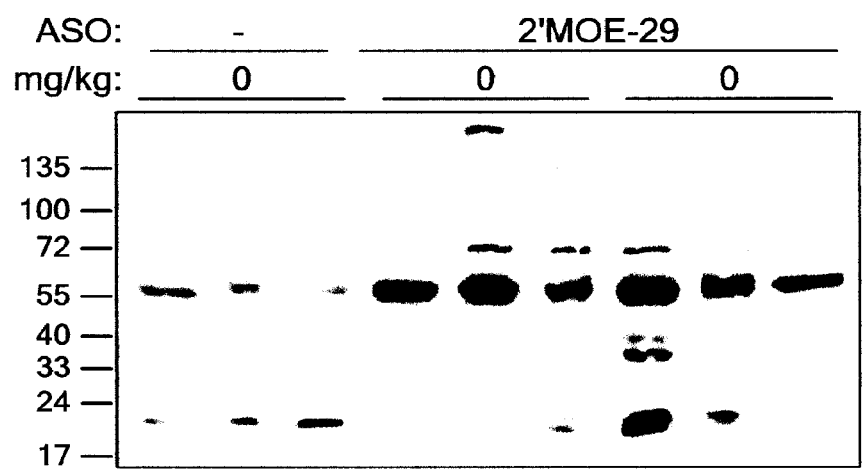

To test the effect of ASOs in vivo, adult Ush1c.216AA mice were injected with 50 mg/kg of 2'MOE-28, 29, 48 or 49 (Sequence ID Nos. 32, 33, 53 and 59) twice a week for two weeks for a total of four injections and kidneys were collected 24 hours after the final injection. 2'MOE-29 corrected splicing of 216AA in the kidney of treated mice (FIG. 7E). Optimal dosing was determined by injecting mice with different amounts of 2'MOE-29 using the dosing regimen described above. 2'MOE-29 corrected splicing and increased harmonin protein expression in a dose-dependent manner (FIGS. 7F,G). No change in behavior was evident in the adult mice following ASO injection.

Figure 8A:
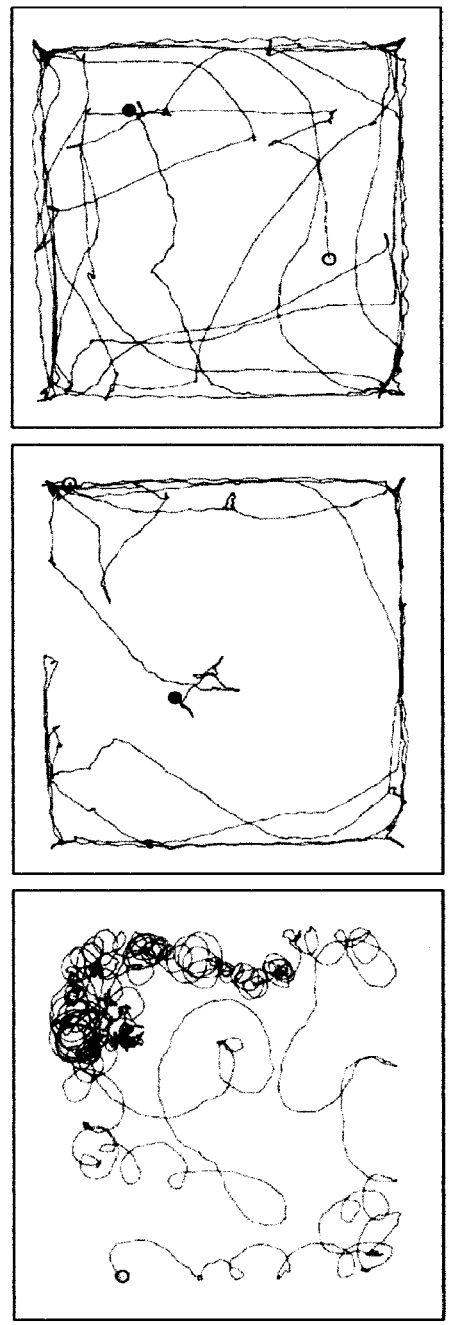
FIGS. 8A-B show the results of experiments indicating that ASOs correct vestibular dysfunction in Ush1c.216AA mice.
Figure 8B:
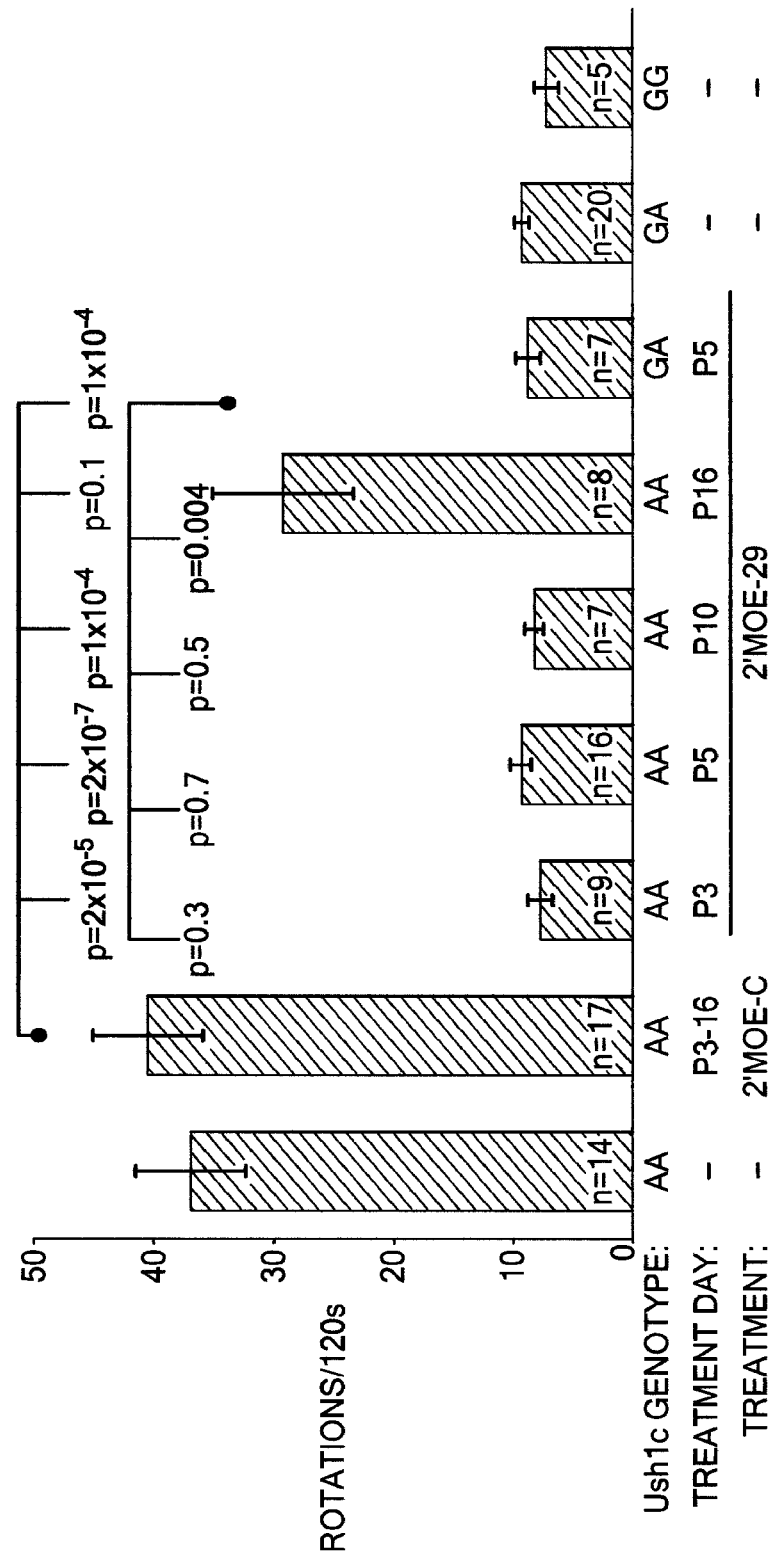

Harmonin is first expressed between embryonic day 15 and postnatal day 15 (P15)[4], during the time when hearing is being established suggesting that neonate expression of harmonin may be critical for hearing development. Thus, we treated neonatal mice and tested the ability of the ASOs to correct vestibular and hearing defects. Mice were treated at P3, P5, P10 or P16 by intraperitoneal injection of 2'MOE-29 (Sequence ID No. 33). Untreated mice or those treated with a mismatched 2'MOE (2'MOE-C) ASO displayed general hyperactivity and circling behavior characteristic of the vestibular defects and deafness by postnatal day 21 (FIG. 8A) as previously reported[5]. In contrast, the behavioral activity of mice treated with 2'MOE-29 (Sequence ID No. 33) was indistinguishable from heterozygote 216GA or wildtype 216GG mice, with no circling, head-tossing or hyperactivity (FIGS. 8A,B). There was no discernable difference between mice treated at P3, P5 or P10, whereas P16-treated mice were indistinguishable from untreated mutant 216AA mice (FIG. 8B). The oldest P5 2'MOE-29-treated mice are now 6 months of age and do not exhibit hyperactivity or circling behavior, suggesting that the ASOs can effectively treat the vestibular dysfunction associated with Usher syndrome when delivered early in neonate development.

Figure 9A:
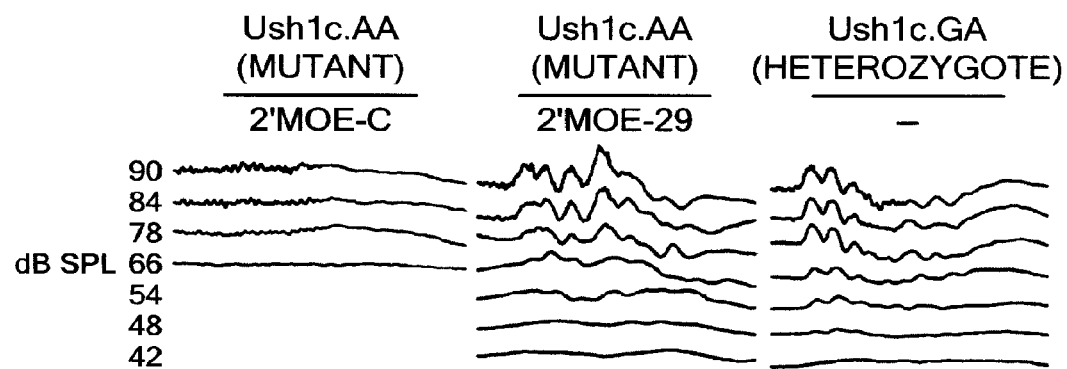
FIGS. 9A-E shows the correction of deafness in mice treated at P3-P5.
Figure 9B:
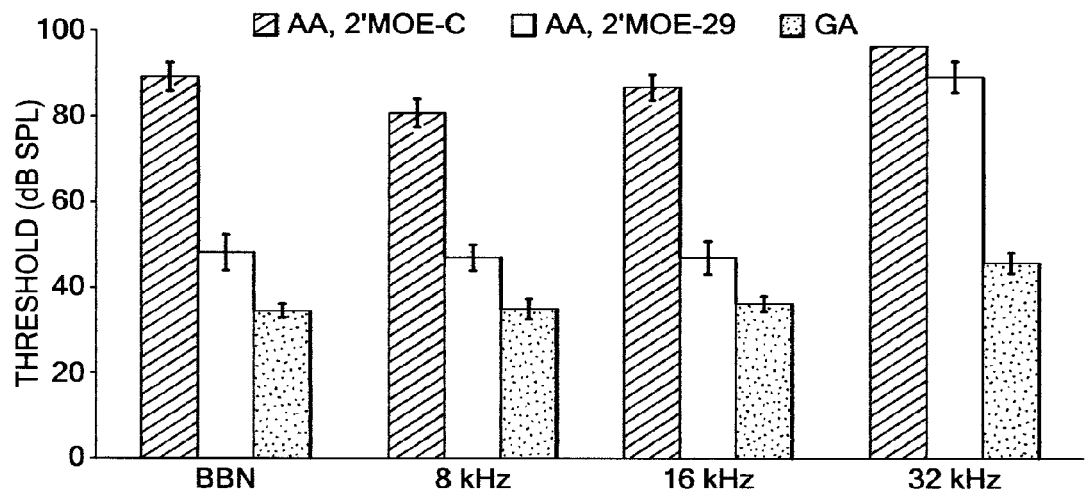

To assess hearing function, auditory-evoked brainstem response (ABR) analysis was performed. ABR thresholds to broad-band (BB) and pure tone stimuli (8, 16 and 32 kHz) were compared in one month old 216AA mutant mice treated with 2'MOE-29 (Sequence ID No. 33) with those of age-matched control mice. The following control mice were used: treated and untreated wild type (wt, 216GG) and heterozygote (het, 216GA) mice (referred to as wt/het ctl); and untreated mutants and mutants treated with 2'MOE-C (mut 2'MOE-C). Wt and het littermates had the expected thresholds of mice with normal hearing, and there was no difference with treatment (2'MOE-29 (SEQ. ID No. 33) or 2'MOE-C) (FIGS. 9A,B). Untreated mutants (216AA) and mutants treated with the mismatched 2'MOE-C had an abnormal (fewer peaks or greater interpeak latency) or no response at 90 dB SPL to BB or pure tones (FIGS. 9A,B). In contrast, 216AA mutant mice treated between P3-5 with a single dose of 2'MOE-29 (SEQ. ID No. 33) had normal audiograms with the expected 4-5 peaks and normal thresholds to BB and 8 and 16 kHz pure tones comparable to wt/het control mice, (48 (BB), 46 (8 kHz), 47 (16 kHz) dB SPL 216AA 2'MOE-29, n=12; 37 (BB), 39 (8 kHz), 38 (16 kHz) dB SPL wt/het ctl, n=16) (FIG. 9B). Thresholds to 32 kHz in 2'MOE-29-treated mutants were slightly lower (88 dB SPL, n=12) than control mutants (>90 dB SPL, n=11), however were considerably higher than wt/het ctl thresholds (51 dB SPL wt/het ctl, n=16) (FIG. 9B). These data show rescue of low and mid frequency hearing and to a lesser degree high frequency. 216AA mutant mice treated with a single dose of 2'MOE-29 (SEQ. ID No. 33) at P10 had more variable responses with higher thresholds than those treated at P4-5 (78 (BB), 72 (8 kHz), 73 (16 kHz), >90 (32 kHz) dB SPL, n=5), but lower than untreated mutants or mutants treated with 2'MOE-C, indicating a developmental window of therapeutic efficacy in mice.

Figure 9C:
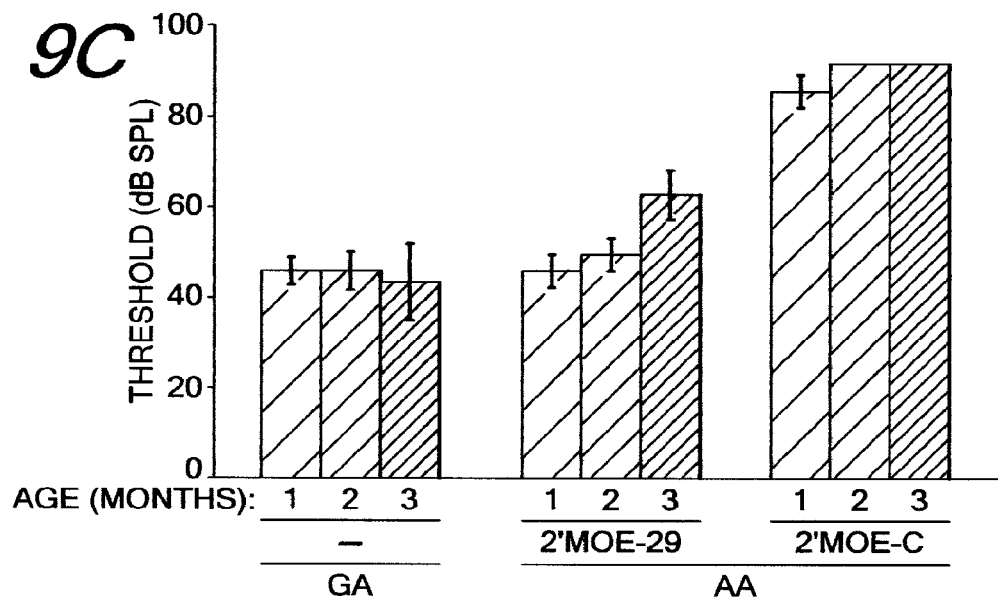

ABRs were also performed at 2 and 3 months of age to determine the duration of auditory rescue. These results show that the mice injected between P3 and P5 of age and to a lesser extent at P10, can hear at 1, 2 and 3 months of age, indicating an effective correction of deafness with a single ASO-treatment early in life (FIG. 9C).

Figure 9D:
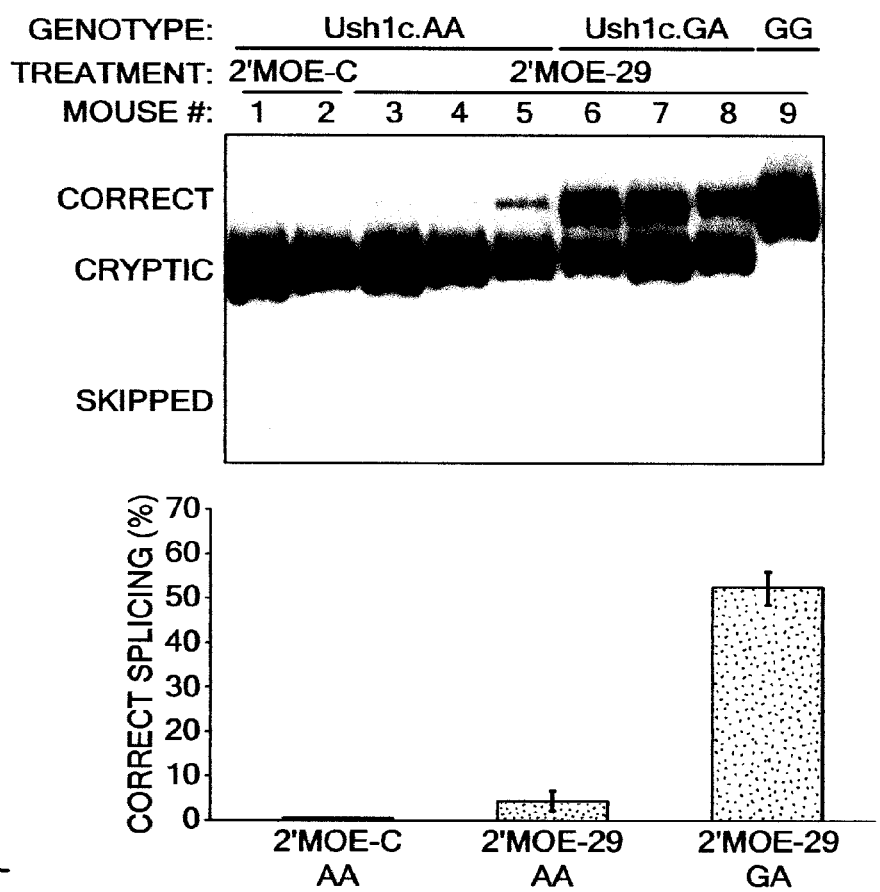
Figure 9E:
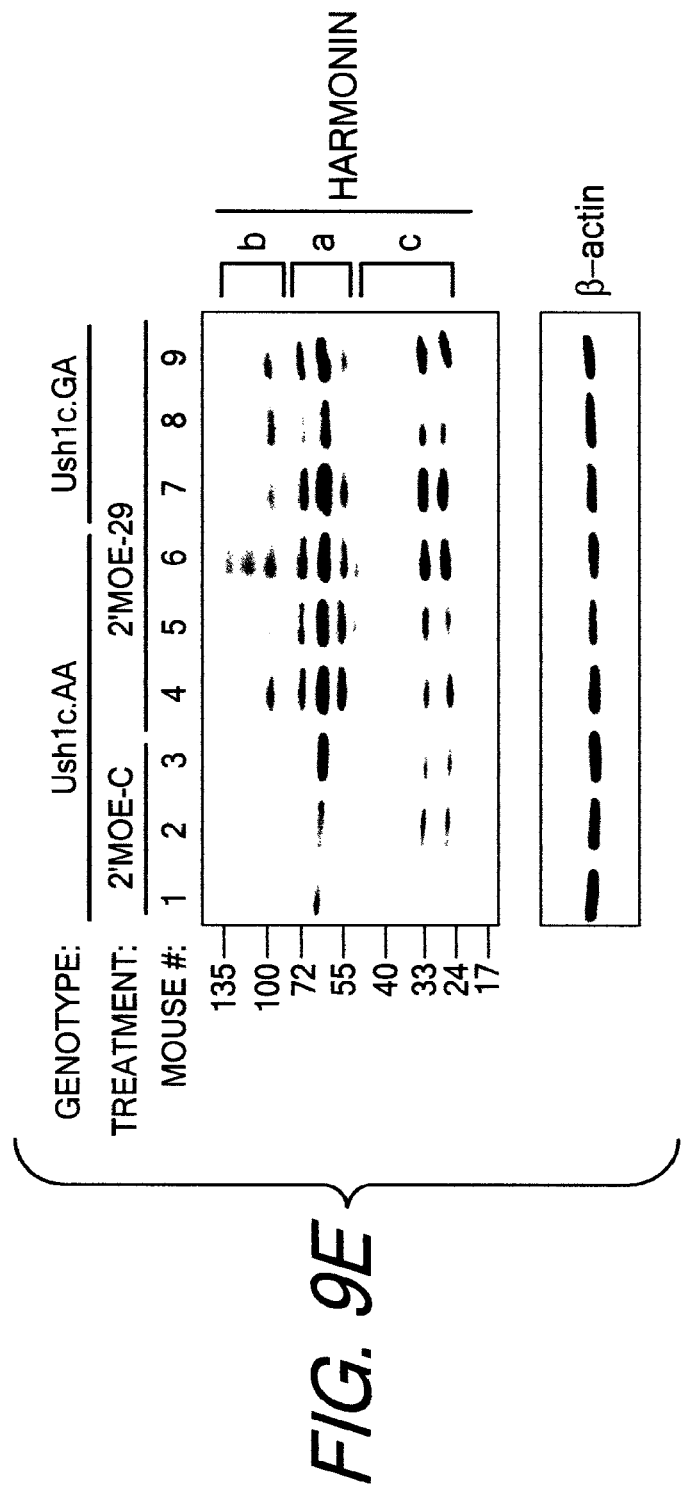

Cochleae from mice injected at P5 with 2'MOE-Ush-29 (SEQ. ID No. 33) or 2'MOE-mis, were harvested at 1 month of age and subjected to RT-PCR and western blot analyses (FIG. 9D, 9E). A low level of correct exon 3 splicing was observed in the 2'MOE-29-treated 216AA mice that was not seen in the control treated mice (FIG. 9D). The correction was not at the level of correct splicing observed in unaffected 216GA mice. It is likely that the extent of splicing correction was greater immediately after treatment when the ASO would have been at the highest concentration during a critical time-period for cochlear and vestibular hair cell development. Harmonin protein levels in cochleae isolated from 2'MOE-Ush-treated mice were higher than that from mice treated with 2'MOE-mis mice and similar to protein levels of 216GA mice (FIG. 9E).

Cochleae were also microdissected harvest organs or corti and subjected to immunohistochemistry. The microdissected organs of corti labeled with DAPI (blue), parvalbumin (red), and neurofilament (green) show the physical structure of the cochleae were consistent with wt/het control mice.

Discussion

Our results strongly suggest that we have cured deafness in Usher syndrome using a single injection of ASO shortly after birth. This indicates that genetic forms of deafness can be effectively treated and that this treatment may only need to occur once in life, during the critical hair cell developmental period.

The correction of hearing in Usher syndrome demonstrates that deafness can be treated if interventions occur at an early time point in development. In mice, our results show that treatment at P10 leads to correction of vestibular dysfunction and partial restoration of hearing, whereas treatment at P3-P5 results in mice that have no vestibular deficits and have ABRs that are nearly identical to wild-type mice. Although harmonin is expressed as early as E15 in mice[4] our results suggest that expression between E15 and P5 is not required for the development of low and mid-frequency hearing. The only quantifiable difference in 216AA mutant mice treated with Ush-2'MOE-29 and 216GA or GG mice is hearing at high frequencies (32 kHz, FIG. 9b). Because detection of high frequency sound occurs at the base of the cochlea, this result may suggest that Ush1c is expressed tonotopically during development, and when treated at P3-5, splicing is only corrected in the mid-apical regions of the cochlea.

Individuals affected with Usher syndrome suffer a tremendous burden from the dual sensory loss of hearing and vision, and the correction of one of these sensory deficits will have a significant positive impact. The retinitis pigmentosa associated with Usher syndrome is recapitulated in the Ush1c.216AA mice, however, retinal cell loss occurs at approximately one year of life in these mice[5]. Thus, our analysis of these animals will require further investigation at later time points. Correcting the molecular defect in the 216AA mice will not only provide a potential therapy for individuals with this particular mutation, but could also help advance the development of therapies for additional disease mutations that involve pre-mRNA splicing. Notably, more than 50% of the genes associated with deafness are caused by mutations that alter pre-mRNA splicing.

Methods Summary

Cell Culture.

A plasmid expressing a minigene of human USH1C 216A exons 2-4 and 2'MOEs were transfected into HeLa cells using Lipofectamine 2000 (Invitrogen). Forty-eight hours after transfection, RNA was isolated and analyzed by RT-PCR with primers to plasmid sequences flanking exon 2 and exon 4.

Mice.

Ush1c.216A knock-in mice were obtained from Louisiana State University Health Science Center (LSUHSC)[3] and bred and treated at Rosalind Franklin University of Medicine and Science (RFUMS). For ABR analysis, mice were shipped 1-2 weeks post-treatment to LSUHSC. All procedures met the NIH guidelines for the care and use of laboratory animals and were approved by the Institutional Animal Care and Use Committees at RFUMS and LSUHSC. Mice were genotyped using ear punch tissue and PCR as described previously[5]. For studies in adult mice, homozygous Ush1c.216AA mice (2-4 months of age) were injected intraperitoneally twice a week for two weeks. RNA was isolated from different tissues using Trizol reagent (Invitrogen) and analyzed by radioactive RT-PCR using primers musUSH1Cex2F and musUSH1Cex5F of the Ush1c.216A transgene. Products were separated on a 6% non-denaturing polyacrylamide gel and quantitated using a Typhoon 9400 phosphorimager (GE Healthsciences). For studies in neonates mice, pups were injected with 300 mg/kg of 2'MOE ASOs at P3-P5 days of age by intraperitoneal injection. After ABR analysis, animals were euthanized and tissues were collected.

mRNA Splicing and Protein Analysis.

Inner ears were isolated, cochleae and vestibules separated and immediately frozen in liquid nitrogen or stored in Trizol reagent. For western blot analysis, proteins were obtained from homogenization in a modified RIPA buffer[10] or isolated from Trizol reagent (Invitrogen) according to manufacturer's instructions. Proteins were separated on 4-15% Tris-glycine gradient gels, transferred to membrane and probed with USH1C (Novus Biologicals) or β-actin (Sigma Aldrich) specific antibodies. RNA was isolated from different tissues using Trizol reagent (Invitrogen) and analyzed by radioactive RT-PCR using primers musUSH1Cex2F and musUSH1Cex5F of the Ush1c.216A transgene. Products were separated on a 6% non-denaturing polyacrylamide gel and quantitated using a Typhoon 9400 phosphorimager (GE Healthsciences).

Behavioral Analysis.

Mice were placed in an open-field chamber and behavior was analyzed using Anymaze software.

Auditory-Evoked Brain Stem Response

Hearing thresholds of treated and untreated Ush1c wt, het and 216AA mutant mice were measured by auditory-evoked brain stem response (ABR). Mice were anesthetized ((I.P. ketamine, 100 mg/kg; xylacine, 6 mg/kg) and body temperature was maintained near 38° C. with a heat pad. All recordings were conducted in a sound proof room. Stimuli consisted of 5 ms pulses of broad-band, 8-, 16- and 32 kHz, with 0.5 ms linear ramps. The stimuli were broadcast through a Motorola piezoelectric speaker (Model No. 15D87141E02) fitted with a plastic funnel and 2 mm diameter tubing over the speaker front, producing an acoustic wave guide which was positioned in the external meatus approximately 0.5 cm from the tympanum. Using continuous tones, stimulus amplitude was calibrated at the end of the tubing with a Bruel and Kjaer 2610 measuring amplifier (fast, linear weighting), 4135 microphone (grid on) and 4230 pistonphone calibrator. All stimulus amplitudes were dB (SPL; rel 20 μPa). Total harmonic distortion was −40 dB (Hewlet Packard 3562A Signal Analyzer). Stimuli were generated (195 kHz srate) and responses digitized (97.7 kHz srate) using TDT System III hardware and software (Brainware). ABRs were recorded with a silver wire (0.03 o.d.) placed subcutaneously behind the left ear, with indifferent and ground electrodes (steel wire) placed subcutaneously at the vertex and hind-limbs, respectively. Responses to 5 msec broad-band, 8-, 16-, and 32-kHz tone bursts were recorded. After amplification (60 dB, Grass P5 AC), filtering (0.3 Hz-1 kHz; TDT PF1), and averaging (n=124-1024), thresholds (+/−6 dB) were determined by eye as the minimum stimulus amplitude which produced an ABR wave pattern similar to that produced for the highest intensity stimulus (90 dB).

Immunofluorescence

Fluorescent labeling of microdissected whole-mount preparations of the organ of Corti were used to study the cochleas of one month old treated and untreated mutant and control mice as described previously[13]. Briefly, cochleae were isolated from the auditory bulla and a small opening was created in the apex. The stapes was removed from the oval window and the cochleae were gently perfused with 4% paraformaldehyde in 0.1M phosphate buffer, pH 7.4 and post-fixed by immersion for 2 hours in the same fixative at 4° C. Segments (half turns) of the organ of Corti were carefully dissected free from the cochlea, the stria vascularis was pulled off or trimmed down, and the tectorial membrane was lifted free with fine forceps and discarded. Tissues were washed twice with PBS following fixation and processed for immunohistochemistry. Tissues were incubated for 1 hour at room temperature in a blocking solution consisting of 10% normal goat serum/0.03% saponin/0.1% Triton X-100 in PBS in order to reduce non-specific binding of primary and secondary antibodies. Primary antibody incubations were then performed at 4° C. in PBS containing 0.03% saponin, 3% normal goat serum, 2 mg/ml bovine serum albumin, and 0.1% Triton x-100. A mouse monoclonal anti-parvalbumin antibody (parv19, Cat. No. P3088, Sigma, St. Louis Mich., 1:500; Sage et al., 2000) was used to label cochlear hair cells. A mouse monoclonal anti-neurofilament 200 kDa antibody (Cat. No. N0142, Sigma) was used at a dilution of 1:500 to label nerve fibers (Hardie et al., 2004). A rabbit anti-harmonin antibody (Ush1c, Cat. No., Novus) was used at to label all isoforms of harmonin. To detect the presence of Ush-2'MOE, and anti-Ush-2'MOE antibody (Isis Pharmaceuticals) was used. Secondary antibodies conjugated to Alexa 488, 568 or 633 (Invitrogen/Molecular Probes) were used at a dilution of 1:200 in the same buffer for 2-4 hours at room temperature. For mouse antibodies against parvalbumin, the M.O.M. kit was used as specified by the manufacturer (Vector Labs). Tissues were washed (3 times for 10-15 min. each) after primary and secondary antibody incubations in 0.1% Tween-20 in PBS. After counterstaining nuclei with DAPI (Cat. No. D9542, Sigma-Aldrich, 1 microgram/ml) or Sytox Green specimens were mounted in Fluoromount-G™ (Cat. #0100-01, Southern Biotech, Birmingham Ala.), coverslipped, and examined by confocal fluorescence microscopy. Preparations were examined with an Zeis laser scanning confocal microscopic equipped with 405 nm blue diode multiline argon laser (457 nm, 488 nm and 514 nm), 543 nm helium neon laser, and 637 nm helium neon lasers. Sequential image acquisition was performed when bleed-through between channels was an issue. Files were imported into Image J and/or Adobe Photoshop for processing and analysis.

REFERENCES

1 Morton, C. C. & Nance, W. E. Newborn hearing screening—a silent revolution. *N Engl J Med* 354, 2151-2164, doi:354/20/2151 [pii] 10.1056/NEJMra050700 (2006).
2 Kral, A. & O'Donoghue, G. M. Profound deafness in childhood. *N Engl J Med* 363, 1438-1450, doi:10.1056/NEJMra0911225 (2010).
3 Lentz, J., Pan, F., Ng, S. S., Deininger, P. & Keats, B. Ush1c216A knock-in mouse survives Katrina. *Mutat Res*

616, 139-144, doi:S0027-5107(06)00320-4 [pii] 10.1016/j.mrfmmm.2006.11.006 (2007).
4 El-Amraoui, A. & Petit, C. Usher I syndrome: unravelling the mechanisms that underlie the cohesion of the growing hair bundle in inner ear sensory cells. *J Cell Sci* 118, 4593-4603, doi:118/20/4593 [pii] 10.1242/jcs.02636 (2005).
5 Lentz, J. J. et al. Deafness and retinal degeneration in a novel USH1C knock-in mouse model. *Dev Neurobiol* 70, 253-267, doi:10.1002/dneu.20771 (2010).
6 van Ommen, G. J., van Deutekom, J. & Aartsma-Rus, A. The therapeutic potential of antisense-mediated exon skipping. *Curr Opin Mol Ther* 10, 140-149 (2008).
7 Hua, Y. et al. Antisense correction of SMN2 splicing in the CNS rescues necrosis in a type III SMA mouse model. *Genes Dev* 24, 1634-1644, doi:gad.1941310 [pii] 10.1101/gad.1941310 (2010).
8 Goemans, N. M. et al. Systemic administration of PRO051 in Duchenne's muscular dystrophy. *N Engl J Med* 364, 1513-1522, doi:10.1056/NEJMoa1011367 (2011).
9 Hastings, M. L., Allemand, E., Duelli, D. M., Myers, M. P. & Krainer, A. R. Control of pre-mRNA splicing by the general splicing factors PUF60 and U2AF(65). *PLoS One* 2, e538, doi:10.1371/journal.pone.0000538 (2007).
10 Hastings, M. L. et al. Tetracyclines that promote SMN2 exon 7 splicing as therapeutics for spinal muscular atrophy. *Sci Transl Med* 1, 5ra12, doi:10.1126/scitranslmed.3000208 (2009).

From the foregoing, it will be observed that numerous variations and modifications may be effected without departing from the spirit and scope of the invention. It is to be understood that no limitation with respect to the specific apparatus illustrated herein is intended or should be inferred. It is, of course, intended to cover by the appended claims all such modifications as fall within the scope of the claims.

I claim:

1. A modified oligonucleotide comprising at least 19 contiguous nucleobases of SEQ ID NO: 2 or SEQ ID NO: 3.

2. The modified oligonucleotide of claim 1, wherein the oligonucleotide is chemically modified to be different from a naturally occurring oligonucleotide with the same sequence.

3. The modified oligonucleotide of claim 2, wherein the naturally occurring oligonucleotide with the same sequence comprises a sugar moiety, a base moiety, and a phosphodiester linking group and the chemically modified oligonucleotide has a different sugar moiety, a different base moiety, a different linking group, or combinations of any of these modifications.

4. The modified oligonucleotide of claim 3, wherein the chemical modification is to the sugar moiety.

5. The modified oligonucleotide of claim 4, wherein the sugar moiety in the naturally occurring oligonucleotide is a ribose sugar and the different sugar moiety is a morpholine ring.

6. The modified oligonucleotide of claim 4, wherein the sugar moiety in the naturally occurring oligonucleotide is a ribose sugar and the different sugar moiety is a furanosyl.

7. The modified oligonucleotide of claim 6, wherein the furanosyl has chemical substituents to form bicyclic or tricyclic sugars.

8. A modified oligonucleotide comprising SEQ ID NO: 2 or SEQ ID NO: 3.

9. The modified oligonucleotide of claim 8, which consists of SEQ ID NO: 2 or SEQ ID NO: 3.

10. The modified oligonucleotide of claim 8, wherein the oligonucleotide is chemically modified to be different from a naturally occurring oligonucleotide with the same sequence.

11. The modified oligonucleotide of claim 10, wherein the naturally occurring oligonucleotide with the same sequence comprises a sugar moiety, a base moiety, and a phosphodiester linking group and the chemically modified oligonucleotide has a different sugar moiety, a different base moiety, a different linking group, or combinations of any of these modifications.

12. The modified oligonucleotide of claim 11, wherein the chemical modification is to the sugar moiety.

13. The modified oligonucleotide of claim 12, wherein the sugar moiety in the naturally occurring oligonucleotide is a ribose sugar and the different sugar moiety is a morpholine ring.

14. The modified oligonucleotide of claim 12, wherein the sugar moiety in the naturally occurring oligonucleotide is a ribose sugar and the different sugar moiety is a furanosyl.

15. The modified oligonucleotide of claim 14, wherein the furanosyl has chemical substituents to form bicyclic or tricyclic sugars.

* * * * *

SEQUENCE LISTING

```
<160> NUMBER OF SEQ ID NOS: 64

<210> SEQ ID NO 1
<211> LENGTH: 57522
<212> TYPE: DNA
<213> ORGANISM: Homo sapiens

<400> SEQUENCE: 1
gaagcacgcc cacaccatcc ccctcactc caccttgggg tcttcatgtc tatttccaaa      60
gggcaggagt tgggactcat tgctgtcata aacgattctc cccaatctgc tggctcaagg    120
ggctccccag agctgaccgc tggggctggg gcaggggcac ttgagctgag gctcagctgc    180
tttgggggac ctagctgcag gtgggtggaa cttatagctc atctgtagtt atagaaagag    240
ggagacaaat gcgggccagg attagaaagt agacctgagt cacctgatcc agagaccaaa    300
gaagtttggc aaagggagaa aacaaaactg ccacctctcc cacaaacaca gaggaccgtg    360
ggaagatggg cagtggaatg gtcaagactc aaaggataga ggccgggctc agtggctcat    420
gcctaatccc agcactttgg gaggctgaca cagaaggatc acttgaggcc aggagttcaa    480
gaccagcctg ggcaacatag tgagactctg tctctaccaa aaaaattgaa attcaaccag    540
gcatggtggc acacacctat agtcctagct actcaggtaa cggaggcacc aggatcactt    600
gagcccagga agttgaggct gcagtgaact atgattatgc gactgcactc cagcctgtgt    660
cacagagcaa gaccccgact caaaaaaaga aaaaaaaagg ctcaaaggat gagttcaggg    720
ctctgcttct caaccaaacc ttccttgcaa cttccaccag gtggcctagt ttttgtcttg    780
cctgcattct tgaggctccg ctcagggtat ggagaggagc ctctgacagg gttgagggcc    840
ttcgcaggcc agtcagggaa aagagaactc cattcttcta aacgtccatc tttctacttt    900
tacctgccag aaggagagc tcagctctct cctgaaagag ccctggtgcc cacctctcct    960
aaaaaaaaaa aaaaaaaaa aaaaaaaaaa aaaaaaaga gtggactata gacccccaag   1020
agattaaaaa gaatagaagg gttttatgaa cttgcacacc tcagacacat accaggaatc   1080
tgcttgttcc tttctgaaca actccagaga cccctcctgt aacctacaga gctccctgcc   1140
agcctcagat ccagatagac atgagctcct gctcaatgaa gcccctcc aagacctccc     1200 ttacctggcc tcccacgact gtagccttgt ccccatggc aagggtcgcc tcctggtggc    1260
tgctgctgga ggaaacacga gtctggcatg gatggggggc taggatgggt tatgcctccc   1320
cgcagtcccc tggcctatcc caccctaagt gctaaagccc tggggtcgct gatgccagaa   1380
```

```
atacggatgg gagctgtggg tggggccgcc acagctcaca cctactcacc tgggttgccc    1440
ggctggctct ggctgtggct ctgcactgcc ccacagaacg ggtgctgcgg ctggggaggg    1500
ggattattct ccactcaaat tgtgcttgtc tttactgggg cctcccacca cctggccccc    1560
actgctagaa agcctctccc acgccactga gcattccccc attctccctc cctgcagcct    1620
tctcaaatcc tttctctccc ttcctgatga cccttctcca gccaggatct ccctgtttac    1680
tctcagtctt tggcccccag ctctctctag ttccccacct cgggtctctt ccacccagcc    1740
taactttgga ctcttttccc cgcggtcata ggcctgcctc tgttggcttc ggggtccctc    1800 ctccctgac tgctcctcct gggtgtccct ctgctctccc tcaaacctct ctttcctccc     1860
tctctccaac ctgcgcgggc ccattcctca ttcctttaac gtttctcatt cctcgagccc    1920
ccgacctccc tgagtccaca accctctcac cgaggcgctg cacccgcagg gactcggctg    1980
cctgctcacc ccagggcagc cagacacaaa gcagccagca gagcgcagac gccaggactc    2040
ccatagggac acgaggggac cggaggactt gagcgcaggg ccagcctccc gaggtgcctc    2100
cccgggctaa ggcagggtca cacctccact ccgcagccga ggtccctctt gttctcatgc    2160
cccagggctc cctcagcccc tcctcccagg ctctcagctc ctccccgaac tagagtgaca    2220
ggagtaccca gcttattacc ataatttagg cgcctgtcca tagcctagcc tctgcttttc    2280
ttggcctgtg gccacacctc cccaggggag gctggattca gattactcag ccctaaattg    2340
tctagggaag catagaggca gcctatgcaa cctccagctc cccttacctg ggtcctggaa    2400
gcccaatacc agagacgcaa gatgcaggta tgagtctggc cctatcctct ccttttacag    2460
agggccatgc tgaggccctg ggacatgcca ctcaggatc agtggtcaat aacagagcct     2520
gcagagtcct agcctatgtt ctcaccatgc cccacctcag cttccacctg ggtctccaca    2580
tccgtatcct atgaccagtt ttgagcacct ctagggaatg gatcatgcct tagtcctctg    2640
aatgcccagc accagctcct gcccgagctc aggaaatgac gattgaataa taaaagtgtt    2700
tcatactcct atgttattgc caccatcaag gccaaacttt gacaaaacaa ctttatatgt    2760
gtgaacgagg tccactgtct gcccaggagg aatttaaaaa tggcaaaaac atgggactga    2820
gcacctgggg aatctgtaca tcattcactt cgtcatcact tagggaacac caactagatg    2880
ctaggtctta cagaggatga tgatgatggt ggtggtggtg gtcgtggtgg tattggcccc    2940
agtagacttc taggcaaggg tatagatttg agatgcattc attcattcat tcattcattc    3000
attcactcaa caaatttgtt tggcattgat tccatgccat gcactgttct aggcatatag    3060
tggtaaataa agcaaacaca gctatcttca cacaggagga agctgggggc acagatagga    3120
agatgaagag gaaagagcta aggatggagc cttaaggaat gctggttaag gaacaggcaa    3180
agactgattg tctccaagga agcttgaaac aaaaattcat gagagaggag aaccaggtct    3240
caatgctatt ctcaaaacaa agcagggggc attttaaggt ggagggagtc tgtgggggta    3300
atggccaatg taaataagg attggtgtgg caggtgaaca gcattcccct ggataaggac      3360
attcattcac ctctgccagg attctaaata caaaataaac agccatatga cattcttttc    3420
caatgtagag aatcaatgaa gtaagtcgga ggggaatgca ttttgtgtgg cctttttctgg   3480 accattcaaa aatcccacaa gtcttttccat tttatcgctg acttaatagt taatgctaag   3540
gtgagaaaac agatcatatt ttaaggttct tctccaagag ggatttacat cttaaactag    3600
gcaacaaaaa tagtgtgctt gtaaaacttc agctattggg gagagggacg cagagggggtg   3660 tttaggtgcc ccagagttac aattgtaagt ggttacctga tgtaagctgc tgtccatctc    3720
cttgcccctg cccttgacag ggcacaaagg gctcaggtgc ctccctgggt taagttcagg    3780
```

-continued

```
cacaagcccc atacttagcc tctgatttac acatttttat cacccctctc ctagcccctc   3840
tttcctttca tctctttcca ggcctggttc atcattgtct ttgatgaatc tttcctttca   3900
ttcctttcca ggcctggttc atcattgtct ttgcaccaag cactagacct aggagttaag   3960
caaatgctga ccaaattgaa ttaaatgaac cagagggtct gggccctggg tgaaggtcag   4020
ccatagatca aaatgtcact gccaggctct gccaggcttc gatggatatg tgagtgtgtt   4080
gggtttgggt tttgttttgt cttgttttgt tggggtgga ggtgttaggg aaggtgggag    4140
gggaaatcag ttgaggggg cactctcaca cacactgatt cagaccctg cggcccacag    4200 taaaacccag ccctgtcccc aaggaattca cagaacaagg attgatttct ccctggtgga   4260
aaagtgcagg aggaagccag gactgaaggt acgctggagg tgagggcgta caagggctg    4320 acagtccagg agggccatga acctcgacaa gagtatccag agaaggccgg gcgcggtggc   4380
ccgcgcctgt aatcccagca ctttgggagg ccgaggtggg cagatcacga ggtcaggaga   4440
tcgagacctt cctggcgaac acggtgaaac cccgtctcta ctaaaaatac aaaaaaaaaa   4500
aattagccgg gcgtggtggc gggcgcctgt agtcccagct actcgggagg ctgaggcagg   4560
agaatggcgt gaacccggga ggcggagctt gcagtgagcc aagatcatgc cactgcactg   4620
tagcctgggc gacagagcga gactccgtct cgggggggaa aaaaaagaa tatccagaga   4680 aaacggacta gattgccccg cccccgcc gtgtaaatag tttccgtatc tctctattcc    4740
ggtccccaca aaaagtccc aaacctcctc cctacgtctc cacgatcttc ttcctcaaac    4800
gcatgtgttc aggtaccact tccagagaaa taccagcttg aagcccagct actgccacct   4860
caggcccata ggcacactgg ggcccatttg ctcccaggct tcagtgggag gcgacgactc   4920
agcaccttcg actccagcct cgcagcggcc ccgccccaca gaggcctggc cccgccctc    4980 cgcgctcagg cccgccccc agctccgagg gcggctggcc cggtcgcggt cgcggctctt   5040
tccagctcct ggcagccggg cacccgaagg aacgggtcgt gcaacgacgc agctggacct   5100
ggcccagcca tggaccgaaa agtggcccga gaattccggc ataaggtcag agctgcaggg   5160
cgccccaggc ttctgggact ccggagtcct gggcgcggtg ggtaggggt ggacaccccg    5220 gcactgcccc tccctttcc ggccccacct gatggctctg gttgggctgg gacacccgag    5280
ggtcgtctgg ctggcagcag ggatccccag taaagtgagg gagggaatgc ggggactccc   5340
ggctcaagga ctgctaaacg agtcgatctt ctgccagcct ttctccctct gccttccagg   5400
ggcagggacg tctctggggt ttgaattcct tccagtcttg gccgctttc tgaggtgccc    5460 cctttgtggg caagcccctc tccttcctag tgccccagc tcaggctgt tgaggcatgt    5520 ggagacagtc tggggcagta tctgagaggt gagggttggg agaagggaaa ctagacgtct   5580
ctctctctgc cttttgacct cagaacatga gttagaagca tttcagccct gcctgcctaa   5640
gggcgtttct tagggtctga gaagtagctg aggagctggt gctgacccgg gtgcggtggg   5700
gaggaaggga ggaggtactg agggcgtcgg agctgggctc tggccggcca gatccttcag   5760
gcagagccgg gtccaccctg gtgtgtccca gtgagggcc tcactggtgg tctgggattc    5820
tcaaggacca tctctggaag tggccaggtt tcacacaggg catttcgaga atgattcaca   5880
aagctgtgca gaatctgctg aggccctgag accagagagg gccatcaaag agatccagcc   5940
tacttcccca ccaagtctta ggatgcctct gagtctgggg atgaagccgc ttggggggg    6000 tgggtggtat ctggagctcc ccacaggccc tgcctgaggg gcaggtaact attgataact   6060
taactattga taactgtgtg acccaaggct ctcccaaaga ccccaggggc agtgtctta    6120
```

```
gaccaagcca aacctcttcc tggtttgaga gctgagctca ggtagggcag gtcagggtgc    6180
ttaactcctt ccttcccata aagaggccca taggagccca aggagctagc cagtgtaggg    6240
gccacagggg cttggggcca agggcccggg gtcagttatt catttaataa gcatgttttg    6300
agcatcctct cagccatacc cagtctgtgc cctttgctgg tggtgtaggt gggaggcaga    6360
ccctaccctg gtaattaccc atgtctgagt gctgcgtgtt gaggccaagc ttttgtaggg    6420
gcacaagggg acagctcaaa ctggcagaag gctcctgaaa acaaggtctt gggcatttct    6480
ggtcctgctc ccaggggtgg gtgatagctg gaagttcagc aggaatttag gggctggcga    6540
ataccaaggg gagcttgaga gagcattcac tgttacatcc tgttgcaaag agacatgtcg    6600
gaagaaattt cagccactaa ggacattttg tgagtgtaga tttcaggcaa cccagtttga    6660
aggagctcag ccttccatcc cccaacccaa gactcagggt tgaatttcag tttcctgccc    6720
ctggcctgaa ataacatcag gtcttctgcc ttcactctgt ggggtacctg ctctctcttt    6780
tttgtgagaa tcatctccag ggtccctggt gtctgatgca gatcctgggt ttgccctgtt    6840
cctcttcccc aggtcccaca ggctccaaag ggcctcagac ctccacgttt cctctgccct    6900
actcttcctc atcgcaacag tcattactta ttaatatccc tgtgtgcagg cagggcaggc    6960
gccatgcgct aggcaaggcc caggctggac tttgtgccct gctgccttgg agacagccac    7020
agccttcccc tcccaggttg gggatcatcc aggaactggg gagagaggat gaagcacaga    7080
ggatagaaag gaggcacaca gacatgctgg gagaaattta cagcttgctg ttgtttgctt    7140
tgtaggggtc ccttccttag tgttttggaa gaaatggttt gtgatctaaa tccttagttg    7200
ttggaagtaa tatttaaggt agtgtgttat aatggaaagt gctctgtgac cttgagcaag    7260
ttacttaatc tctctgtgcc tcagtgctct tacttgtgaa aagagataac aatatttaac    7320
gaataaggtt accatgaatg ctgaatgaga cctacatgtg tgtggggagc ttaaatagac    7380
cctggcactt agggagctct caagaaatgt ccatgttgat tattatctgg agttagcaga    7440
actgggacca aatcttagcc ctgtcactgt caggaagacc ttgaccaagc cacccactct    7500
ccctgagttt tagttttcttc agctatgaga tggagtttgt agaacttacc tcacaagaca    7560
gtcaaaacta actagcaatt aaagtactgg ctgctctggg cccacagtaa ccacactgtt    7620
tccagctgat acctgcagag tgtccagtgg gagccaacag gctccaggca tcgactccct    7680
ttgatttgtg aagttacccc aaggccgcca ggagcacttg catacccttc cagtaactag    7740
tagcaacctt gggccaggat gtgggggagc agggcttggt cagagactgt tttctccctc    7800
agagaaccag ctttcaaagg gagactgctc ttctgttcgc agcaccagca cagggtagga    7860
acttggttac tcattggctt aaaagtattt attgcctctt cagcaatcat gcatttatga    7920
gcatagctgt gtattctgcc tgaggccagg catctgacaa ccggttggga tgaataagat    7980
cagaaagagc caccactctc taggaatttg ttaatcattc atttattcac ataggcaata    8040
aatattgact gagcccttaa tatatgccag gcagtactct aagcatcaaa aaacaaaata    8100
aagcccttgc tgtcttagac agtacattcc agtagggaag acaggtagtt aaaaggaaat    8160 caacaaagt atcatacaat gccagatagt gataaattct atgaaaaaat aaactaagat    8220
ggggagagag agatagtaag tgacaaggta ggcagtcacg aaggcctctc tgaagaggtg    8280
acatctgagc agagacctag aagaagtgag gagaaggagc cacagagata catgtagaag    8340
agcattccct aaagtggaag caacaagtgt gaaggccctg aggcaagcag atgcccgcct    8400
gtatggaaca gcaagtagga cagtgtgtcc cagaggaatc gtgagtggag aatggtgaga    8460
aatgggtcgg aggggtggta ggggcctggt aggccatggt caggtcagga ttttcttgta    8520
```

```
agtgtgaatg atttacattt aaaaggaatt gttctggctg ctctgtagag aatccactga    8580
ggggcccaag agtagaaggg gaccctcagtc aggaggctcc tgcaggagcc caggccagag    8640 gcagggctc ggactcgggt gagaatgggt cggattcagg atacatgtta aaggaaaaac     8700
tgacaggctt tgctgatgga ttggctgcga gcgtagaaag agaggcatca aggtgaatc     8760 cacatttggt ggagacggag caggttggtg gagacggagc aggaggtggt ggaaacctag    8820
cgttccactt cgaatgctgt aagtttgaga cgcctgctag aggtgactga gaaggctgta    8880
ggtctggcct ggagataagc atcggtaggt ccttgggggt gtgagtggta tttaaacccc    8940
tgagatgaat gaggtcactt agagagacag tgcagatgga gaggagacct aggacagagc    9000
ccggggtacc tcaacttttg gaggagaagg agcagcaagc gaggaaggaa agcaaggaga    9060
agcagggcgt gattgctgtg ccaggcacag ggtgaaatac tacaaactag ctgacatgtc    9120
aagagcctct gaaaagatga agggcactgt ctatgtcctt gatggtggtg atgctttcac    9180
acgtgcacat ttatcccccaa actcatcagg ttgtatacac taaatatata cagcgcttta   9240
catgtcaggc atacctcaat aaagtggttc cagaaaaaga aaagaagtca ggtgtggcgg    9300
ctcacgcctg aaatcccagc attttgggag gctgaggtgg gagaatcact tgagtccatg    9360
agtttgagac cagcctgggc aacatagcga acccccatct ctacaaaaaa tacaaaaatt    9420
agccaggtgt ggtgttgtgc acctgtagtc ccagctactt gagaggttga ggcaggagaa    9480
tcaattgagc ctggaggttg aggctgcagt gagctgtggt cacaccactg cactccagct    9540
tgggtgacag agtaagacct ggtctcaaaa aaaaaaaaa aaagaaaaag aaagaaacag     9600
aaacagaaag aaagaaaga gagagagaca gagacagaga cagagagaac cctagacaag     9660
aaagaaagaa agcaaaagaa aaagaaaaga tggatgataa gaaaatgaga gtcaaataaa    9720
gcctggtacc actgggatgc acactctaaa ggcctgggaa gaagtgtggc tggatctatt    9780
catcccacta acatctacag agggccactc gctgcccact gctgtggata tagaatttat    9840
gtccacttat tgtcacttag ttttatgtaa caaacacagg acttactacc tgccaggcac    9900
tgttctgaac tcttcataat tattaactca ttaaattaat actaaaaaac aatgattaat    9960
ctctcatagt gattaaatcc cattttaaaa agagatgtta gtcctcattt tacagataag   10020
gaaactgagg cacagagagg agcagaccca gttgggaag gggttctttg gctctaccac    10080
cacactcaca agccaggcct gtgtctgggc cacacacagg cttgtgggga gacaggaggg   10140
taaagggaga aagttcagca cagcttggtg agtcccatgg cagagttggg gacaaagtgc   10200
tgttgtgtgc acagagaaag atgtggccag cttttgtgtgg gagcctaagg aaaagacttgg  10260 ccaagaagag gcgacatttg aagtgagtct taaagataga ggaggagtcc acagagagga   10320
aatactgctg gtaccaccat tgctaatggc taaccagggt ggcagcaggg agcaggtggc   10380
tcgtccaagg gggaagccaa gaaagcttta tgaacaggtt ctacagaaaa gggcaggatt   10440
aaatgaccca acaagctgca ccctgggggcc agatgcagga ggccagcatc cctgaagggg  10500
ccagtagagg gaaggttacc agaacaggtg agaaccaggg ctgccaaaga ggcccagaca   10560
gcagctgcag ccttgggtgg aggaacctgc ctaactgtgg cccagcagcc agcccccagg   10620
gactaggagc ctcagttcct gtctccccac gcctctcatc tcctgcttgt gcctcccgat   10680
ggctgaacac agcagaaagc cagagggag aggagcccag gcagagccct ctggacaaag    10740
ggcagggtgg agaaggctgg aggcatgaaa ggaaaagatc tagcacacat tttgagacc    10800 ttgaaatgtc ccaggcattg tcatacgtgc tttacacata ctcactcatt taatccccgc   10860
```

```
aacagcccaa agagacttca tcaagcagaa caacatgcat tatttaattt gttctggctc    10920
tctttctccc tgtttggctg ggtgcacacc taaagttgaa tcttcctgag ttgactgtcc    10980
catggttccc ctgtgtagct atcctgaagg gccagtccat atgggggaat acagagggat    11040
gagactggag ggtaccacat ggccaaaccc agcttttgcc tccaataccc tagacaaggg    11100
gcctgaagat tgtgagggtg gagatgctcc ctgtcccctc ctccctccca cacagaccaa    11160
tagcacagtg ccagagaaac atcagtcagc aaatgctaat ctaggcaggg ctggcagcag    11220
gggcaggggg tagcagggat gataatagag atccccaaca gctatttgta gatggtgggc    11280
tcctttaggg cttctgtgct taatatcaag agggatccaa gaaaggaaa ggctttctaa     11340 atctagtcgg agaaagaaga ctggtgtctt tcccacagta ggtgttcaat agatgtgtaa    11400
tggacaagtg gacaacaaag gagttatatt tcataagtgg ataccatgtg gtagattgaa    11460
aaaaagcaga ggttttggag ccagtaggca taggttgggg tctcaattct gtcacttctc    11520
tgagcctctg tttcctcatc tgtaaagtgg ggatgataac gttcacctca gagggttgtt    11580
aggatattaa agataataca cgtaaagttc ctcaggcagt ggacagtcag tagggagagg    11640
ctggctggga taagtgagcc agacagaaag agactcaggc tgggaggcag gtgaggaggc    11700
tccagactct agaagagggg acttgggcct catctgaaat gaaggcagga ttcagatgag    11760
aggaggaaag ctgtccattg tggatagatg gagtcgctgg gacctacttt tttgtgatga    11820
attggaagtg aactaagggg aggcagaccc agaatatatg tgctgaggac cagtggaaag    11880
gtggtgaccc aggcctgggc caacaggtca gaaagaaggc tctagactag agcaaatga     11940 gttcacgttt catcaacgga cgccactggg caccgtgcgc ttgtgtgcat gacatggttc    12000
tgggttccac agggaaatga agaacatgtt tggaaggaag ggaagaaagg agtgtgggag    12060
atttactgcg tgcctagtgc ttcgtatgta cctgagtaca gggtactggg acaatggtac    12120
aaagcaccct agagcagggg ctccccaaaa ctgatcctcg ggctagtgct aggcagaatt    12180
ccagaagaga ggaaactata taatttttta atattggaaa agtaattga tttgaccac      12240 agggaagact acaaagaaaa agtaatttaa gtgatggtgg tattgttact gcacgttcag    12300
gctttagaga aacttccatc tttctcagct ttctttcctg gtgccttta atgcctgaag      12360 agtgaggtgt gagtgtgtgt tttcactcag gtgtggtcag agaacaaagc agtgctgttc    12420
tttctgagtc tttctgagat attttctgggt gagaatgatc cctccctttg caggatctcc    12480
tgtgtaacca gttttcaagt ttttgatgat ctatcactta gattcatatt taaagagcat    12540
tctacacaaa ccagatctat tttccctgtt agctggtatg gtctatagag aattgtttaa    12600
atagacaagt cagacatggc ggtagatgga atgttctgag tgaggacaag gagattccag    12660
tgtgtcaggg gaaggatctg ttccactgca gctgagtccc acttgggatg tggtgaagcg    12720
agcaatggca gaactgagga cagggtttga gtgacctaac cggtgacagt gggtggacat    12780
gaggccgaag agctgagctc tgcagctgtc tcaggagaca ggtaggatga gacctctggg    12840
agcagtggtc agtgctggag ggctgctgac aagggccagg agcccgggac cttcagggac    12900
aggctccttt ccaccaagac catctccaag tgatctgtgc ttggcccagg gaagggagaa    12960
aaacagaacc ctagacccta acattgcaag ttaccttact cttctacctc agttttccac    13020
ctaatgcaca ataaacatgg tctaaggagg acagttcctc actactgaaa tctaatgcta    13080
cagcaagata catttctgca aagagggata agagggaact tcagtcctaa ggcctcagtc    13140
aataagagat tctctgtccc atcttctttc ttgtgtcacc acccagggtt ataactaggc    13200
tagaagtctt tagtcagggt gtcctctctt cagccaaagc agacgtgatt tttatgctcc    13260
```

```
ccttagaaag tacaacactt gggttcaaag agtcattcaa aagatgtccc attttctcac   13320
tcattataga ccaagccaaa agtgttttct taacagtgca gaggagagag atggggctta   13380
gagataagaa aggagttctt gaaagcaaag ggttggaaat tttggcctaa agggacattg   13440
ggagttattt tccCctgcca ggcctgagtc acaatcaatg gtcatcgtgg cgtagcagaa   13500
agaacatggg ctttggagtc agacttaggt tcatatccta gctctgctta ttagctgtgg   13560
gacactgggt gagttgactt aacctctctg atcctcagtt tcctcagctg cagcattatg   13620
tgagaatatt gccccaatgt gataaacaaa tggaataaag cccatgaaaa gctcctggtg   13680
ccaccgcatg gggcattatg gggacaacat catttccctt cccCttctgt tcccatggtt   13740
acctccctcc cacctgaacc atgtgggcat accaggaggc aggcagataa attcattcaa   13800 tacttctttta ttgagagctt attatgtgtt gggcacgaga aatttagaac aaaatagatc   13860
tcatctttcc cctcatggga ttttttctgtc cagcgaaggt gacagagaaa acaattcaca   13920
gagaaaacaa accttaaatt acaaattgta gtcgatctgt gaaggaattg aaacatctcc   13980
ggggtgcagg agtcggttct gtctgggtag gtgagcaggg aagacctctc tggaaaggag   14040
gtggccaggc agggaagtgg gggaagcagt ccaagcagag ggaacaagca tacgccaagg   14100
ccctgaggct ggagagcgtt cggcctgtgg gaagaactga aaggaggact ttgtagccag   14160
gaagactggt aggagaggag attgggcttt gataagtcaa agtaaggagt ttggatttag   14220
gtttggtttg gggtacaaga aactactgag caagcaagca acatatctaa tttataaaga   14280
tatttctcgc ccctgctgct aggagagttc atactcctcc atcacagccc agtgtgggca   14340
gcccaggcct gtctcaggga ggcacccctg ccccacaggc ctgagcagag ggggtgagag   14400
aatccaggct atgtggagag atgagctttc agaggtggtg ggtgcgaaag gccagcctcc   14460
caccctaaga tttagtacca cccactcaag cagatgcttc catctcctgt catctgggag   14520
ctcctttttt tttttttttt tttgagatgg agtctcgctc tgtcacccag cctggagtgc   14580
agtggtgcaa tcttggctca ctgcaacctc cgcctcccga gttcaagtga ttctcctgcc   14640
tcagcctcct aagtagctgg gattacaggg gcataccact acgcccagct aattttttgta   14700 ttttaataga cacagggttt tgccatgtta gcgaggctgg tctcaaactc ctgatctcag   14760
gtgatctgcc cacctcggcc tcccaaagtg ctgggattat aggcgtgagc caccgcaccc   14820
agccctagct gggaactcct tgcactgagg tagggagaaa gcaagggtgc cttttggag   14880 caggtgggct gaacttctgt agcaactaaa gcccaagctg tgagtcaagc ctcccaagtt   14940
attctcacct ttaatgaaat gctcagtctg atttttatagg gaaggaggta ctgtcagatc   15000
taggccagaa atctgcattc tgtaccccct gctcaggcca gaaatcccaa gggctgggcc   15060
cagcatgtcc cctctgtggt gggacggaca gactgccccg gtcttccaga acccttggaa   15120
tacccacaga aagaggtaac gctgctctgg ccctcttctg aggacgagtc agtggagagc   15180
atgcagcttc cagctgcagc ctctctatga agggctgagg ccctgggccg ggaggctgga   15240
ggagagaggg acccagtgac cccccaagct tccaccttgc tctgttaccc gttcttgggc   15300
tgaagagaga cccaaaaata cagtgtagag attcacactg aggtaactca gggagtggaa   15360
ttcagggcct cccgctggga ttgaggtgct aatgacacaa ctcctgaacc tgaccttaga   15420
gtgccagcca ttgacgtcaa caaagttgaa atgatgtaac ctgacgctcc cctgcgggg   15480 cttgtgcagg ggcctgggga gggggaagga gtggccatga aactgactag tggacagaac   15540
ccagctaagg tcaggacaag acagagtgaa ggtcccctgg cactgatgtt acagaagaat   15600
```

```
tcggtggtaa ggggcttctg gagagtggca tgtgctatct aagcgagtgg cccaaatcct    15660
tcctgaaagc atttatccgg cactacagcc accatcaggt aagacagtgg gcttcttctg    15720
gccatggatg acacagccat gggggtgagc agcagcactg ccatggcagc gtgtcactgt    15780
cacatgggga ttcacatatg tacctatgtg tgttcatccc cgtgtgtgca catattgccc    15840
cacctgggga caaagggtgc ctggccacat ctggaggggc agcggtactc ctgtggccac    15900 gttgggggtgg tctgcatagg tctgatgcat tggggtcaga ggggcagcct ggcctgtggc    15960
tcctcttctc tcctcacaac tccagccctg aaaagctgct ggggaggccc ttggggatga    16020
cctctcctcc ctgaggtctg ctatggggc gggtgctgag cctggagctg tgattctgct    16080
attggatttt ccaggtggat tttctgattg aaaatgatgc agagaaggac tatctctatg    16140
atgtgctgcg aatgtaccac cagtaagtgt gctgggtcca gctcttgtgg gccacttggg    16200
ttcctttgtc ttcagggagc cctgggatgg gttgttctga gacagaggag ctcagagggt    16260
ggatgctcac ggctcctgga aatcaaatgg acataccatt cactcatttc agcaactatt    16320
tacacaagta ctttgtactt ggcttttgtac taggggctgg gtagttgt gagccagaca    16380 gattggtctc tgttttcagg ttgctcacag tctgatggag gaggctgtct agtagccaga    16440
tagattctat agagcatgat tgttgggaca gaacaagaaa tgccagctgg ccacagccct    16500
tgcatcagat gtctccgatc acccacttgc tttttgattc attttttcta ctttataagc    16560
tcctgccact gctgggcact gtgcagaatc tggaaatgaa ttagatccaa tttctttcct    16620
tgagtaactt gtggtctggt gagggagat gaacatacac tgcaaacaca agaactcta    16680 atataagtta catcaaataa ctgctaagta gaggtaaaag cagaaatgtg aagaaaggag    16740
ttttcctttc caactgcgag ggaagaggaa ggaccaggaa ggcttgagca aggctttgaa    16800
ggataagaaa gatttgggc caggcaaggt ggctcatgcc tgtaatccca gaactttgag    16860
aagctgaggc aggaggattg cttgagccta agagttagag accagcctgg gcaacatggt    16920
gaaatcccat ctctacaaaa aaatacaaaa aattagccgg gtatggtggc gcgtgcctgt    16980
agtcccagct acttaggaga ctgaggtggg aatatcacct gaacccagga ggtcaaggct    17040
gcagtgagcc atgattgcat caatgcactc cagcctgggc aagacagcaa gaccctgtct    17100
caaaaaaata ataataaaag aaaaagattt tggtaggtgg aatatctggg aagggcattc    17160
cagaatgagg gatcagcatc agccaaagtg tggaggcatg aaagcaaggg tgtgaatgga    17220
gataagtaat ctgggggagt aggacttggg agggcacgga gatcataaat agccacaagg    17280
ctggagaagc tccatgggga caggtcatgg agggccttga gcctgctgag aagagtggac    17340
tttgtcctct gggcagtaag gggccatcaa agggttttaa gccagggagt gccttacact    17400
gagaaaagat gacgtgacag tgagtacatg ggcaggcagc tgcagtcgaa ggtctgaaca    17460
gcatgaggga ggaggcatgt gaactgtggt gaggtgaaat tgacagagct tagcagcaga    17520
tacgagtgga gatgatgagt gtgtgaggaa ttgtcagcat ctcacacaga gctttcccct    17580
ctggaaagat cccaacagcc gagataggca gcgctgagtt tgaaatcctg gcttcatctc    17640
atctgcaaaa tgagtcaaca atccctagta gactggtttc ctggggatat ttatataaga    17700
gaacaaagtc ttctcaggca ctggcccggt gtgaagagct ctgggctttt caggagtggt    17760
ctactccatt cctaagcctg ggcccagtgg ctgaaatggc ttcctcttgg aatccctggg    17820
tgcctgaggt catggccagg ggtgaggctc caggcattcc cggcatctcc acaggaccat    17880
ggacgtggcc gtgctcgtgg gagacctgaa gctggtcatc aatgaaccca gccgtctgcc    17940
tctgtttgat gccattcggc cgctgatccc actgaagcac caggtggaat atgatcagct    18000
```

```
gaccccccgg cgctccaggt gcagaggaag ccaccaggct ggaggcaggg ggtggagaga    18060
tcaccctggg cggggcagtg ctggcagcca agctgcacca tcaccgacct ctcctgtgtg    18120
gcaggaagct gaaggaggtg cgtctggacc gtctgcaccc cgaaggcctc ggcctgagtg    18180
tgcgtggtgg cctggagttt ggctgtgggc tcttcatctc ccacctcatc aaaggcggtc    18240
aggcagacag cgtcgggctc caggtgagca acagagtcc gggggagggg gagcgagggc     18300
ctcggacctc ctgcctcccc ctcattcatc cactaggctg tgtggcacaa catggtcacc    18360
cacttttctg agccttcggg tgaagaagag gctggcgcat cctgatgggt gttcttaggc    18420
tcatagaaat caggccgcag gcaattgcct gttttcttga gtgaagctgg taacctggct    18480
gctgcctgct tccaactgct gcctccttcc agctgctgcc gctgcacttc ccccacctc     18540 ccctactccc caagagagga agacagtgat gctggcatat gaagttttgg acctgttgcc    18600
ttttaccagc aggggggaaag aaagcctggt gcagtgtgat gccgaagagc atagactctg   18660
aagcagggtt agccgggttc aattctggct ttgctgttca ttaggctgtg tgacttggtg    18720
gaatgactta accctgtgct tcaatttcct catctataaa atgagttgcc gatagtactg    18780
tctacctcgt caggttttgt tagtaaatga attaatagta gaaagtgctt atagcagggc    18840
ctggcataca aatgctgtga gcctggtaag tgaacagaga gagggagatt taagaaacgc    18900
ctggaatgtg ccaggtcaca tgctcacaag cagtccttgc tatatgcatt gaacggatcg    18960
tgcccatttt acagaattaa tagaggctca gaggccagta agtggcagag ccaggattag    19020
aaactaactg ggtctcctga ctgccaagcc cagaaatctc tcttcagcaa cgcaggtgcc    19080
tctcctttgg ggtccccaca cctcagggcc tgagcagaga tgggcagacc tccaggtctc    19140
actcctacct gagcccaggg ctgtgttttt gtgtgttgag ataaaggagg ccctcccacc    19200
atcaccaaga gcttccagcg ggtttgttat caacatccca atccaggctg ccaagcttgg    19260
ggctttcaag gggctcgaag gctaatggta caagacactg tggcgtaagg ggtggaaaca    19320
gggagctgac agacaccgct ttgttctaaa tccctgtctc acggctccct ggtggtgtct    19380
gaaatttcag ccccttcatt atttctttcc tctgcagcac attttccagc tcagaaatgc    19440
agccagagaa aacacataat gagcgcctct cttggcgtca gctgaggccg ccttttttcc    19500
agggcgagct ctcttaggac aagcagttct caatgctgcc tcgatgactg ggggcgttgg    19560
ggtattttaa tgagacctac agttttacct tcctggctgt ttctcaggct tatgaattat    19620 cggcccttc tctagctgac gggttcatct ctcctttgtg ccgctgtccc tcagatcgtt     19680
atatcatcgt ggcccttgca caaagggccc tttgcagggc tccacacagg gcgagacggg    19740
gaggaaagtt gatcctgcaa cctgagccag ggctgtgtg ggaatcattc cgactggggt     19800
tctgggcaaa ttccctttag gaataagaca gggaacttta tcagaggag cttcgggaaa     19860 aatggctgca tccattgacc tgtctggggt tcatgcttct ggggagatct catgcctgag    19920
ggcaactgga agaagatgct ggaaggcagg ggatgagcag gttcagatac agcccggctg    19980
ggctaaagac ctgtgctgat ttgacctgtg aggctgggtc cccagtggtg ggcttggacc    20040
ctcccacagg acctagtcct gggggtccac ccctctgccc ttgtcccctg ctggagatac    20100
ttggtttttg ttttttttc cccaagaata tcctaactta acctacatcc tctgccttgc     20160
acagggcagc ctgtgacata caacttgctg tatattccag acctagaaaa ttattctgtg    20220
tgctttggtt ttccctgtca taacatggac agctgccttt gtgtgggact tgagggctct    20280
gacaggtggc aaggatccag agagggcagg atgcaggaa ttgcagctag gcttggccgg     20340
```

```
atgcccttct tttctacttc cagacaccca agagacacca cttgtcgatc agggagacct    20400
gacttcaaat cccacgacac tgtttactat tggggtaacc ttgagcaagt cactttacct    20460
ctctgagcct cagttttctc atccgattaa cagagataca aattcctgct ctgcagggtt    20520
gttgtgaaaa ataggtggaa ggagttagtc tggccgctgt ccttgaatta catgttccca    20580
gaaacctaga gagttcttta gtgggccccc accccagtgc cattttgagc ccttggccac    20640
tcctgtcagg tccctgagaa gactggggtc tgtgtcccgg agtgggaggg aagcgttcct    20700
tggaatagtg agaaggtgac tctgtgggaa tgctgtagag ggcaggagtt gccctagagg    20760
acccctcgga ggctgcatgt ccacccagcc cctacctacc tagacccaca gggagtccag    20820
cttgcatccc tcacgtgtgc cagcacgtct ccaaagggtg agcacgtgtg tttcgagtta    20880 agccccagc tgacctgcac tggcctcaga ccggaacctc tccaggagcc agtctctgtt    20940
ttgcagctac tggctgtgtg accttggaca aaacctcact tccttgggct tcagcttcag    21000
ctgttatctg agagttcctc ctgccctgtg gttattaaat gaggagctcc agaattgatc    21060
cccagggccg gggtgcctgg aggagccggc agtatccagc aggggggcaat ctcaccacgg    21120 ctctgtatcc agggctggct gcccagggcc catctcaaca atccactgtg gcctaagccc    21180
tgagaagaga gatctgagct gagtattcag ggatcaggac taactcatga taacaatagc    21240
aatcatgtat tgagtgctta ctgtgtggca ggcactagct gtctttacat gcacaagttc    21300
acttaattct cacagcaacc ttggtattcc ccattttaca gacgaggaaa acaggttcag    21360
acagttcaag agacttgctc aaggtcatat agctaataat aataaaagaa gggatttgaa    21420
cccagcacat ctgatgccaa agccctgtgc tcgttcactg ttctttgctt gctcccaaaa    21480
taggaattca gaggtcaggg ccacagcaga gttaaaatgt tcatcaagtt tccatatgat    21540
gggaaaaaaa aatcatatgt gtgtgtgtgt tggtgatgtg agcttgggtc aggagtcaca    21600
gaaggtcccc accccgactc agttacagtg ttgtagcaat taacagagat agggagccaa    21660
cttcctaggg gtgggttggg acaaagtccc ggtaagaata gcttaaagct gagtgaaatg    21720
tcaccctttg catagaatcc agaatctgat ggtgccccag tggagtgaaa ggggcactag    21780
agtgagggtg cagagagttc tgagatcttc tcccagctct gctgcacacc cgctgtgccc    21840 ctcaccctg tcttggtttc tccatctgta aaatggggcg acaagactgc ttggacatgc    21900
cacctgaacc tgggatcccc cgggctgatg gaggtgtggg tggttgagat caaggcttat    21960 tccaggggt ggcacagcca cccttccctt ttccggagag cagtccggga gcatctggtg    22020
gtgagtctgc cccactgcct gatgctccct ccacctggtg ctccctgcct ctctctgtgg    22080
tcaaggtagg ggacgagatc gtccggatca atggatattc catctcctcc tgtacccatg    22140
aggaggtcat caacctcatt cgaaccaaga aaactgtgtc catcaaagtg agacgtgagt    22200
gaggccagag cagggcagta ctccataacg gtgggaggga gggagggcgg gggagcaggg    22260
cagtactcca tgacggtggg agggagggag ggcgggggag caggtcagta ctccatgacg    22320
gtgggaggga gggagggcgg gggagctgtc ctaacccctg tgcctttctc ccgcagacat    22380
cggcctgatc cccgtgaaaa ggtgagaggc ccctcctctg caggccaact cttccctgtg    22440
ggcccaggat cctggtacag ccctgggtc cggctcccac catgccagcc ctgcttctgg    22500
gccagtggag gctggaggct ctagacatgg tggatctgga tgtgggcct ggttcctcaa    22560 acgtctctcg ctaaccaccc tcccatctat tttcccttcc catcagctct cctgatgagc    22620
ccctcacttg gcagtatgtg gatcagtttg tgtcggaatc tggggtaagg gccagacctc    22680
ctgtgatggg gtttgggtgg ggtcatcttc aaggaggggt ggccggtcct gaaggagggg    22740
```

```
cttgctctag agatgcaccc tcagggcctt cacacaggct cccagggcag ccagcacacc    22800
gctgtggggc agcagccctc ggccaggccc agctggtgca gacacatccc cagggacgga    22860
atgatgatct ggctggcgtg agttcagcag tgctcgccct gcagatccca caagctcaag    22920
aggccgcttg cacgcatgtg gacactccgt gattctgctt ctatctctct ttcagggcgt    22980
gcgaggcagc ctgggctccc ctggaaatcg ggaaaacaag gagaagaagg tcttcatcag    23040
cctggtaggc tcccgaggcc ttggctgcag gtggtggca ggcatgccct ggggtcattc     23100
gtggccagtg caccccagca ggccctatt gccctcccct tcctcactgc cacttccgag     23160
gaaaccttgc ccaccagggg tgtgactgtc catgggtgat gatactttt ttgttagata     23220 cagggtctga ctctgttgcc caggctggag tgcagtggca tgatcatagc tcactgtagc    23280
ctcaacctcc ccagctcaag caatcctccc acctcagcct cctgagtagc tggatctaca    23340
ggaacacact gccatcccca gctaactttt aatttttttg tagagatgga gttttgttat    23400
gttgcccagc tggtctcaa actcctgggc tcaagtgatc ctcccacctc agcctcccaa     23460
agccctggga ttagaggcat gaagcaccgc acccagcctt ggtgttgaca cttcttggtg    23520
cctgatttcc cctctgaact tcatgacagg cctttaggggc cagagggtca tctctaacag   23580
agcccaattt acagatgagg aaattgaggc ccagaggcag aacagtgtta ccttgtgggc    23640
ccttgagtca ctgcaaaagg agcctgtttg gctggtcatc tctgtcacag ctctcttgtc    23700
acttattaac ttgttggctt ccttaagagg cagacaggga attccgaaca gacactgggc    23760 cacacgggc ttaagcatgc aggtgccacc gttactcaga tcccagttcc agccctgctt     23820
tcccacttaa gagctctgga accttgggcc agttacttaa ccactttgag cctcagtttc    23880
tccctctata aatgggcgat aataattccc acatcacagg gtggttgtgg agaaagtaaa    23940
gtgccaaact tagtacctgc taaatagtaa gcagttggta aatattagct attattattt    24000
aagttatccc tgttctttcc tttcattcac atttattcaa tgttttgtgc caagcacaag    24060
tgataaaaag tcccacccttt ctgggagaca acagcctaat ctagaagcca accaagtaaa   24120
tagttataat atagggtgat agggactcga acgggactac attctgcgtc caggatggca    24180
aataggtgcc atctctagtc aatgagtagc agctccctgg agtgctgctt tgaaaagcat    24240
tctaaagctg tatccaggat tgtgggaaag agtgctgtga tcaatgagtg acttctgcca    24300
ccaatctagg aaggaatact aacagtacat gtaccatcct tgccgtaaat gtcataggag    24360
cactgagaac agagcggcta gtttagtctt gggatagaat aagggatctg agccaggcat    24420
ggtggtgcac acctgtagtc gcagctaggc tgaggtggga agattgcttg atcccaggag    24480
ttggaggttg cagagagcta tgatcacacc actgcactcc aacctgggtg acagagcaag    24540
accctgtctc taaaaataa atttaaaaaa ataagaggat ctggtaaaaa ccttatagaa      24600
gggatagcat ttgagtctta atggatggac aggaaagtgc tagaaagaaa gaagaaacag    24660
catatgaggt atattaggtg agaggttggg taggaagaat tacaaggatt tttctgtggc    24720
tgttgcccag ggtagcagta gaaatcaggc tggagaggga cacagaggct gaagaggtag    24780
gcagtcaagg gccttcagtc ctcagctcat gagtgacctg tatcctgagc actggacatg    24840
ggttacctga atcccgagca cacatttccc acctcccgca gcatttccag cggccccatc    24900
cagaagcctg gcatctttat cagccatgtg aaacctggct ccctgtctgc tgaggtggga    24960
ttggaggtga gtgacgctgg gccggcccca gtggggggcc actggaaatt gggtcagact    25020
gtgatcccgc ggtgacaggg gcaggtgcct ttccacatgg ccctctttca gtggacactg    25080
```

```
agggagtagg agccctaccc accctgcaga gaaggcttca cagactgggg atgtttgacc   25140
cttctgcagc cttccccagc tctgatagtt gttggtcacg agcttgggaa tgtcgtaatg   25200
gtaatcaaag agcggacctt cagtgtccac ttgcatcaga cattgttcca tgcccttac   25260
acttcacaag aatgctgagg gttaagtacc accattatcc cactttaca tatgaggaaa    25320
ctgagaccca gagaaagtat atgattttc caaaatcgtg tacctcatat ggtagggctg    25380
ggattcaaac ctaggtggtc caatcccaaa gcaggaaccc ttaacctctt ctttggacaa   25440
gttacttcat gtctgtttgc ttacctgtaa gatggggata atacaggctt tcttccaagg   25500
ttgttgtgtg ggttaaagta attaatatgt atactagagc tgtgccaagc acattgtaag   25560
tgatcagtga atgttagcta ttctgttatg acgattcaac acagcctgtg ctaaatgaga   25620
agctcaaagg ttcccgcatc tgcaaactgt gattttaaa gcaaatgtca tcaaatttag     25680
ccaaagaaat gaacatgtaa tggtataata tttgatagtt gataagatag ttatgaagta   25740
ggggagtgcc agggtcagct ttaagccctc ccagagctcc accagagctt tccaactgct   25800
ccattcatca ggaggagctg aggtactgcc acttgaagat ccagcatctg acccagagcc   25860
cctgggggag cctgtcctgc agatgagcga gtgtacagat agcgcaaaca cactaatctt   25920
tctccatttc cccaccagat aggggaccag attgtcgaag tcaatggcgt cgacttctct   25980
aacctggatc acaaggaggt gagatgtggg ggtcttcacc tgttggcct tgtcatctcc     26040
acaccccact tctcatcccc accacccctgg agctgtgggc cttctgtgct ctctgcctgg   26100
actgctgtgg tctgtcaggc ctcggcccac tgtccttctg tccccacagg ctgtaaatgt   26160
gctgaagagt agccgcagcc tgaccatctc cattgtagct gcagctgtaa gtccagaatg   26220
agctggtggg agcccttga ccttcatccc cagcccctct gacctttgat ctctgccaca     26280
cactcccagg gtggctggtc tccttccctg aagctctgac agagcagagc gagaggactt   26340
ctgcccagca agaagtttgg gtcagggatt gcgggagccg cagtgcctga tggtgctgag   26400
aagaccacct gcatctcggc ccccaggggt gtgtcagggg atccccaggt tccccggggg   26460
ctgagcaagg ggcctctttt ctcccatgag ggccgggagc tgttcatgac agaccgggag   26520
cggctggcag aggcgcggca gcgtgagctg cagcggcagg agcttctcat gcagaagcgg   26580
ctggcgatgg agtccaacaa gatcctccag gagcagcagg agatggagcg cagtgagtg    26640
cagccagccc tggatgccct gtcccgcctc ccaccccacc acacgacccc acctagcttg   26700
cttcctgccc gctgtgtccc cagccaactt cctcctcctc cctggaggcc agtcctcaga   26760
ccagatgagt ttggtggtag gtcagcgtat ccatccttgg cctcagacca cctggctcct   26820
tcctccttgc tgagcagagc ccctgtcttt ccaacattcc aagaatatgg aaaataagca   26880
tcctactagc agtaggctct agctagctag gattagctac cagctaacat ttgtcaagta   26940
cctccataag gctggtgttg tattagggcc ttgtttatgt ttcttaattc ccacaatagc   27000
cctgggaggt agagagtatt aaccccattt tagaggtgtg gagactgaca ctcagagagg   27060
tgaagccact tgtgtctaac gtcacacgtg gccaagctgg gatcaccccc aggcaatctg   27120
gcaagtcccc acagggctgc cctgcctata gtgatgaagc tcacccttgt ccaggaggat   27180
tgaaatgatg gcctaagaga ataaatgggg tgagcaattc ataaatcaaa aactactgtc   27240
aagatccaaa tccaaatacc ttttaggcat ttaaaagtat ttcatggctg gacgcagtga   27300
ctcacgcctg ttatcccagc actttggagg tcgaggccgg cagatcatct gaggtcagga   27360
gttcgagacc agcctggcca gcatggtgaa actgtgtctc tactaaaaat acaaaaaaaa   27420
attagctggg catagtggca tgcgactgta atcccagctt ctcgggaggc tgagacatga   27480
```

```
gaatcacttg aacctgggag gcagaggttg cagtgagctg atatcgcacc actgaactcc    27540
tgggtgcaaa gtgagacttt gtctcaatca atcaatcaat taatgtattt tgaaaaggaa    27600
agaggaaagg ctgtccccat ctcccccaac acagagttag ctgggagtat tccacctggc    27660
taggagcccc tgctttgctc ctggggtcag tccaggcccc gcctgtcatc agtcaccttg    27720
cctaagtgtt tggaggaggg tgcatggagt gtggccttca catggatctg cttccctcct    27780
cccacagccc agcatctctg ctcagccatg ccagacaaaa ccacgcaaga gcacagcgtc    27840
cagactttgt tagataacgt cccccaaaac caaagctggt ccaggcctcc taggaaggga    27900
gcctggagaa aaatccaact tttctccaaa tcaagaattc acagtaagga agagttcatt    27960
tctcttgcat agggccaaac atgccaatct gcatttgtgt ttcagaagga gaaaagaaat    28020
tgcccagaag gcagcagagg aaaatgagag ataccggaag gagatggaac agtgagtacc    28080
tcggctccac gcgtgtctgt gcatgaacat cagtgtgctc aggggagtgt ggccaaccag    28140
aggctgcctc cagaaccagt ttacctggtt ctctcatccc ctggtgggtc ctcctttatt    28200
tgtagtaaag cctgtcatat tatagtaact gaaacatagt ctcgtataat tgccaaggtg    28260
gggttcacac tcaatttaga atacaagctc ggggactttg cttgattcat catgactaga    28320
accatgaggc ttctccccag gctggctggg gctctccgat atgcaggaga tgggcctatg    28380
ggggttctga ctccagtaac aggcatgggg gtctcatttt aggattgtag aggaggaaga    28440
gaagtttaag aagcaatggg aagaagactg gggctcaaag gaacagctac tcttgcctaa    28500
aaccatcact gctgaggtac acccagtacc ccttcgcaag ccaaagtgta agtttcatga    28560
gccgagggga gaggctaagg gaactagtca gaaatgctgg ccctccctcc cctcaccacc    28620
acctcctaga tggatagccc ttggtgctct gggctgtggt tccttcatgg aggggcagct    28680
gtgggtcaga gaccatctgc cccagcatcg aggtaggagg gatctgtctg ctcccccttgt   28740 tcacgggcca gctccacata cccagctccc aggtccccca caacactgac atgggcaggc    28800
tgtcaggctg ctgaagaggg aataagggcc atagtgaaag tggattagct catgggatta    28860
ccgtcctaat gttttgggta ccatgtcctc ctcctacttg gttctgaaca ggggctgggg    28920
tgaagccagc agcagaaaag aggggaagga cctcacatca gagaagggct ctggtggtcc    28980
aaggttgatt cataactgtg ggaggagctt actaagtgtc tccagcccct atatccctgt    29040
atgtggacca aggatggagg caggaacagg acaaggaggc ctctcccaga cacccagcta    29100
tgggctgtgg ctgtgctgtc ctggggcctc agctcatact ctccttacca tctcctctct    29160
tcatccgtcc cacatcctca cctccatttt cagtctaagc ctctaccacc tgctcccctga    29220 ccaccttctc aaccccagct tccatatgcc tctttaagag gcagcccaca ctgccagagg    29280
aaaacgggga ccatgacaac cacaagtcca ggattgctgg ttgggtcctt actcctgcct    29340
tccagctgtt ttgacttata gttgacacag gacaggtcct actccagctg attgtgctca    29400
gctgacctgg gaacctccag caaggggcta ttctggactc aagagcccag gttccccatc    29460
tctgctgtgg ggcagtcatt tggcatgttg tgatggggtc tggacagctc tgtccccaac    29520
tttgggtcac atatgagacc tatgggaatg tcaacctgcc aacataggcc acttgcacca    29580
aggaagaggt gcagggcatc tggatggttc catttcaccc ctccctggtg cagtcaaaca    29640
gctcccaaca catttcttcc tggcagcagg gcagtgtcat ctcctggtcc tctcagaagg    29700
acaaagcaca ctctcatcag cctcccccgt gacattcagt atcagttgag gatatggcca    29760
gagctaagat cccaatgaat gatcgctgtt ttagacagac agctaatttg ctcttacgag    29820
```

```
tgaaatagga gcttcaggag agaaatcgat tttaattgct tctcatggaa gtaatcctag    29880
tcaatttggt accttccaag aaattgggcc tcagcttcac agcaaacaca ccctctcagg    29940
agcaatagaa aataaaaacc cttttcactag ctggttattt atttagtgcc ttttaaacaa   30000
atcaagctct ttgaataaaa agaccaagaa ttttgcattt gctcaaggta aatgtgatct    30060
taggcagctc cacaaagcac aggatggatg accccegcct gcccgctgag ctgggacagc    30120
tgctgcctct atctgtctct gtatgcacca gcaatttaat tctcatttgg acctaaggca    30180
ggaaatgcag tgaggtccct gagccagctc acctcctgcc tcactccctg ttccccgggg    30240
tctagcatgg tcagggctga gttggtccag caggcctggg ccccagccag ctcctatcca    30300
accacccttc aactcagcac ccagtttgca ataggttata cctgactcag gcttctatgc    30360
ctgcaagggg tgggccctgc ttttttttt tcttgagac agagttttgc tcttgttgcc      30420
caggctggag tgccatggcg tgatctcagc tccccgcagc ctccgcctcc tgggttcaag    30480
caattctcct gcctcaaagc ctcccgagta gctgggacta caggcatgcg ccaccaagcc    30540
cagctaattt tgtatttttg gtagagacag ggttttcacta tgttggtcag gcaggtcttg   30600
aactcccagc ctcaggtgat ctgcccgtct ccacctccca aagtgctggg attacaggca    30660
tgagccactg tgcctggccc cgggccctgc atttttttaaa ataaaagagc atggggcatc   30720
tcttacctag aaaatgaagt cactcatcct aattatgtgc ctgggactga ctgccccca    30780
acctgcccca ggggggccctt aaaattgctc ctgcccacct acccgtggct gatccagcag   30840
accccccaaca ttttgccaag ccctgaaggc caggacacca ccacagaggc tcctaacaga   30900
ccttcccctta gctaggcag gagttatgta ggtggttatg caggagttgc caggggcagc    30960
cttgactaag gatctggtag ctgaaggatt cttgaaagat ggagatgttt aaataggaca    31020
tctccaacct tctctcccta tccaaggccc catcaactat ctccccccacc tccaccacaa   31080
gagaccccac gatttggaag ttgaggttat tttcctaccg aactattaaa taatcatttg    31140
tgttccattg ttttattaag tagtccttgt tagtaaggga gcatcagggt tccactgttg    31200
ggtaaatgta atttgagcca agagccaaag aacttaacag cctttgcata ggccaatggg    31260
caagttctgt taagctttta aaatattaaa aagcagctca caagcaaacg ggtatactac    31320
cttccagagt cctagggagg ccggaggcca gagtccaagc tggaaactct ggaatggagg    31380
gtttgctctt ctctccacat tatgtcaaaa ttcaggtctt cctaactgca tgtaccccctt   31440
ttacctttg ggatgtcccc acctcctcag gaccttcagc ctccatctgc tgcccacact    31500
gttcagacat cccctagggt cccagagctc caaggcaagg gtgataagca caaggctgga   31560
gggtctgttc tcccattgca gccccttgcc ctcaaacgtg tgcgattctc agatattccc    31620
atcctcctca ctgcacttcc cagccttcag cccaataccc tacaaaatgg ttctcatgct    31680
accctcagat ctgagtttcc tgttgttagc cctttgtaca gacagaaaaa ctaaagctgc    31740
caaggttgaa aacactgtat gcaccagctc agagcaaaaa acctttgctc tgctctcctg    31800
aactctgtcc cctgcccctg acctcacagc tcccatggag gaagctgatt acaggtcccc    31860
aaactcctga gaaggttctc cggcctcttg ggctcccaag tcccttttgg ttcaccagct    31920
tcctcctctt ttccctgggt agatgatcag ggagtggaac ctgagctcga gcccgcgat    31980
gacctggatg gaggcacgga ggagcaggga gagcaggttc gcgtccccgc tttgctccct    32040
ggcctggctg ctctgctttta ccctgcccgc ctcctcctga ccgcagtgca gacacccagc   32100
ttcagggggcc cagcatgtgt gggggccaat agagtctgta aagctcctcc aagccccagc   32160
ttggcccaag cactgtacac aaagcctaga cgacaggact caatgcccag gctggtagat    32220
```

```
cagctgttgc acactggtac cactgaaccg ctggctcgaa tatttagata ttgccaaatt    32280
ccccctctgc tgctctggcc cctccccag gacccctag accactctca aatccagcaa     32340
ctgaggaggt agtgtctggt ccagcaggag gctttcagca tcctgttcca gcactcaggc    32400
tggtccgggg tgggtaattc agccatcgct cttggcccca gggagcttca gattgggggt   32460
attactctgt ggagctgcgg cctggggaag gaaggggct ggtgcactgg ctatctggcc    32520
tggatgagga tctgttttct gggggcacat tcctgcccg ctcctgctgg agctgtcctt    32580
ccaagagctg tcccagccac tgccttctct ttgaatgttg aaagcggagg acttgacctg   32640
cactatgaga caagccagtt tgttctgtc gaacaacagt tctaggcaga cacccaggct    32700
cccttttgtc tcgagccatt ttttgtatgg agggaccaga catgggttag aaaaggcctt    32760 gttctcttc aacaaggctt tgtatgtgaa gactgtgatt tggaaaagct catccttcca    32820 caagggttt tctctttgat gttctggccc tgacttctga aaccagtgtt ctggggagag     32880
gcatttgaga gtgacccagg gcctgggaac cgggcttt ctcggtggtc ttaggcctgt    32940
tctgcaacca aggcaaggcc aggtaagccg agttggacag agggtgcagt tttgctgtcg    33000
gatctgccaa tgctgtttat ctcacaaagt catgcattcc ttgggaaccc agctcccatc   33060
tgctgcccat ggatgctctg gctgagctga actgtgtctc atcattttgt tatctgtgtc   33120
ttatagcttt tggatggttt tatcgttacg atggcaaatt cccaaccatc cggaaggtag   33180
gacagggttg ggtgctgtgc tggtgtgctg cttagtttgc tgtgggtttt ggcttttccc   33240
aaacattcct tgtcctatca acactaaatg gtgtgacttg gcctgttcac ttggaaggct    33300
aactccatct ccatctttgt gtcaggctga catcaaatgg cagggtgctg ttgcaaaggc    33360
aacattggga gagggatcca tggtgtgaga cctatccaag taccatctgg cagtgtgtgc   33420
atcagcactg gccctgatgg gaacaggaaa ggggcaggaa gcttctcctg tgtttctctg    33480
tcaagtagaa ctagagacca aggccagaag cttggggtca gacagagcaa attatcggag   33540
tgggtgtacc tagtgcatgt tatgagacca gctgtgccag acgcagcctg gctgacgagg   33600 tgggatttg ctgcctcagg ttgggacaga gacccactcc aagcacagcc ctctcctagg    33660
aatatctctg catgtgccca ggataatgca ttttccaat ttctaggacc tttaatttc     33720 tctctaaatc ttattacaat atctccaggc cttgtaaaac tctcttgtcc ttatctttct   33780
aaatcacatt gacatttgat tgtgaaaaca ttgctgttaa tatctataat tggacattcg   33840
agatgacttg gtatttggag gtcaggcagc agcataaatc tgggtgagct aaattggatg   33900
ttatcacttg accagcgctt tctggcaaga tgtcagtccc ccagaaacca gagcactggc   33960
agctgagtga ccttgatgat atataattct ccctgcctgt aaaatgggaa tattaactgt    34020
gccaggaaaa tctaccccct tcctccagca cattgctatt aaaataacaa acagtaatat   34080
ttttcctgac agaggttaat gcctttatct aggaacatct atcaggattt gtatagcatt   34140
gaataaactt ggaacagagt tcctctggga attccttcac acattgtcct ggtctcagaa   34200
aggccttggt ctcataagac tatctgtttc ccttgacagg ctgactttgg tggcttagga    34260
tgcctcattg ggttagattt ctaattcttc tctatattct gcctctacta gaactcagct    34320
agagaggaca aacacacac acacacacac aagcacacac acacatgcac acataggatt    34380
ttacttgaaa aaaataataa aggagacaga tatgtcaaat cttttcagg cactaataac    34440 atgtaaatgt aaaagaacta gaatcttctc cacataccac ctcccatcag aaatcatgtc   34500
cttgaaagtg ctgttgataa agaaataggg ttgccttcc cctattcctt aatctaatta    34560
```

```
ttccagaaac agctgtcatt ttggttttca ttttcacttc aaaaaaaaaa aaaaaaaaag   34620
aattgcttct gggtagaatc aatagcacaa tcgccccatc tgcctcacct ctcagtctgg   34680
accaaaagga atattgtaac tgacaggcca tggatgtaac tgacagctga aaggacaaca   34740
gaaccatgcc cctcatactg gctctgaaaa cccgtcatca tttttctag agccgtgaga    34800 gactctttgt ctcccagcag ctggaacgcc aagtctccag gaaatgcaag tgggtatcca   34860
tggccatgat atctgtgcat aaattcccct tatttaaaaa tataaagatt cagctcatgt   34920
ctataatgcc agcactgtgg gaggccaaga caggcgaatc acgtgaggtt gggagttcaa   34980
gaccagcctg gccaacaggg tgaaaccctg tctctattaa aaattcaaaa attagctggg   35040
tgtggtggcg catgcctgta atcccagcta cttgggaggc tgaggcagga gaatcacttg   35100
aaccctagag gcagaggctg cagtgagccg agattgcacc actgcactcc agcctgggtg   35160
acagagcagg accctgtctc aagaaaataa taataataat ataagattc agtgtcttct    35220 atttccacct tggcagtaaa tccctctggg gctcaaggtt cccaggcctt tggccccaca   35280
gaatttgtgc cagggcatga aggattcatg attctgacta agccctttca tcagaattgc   35340
ttgagtcact cacacagacc agccctactt gcaggagccc accgtctggc agggaaggca   35400
gattcacaca cagctaagta acctgtgtgg ggccagtctg agatcagtgg gaaatgccat   35460
ggggcaactt gccctctgca tctgtacaga tatgactttc ttgggcatga gacagaaact   35520
gtctactacc ccacccagaa gccctgactc tataatctta gcactggtag ttttttttt    35580 cttctttct ttcttttttt aagcaacaga atggccatta ttctcgtggt ggtcctggag    35640
gaggccaggc tcttactcta gcaagctacc attaggcagt gtttctggct cctcttggga   35700
aattgctgtc tgaatctcta ctacgatggc agggattcat ctatcaactg agtctagtga   35760
acaaggtagg caaggaacca agcaggactc tgaagcagtg agaaccattt tctcgagagg   35820
ctcatacact gctctggagg tgggtcccag aggtgaccat ttccagagca cattagcagt   35880
acacagaggt gtgtgtcttt aggagaggag ctaggaagag tccctcagag gtccataatg   35940
gcccaccaag tccctccagc tgtggatgaa tgttgtgtgt ccattgctag ggagctcaat   36000
tccttattcc tggccttgga tactaagatg attcagaaaa ttcaagagca gatccccaga   36060
aggcttgttg ggggcggggg tgagctcagt gaacagggg tttcctcctt gccccagaaa    36120
ttgcccaggt gtgggctgt ctctgctgcc cctctcctga atgctcgctc tgtcctccac    36180
gctgtgtgtg atagggctg accctccctc ctgccgtgtt tcccttgccc ccagctcatc    36240
agggcaccat agaaaaacta ggacctcgaa gactcaggtc caaatcctgg tactatcagt   36300
tacaagatgt ctgacattga acaagggact ttacctctct gagcctcagc tccttcatca   36360
aagaatgagg ataaacctac ataggagatc attggtataa atcccttggc acataggcag   36420
ttcataaatg atcattctct tcctgcctta gcccctggct tccctgcaac cccatgagag   36480
aagcagccag gaatgcaggc tcggtgggtc taattcctac aggaaaaata aggagtctat   36540
ttgcctttca tgtccctccc caaatcctct agaaccctga tggtgagtgt aaagcagtta   36600
agccattctc tccatgccct gcctcccagt cctgcagttt ccagctagcc ctcggtagag   36660
gggcacaatt cagaggaaac tgtgggtcta gactctccag ggtgaaatgg tccagagctt   36720
aagcatgcgg gtaaaatctg atgtccctgg gtctgagccc ccaggtctca gtgtgactcc   36780
tatcacttct agcttaggac gggacctcta cagatgaagc ttgccagccc tcccagattt   36840
tctctggaat ctcccaggat gcatctctga atctgaacat gagatgatgc agaaggcatg   36900
tgccagatac tggaaaatca gcacaatgcc ctttatttat atggcactta tttatttttt   36960
```

```
tattttattt tttatttata cagaacttttt acaaagttct ttcatggatg ttattttcatt    37020 ggcactgggt ggcaagcctg tgggggaggt attttacca ttttggagat gaggcaaatc        37080
aggcccagag aggttaagga acttagccaa ggccacacag ctagttagtg aactaataag       37140
ccagtctttc tggctggtaa agagaatgtg tctcccactc tgcagtaggt agcagtggcc       37200
ttcctgtcct aaacctgagg tctgatgtcc agagtggtga gagagctggg ggaggggctc      37260
accatgggat ggttgtgtta tgtgaggact ggatgccccg tgtgctgtgc tgtcgacact       37320
atttctaacc tttgtcatat aaacaatgcc acatctactc agaaaggaaa agataagaag       37380
aaagccaagt atggcagcct gcaggacttg agaaagaata agaaagaact ggagtttgag       37440
caaaagcttt acaaagagaa agaggaaatg ctggagaagg aaaagcagct aaagatcaac       37500
cggctggccc aggaggtatg tgtcctgcct gcaggccagg caagcaaccc tgggacacaa       37560
tgtggtcgtt ctccatgtgc tcccagagga ccagctggag ttgttctcct caaatggcat       37620
acaagggtgg agtgagccct ttcctgctcc ccagcctgga gagagagatc atgccacctg      37680
cccagggcca tctgaggtta gctcctggct taggaattga aactaatctc cttgcttggg       37740
ggtgtgagtc ttgctcctgg cttttggaatt gaaactagcc tccttggtcg gggggtgtga     37800
gtctgaggtt agcctttctg accagatggt aggtctcagg ttagcctttg atacacctgg      37860
cttagagatt tgagtctgtc ctcttcactc taccccacca gagtctaagg ctgggcctct      37920
ccatctcagg tgtggctctg aggctactta gagtatggtc tgcggctaac ccttctgcct      37980
tgcttgtagc tttgaagtta ggcttccact gacctgtcta cgagtctgaa tcactctggc      38040
ctcccttccc aggttattgt aagaccagac ccccccccac ccaacttagc ttggctctga     38100
gaatatgggc ctgaggctaa ccccccttatg caggtggtag gtgcgaggtt atctcccaat     38160
taatcaggct atcagtctaa ggctgctccc ctcaacatag ggtgtgtcta aggctagacc      38220
tcatcaacct gggaatatat ctgaggctgt ccccatgaag acatgtccaa agcaaccttta    38280 caccatgaat aattcctatg ctaggtgaga tgggtaacct taactcccca gctgtaggag      38340
gtatcattgt ttctgcttct ctttaacgca tccatgaatc agaatgccaa tttgattaga      38400
ttataaaacc agagaagtcc tggaaaatgt gaaatgcatt aggtctgaca ttatgaacaa      38460
attagccaca aaattaaaaa taagattgaa cttatgcttc tgagggcaag gcagaatgga     38520
gcaggaaaaa aaagagtcaa gttaaactct tggaatgtgc tggggaggc tacaaaaact       38580 ccattcttgg aaaatcataa gagcctcagg gttcatgggg atctgggatc cagctaatcc      38640
ctcacaatac ataagcccct tttctgattt tgcctacaag ttctgcttag tgaatttgac      38700
accccgccac tctcttctcc cttgctgctg cctccttgag ggccagttgg aacaagccca      38760
ggtctctttc tagatagctg atgcacctca cagtactctg gagtttctaa aggagtgctt      38820
tcatgctatt tctatccaca tgttattcaa atgtgcccctt tgtcctctcc tttctgcgcc    38880
gatcctgggc cccaggtgtc tgagacagag cggaagacc ttgaagaatc ggaaaagatt       38940
caatattggg tggagaggct ctgtcaaacg cgcctcgagc agatttcctc tgctgataat      39000
gagatttcag aggtaacaga gcccttcttt ccacatagac cctcctgctg tcttcagaat     39060
gacccactgt ggggacagcg ggaggtgaga tgacaactag caaacgtcac tagcctcaca      39120
gtgcccatcc actgtccagg cccaccccta ccaccccact cccctcttga ggaggaggga     39180
tatgtctgta tttctgggta tactcccaga gtgatctcta agtccagct catctgcgat       39240 agtctcagtt aggcctgttg tcctggcatc atgactaaga gtcccccttta cactctcaag    39300
```

```
ggcattccag tttagagaat gaactctgtg aacaccttac cacccacaga tggcataact    39360
tggggctctt ctgcatttgg gcactcccta acagcagcct agtatggcct cagctgggca    39420
tccaggtggc agaggaatgg cgccccatgg ttctgatgta agggtggtgg gtctccagta    39480
gcaagagaaa cagattagaa gagcatagtg ctcgctgtat tgtgaagtgg agctctaagc    39540
agagtgacaa ttacagaact tccttgcaac accccagat gaccacaggg ccccgcctc      39600
ccccgccttc tgtgtctccc ctggcccac ccttgagacg cttcgcaggc ggactgcacc     39660
tgcacaccac tgacctggac gacatccctt tggacatgtt ctactatccc cccaagactc   39720
cctctgcctt gcctgtgatg ccccaccctc caccctccaa cccacccac aaggtcccgg     39780
cgcccctgt ccttcccta tctggccatg tgagcgcctc atcctctcca tgggtgcagc     39840
gcactccacc ccccattccc atccctcccc cgccatccgt tcccacccaa gacctcactc    39900
ccacccgccc actgccctcg gcgctggaag aagcactgag caaccatccc ttccgcactg    39960
gggacacagg caatccagtg gaggactggg aggcaaagaa ccacagtggg aagcccacta    40020
actcccctgt ccctgaacag agcttcccac ccaccccaaa ggtaatgtcc ctgttctgca    40080
tgctatgttt ggaagtagga agagtgggga gaactgctgt ttcccatgtc ctccactgct    40140
cctgagagtg gagacagaaa gaaacatcat ctcaccccat tttccaggaa tgccccctcc    40200
gtgtgcatgt gtggacatcc tgcatgtata tggtggttct cactgatttt gaagtgctgt    40260
attgtatggt gaatggcctg ggacctttgg ggtaagcaac ggtgtgtcca tttgatattc    40320
attgctctct cttagctctt ctttgctagt gtaggctggt aactttcaat gtaggacttg    40380
gaagtctatg ttaatgaata gccagcactc tgtcacatcc agtcacttcc tgatattatc    40440
ccagaaagcc ttgaatatgg gaaatggctc ctgatttaac gggaaaaaaa gggaggggag    40500
gaggaagcag gggcgtattt ggctctgtaa atgaagtgat aacactgtac catcaaatgc    40560
agtattagga cattccagtg ccattttcta cagtactggc caactgcact ggcttgaagt    40620
gtaataccca gaaatttctg gccaatttcc agctatagaa aaaatgaaga tgagagagtt    40680
cctagaaata atttactatt aaaagaatag gaatgttttt cttggatgtt aggaagatga    40740
acagtgtctt tctgaaaaag acatatttct tattaattat tcgtaatcca agactatttt    40800
tgaaacatgc aatctctgag gaagacaggg agcttggatc ccatgaaggg aaaaacaaaa    40860
tattattcca ctcccgtagc catgaggcca ggcttgagtc agtgcaaagg catctcatgt    40920
cagctgaggg tagcaggggt tgctgaggga gggcatagtc aatagcacct gaccagtggt    40980
ttttattaac cttccctgca tggatttgag ttcctgcgtg gagagcagga caagcatctc    41040
agagcactca ggagagctta caaggaaggt gggagtgaag aaagtgccag atgccagcaa    41100
ggctgaagct tccagcggga gactctcaga gggacccttt ctggacctct ggttggggtc    41160
gtgagccctg cagctttgac aggaagaaat ctgcctgttc tcgggacatc tttccccaga    41220
gcccagccag gagctggttt ctagagctga gttagcttg cacaacattt ttctctgtaa      41280
gtggcctcca tcaagatgag cagtagcttt tcctcaacaa atttgattcc actttgattg    41340
agtacctgcc tggggcctct ctctgtgaag gggagagggg agcagtgctg aagaggatgc    41400
agaggagatt gacatgcctg tgcttttccag gactttgcca tctgaaggat gagctgctgc   41460
ccaggcaggc ttctgctata aaatatgcat aagccatgcg ctatgggagg gattcattct    41520
aactgaagat tgaagacacc tctgtagagt agagggctta cgagctgagc cttgagggat    41580
ggcaacacat ggaggatggg agcaagggca ttgcaagtgc agggaacata aagatggcaa    41640
gttggagtag cagggagttg gcctgcctgg gtttgaatcc tggctgtgcc acttactagc    41700
```

```
taggtaactg aacacatgct acttcatcta tctgagcctg ggcatccctg tccaaaaata    41760
ggaatgctaa tggcagctac ctattcgaat caaataagtt aatacatgga cacattctaa    41820
gttaagaatg gcaagagtgg caggcacatc gtggatgttc agtagacatt aactatggtt    41880
attgatagtc cagagtaaaa gaaaatttgg gtgaagctgc aaacctggga tcttagcaat    41940
ctcagtgtca gcaaaacttt gagtcaggat caagattcaa gacagagtcc agacttctca    42000
gattcttcaa ggcatcacca agttcccact gttagttcct gatcagagcc agggaaggt     42060 taaaagcccc ccaacacaag gagcctctga agaactggac tataaatgtc acaagcgaca    42120
tcaaagccag ggttgtccca gcctcaaaag ccagggggct gttgcttggt tggcttcatt    42180
tggcccacct ctcacccttg taccacccac cctcctcctc cctgcatgcc cctggcaagc    42240
tgtcatcagt gctgcagcag gaagtgtgag tgaccacacg cccacacagt cagcccagcc    42300
accagcaggc cccaagtcat ggaaacaaac acctgtgttg gcttgacact tgtgcctgcc    42360
acaccagcac cggccatagg gggttttca gggccagatc tatccacagg cactgtccca     42420
tgttctcacc atactattta gtcattcatt tattcattca acacatgctt attgagcacc    42480
tactatatgc caaggcacta tgcagggcac tgggaatccc tgctggatag acagctgcag    42540
tctcccttct caagacagtc tggtggggaa caaagaaaag taggcacccg ccacaccatc    42600
agcgtggaga cggaggaagc acaggtgcta taataaggaa gagggctgga gtagaggaaa    42660
agctcaaggg aggcttccag aaggcagtga cgcccaactt aagacctagg aggcaaagcg    42720
gaagaaggaa gagcacgtgc aaaggcctca aggcaagaaa gcctggcatt ttttgaggct    42780
aaagctaggc agtgtgagga gcgtggcgag gagtgagaga taaggctgaa aaggaagcta    42840
gagaagctca tgaaaggcct tgggagtcaa gccaatgagc tcagtagtca atgcggacac    42900
tggggagggt ttgggggcag ggctgtgaac tgatttgata catcttgccc aaaaagatca    42960
agtgggttag agccaagcag acaggttgcg tcagctcccc tggatgcctc tcttactggt    43020
cttcacccca tggcccctag agactatgtg cctaccaact aggaacagca gatgcttcac    43080
actgtggtcc agggactgga actgtggcca aagagacagc ccttaaagac aagggacact    43140
ggatagcacc catggccact gagagaaggg tctgaaagtg tgtctcctgg gtgacactgg    43200
ctgctggcac ccccaagcca ggctctagct caagcgtcca atttcttaga gccgctcagt    43260
agtttctgtg atctcagccc acactgtggc caatgggctt ctcatctctc tgctgaggat    43320
cacaacccca ggacctcgag cagttgaatg accaggctgg cttcacatat gcatgggtgt    43380
agatttgcat gtgtgtagaa gtagcatggc tggccttggc cacccacca tgacctcacc     43440 tgggtccctg ttaaactaac tccttagaca ttttgcccaa gcccacagcc tccacgaggc    43500
cctggcgtgt ccaccatctc caaacctgtc atggtccacc aggagcccaa tttcatctac    43560
aggccagctg tgaaatctga agttctggta agcccttgg gtcccctcca ggttgtctct     43620
agaggagcag accagggcta cctcccctgg gctctgctgt ctctggaggg caagtgaggt    43680
gggacaaaaa tgcagatcac agatgccatc tcttaacctt cttattggcc aagagatgag    43740
gccacatggg tgtaagtgga tgttgacatg accagtggaa tttctgttcc ccacttgact    43800
gaacagcctg gagctctgtc taaaagtaat aatgatcgct acgacctgtg aagagcctac    43860
tatataccag gctctgcatg gcctcaatta atcttcacag caggactgtg agatggttcc    43920
tgtggtcatc ctgtttaaca ctcgaggaaa gggaggttta gagaggttac cagaggggca    43980
ccaggttccc caggcagagc ctggacttaa tacttaccct catgcctttc atactccaaa    44040
```

```
gcccacgctg ttaccctcgt tgccatcttg ccaaaaccta cagagattcc aggtgccctg    44100 gccctgccc  taaggcctgt tgtggcctgg catgaaacac cctcagatgg gaaactggcc    44160
agagcaggtt cactcccttt ctccaactta cttctcacct ctcactgtga ctggaagtct    44220
gaggtgtggt cctggggaag tgagaaatgt ccgccagtct cagttactga cggctaaggg    44280
agctgggatt cgtgtgcacc tcccagaggt gccgaccact ggctggcctc ccatgcacag    44340
tgagaagaca gtcatgtcag aattttaact tcccttttcaa ggaaactcta tccaaatgtc   44400
agggcaggac agctgagata tttattttgg gccttaactg tcccgtcagc tccccagaga    44460
gcaaagtttt tgctcctggg acagcctgcg gatgcatcca tgtcatgttc tctggctaat    44520 atcaagggt  ggtgtctgct tgacaacaac tgggtagcat ctttgggcat tgagcaggcc    44580
tttaacgtaa gccagactgc tcggggaggg acattggcac ggcagcccca gactggcagg    44640
cccgaagcct ggcaccaggg ggcagccaag acctattggt aacatccaat gtggaacttt    44700 ttttttttc  ctctggcagc cacaggagat gttgaagagg atggtggttt atcagacagc    44760
attcagacaa gtaaactgat acccattgtg tgtctggagt ctcccccacc accccgtcc    44820 ctcccactct gtgccacttc tttctctctg ggagtacctg gtcaggtcca tggtggcccc    44880
atctgccacc aagcctcagg ccagagctgt gtcctccatt gcctgcgcag gggtggggga   44940
ggatatcata tcagatgggg acccagggct tattagaccc catgcatgag ctgagaaaca    45000
gcagtatccc tgggaactca cctcttctgc tgctgtttgt ccagagagga gcagggcaga    45060
aggaaccctc agaggcccac agaggccaag atgggccctc gctccagccc taggagagag    45120
ggaaggggct gcttaggtgt ctccctgtac cttcccctct tcttctccgg gcagatcaca    45180
gcttcaccaa ccctgcctga cactgaacca gcgtcaggga ggaggtggtg gctgaggtcc    45240
tccctgtgcc tagggcactc ctgtgcacag ggacgtggaa gtccttgctg gtcctctgag    45300
tggcatcagg caggcagcca cctacctccc tgcctcctgg ggtacctcca tggagccaac    45360
cattggattg gctgtttcat caccaatgaa agaaaccca  ggacagagag agatcttgca    45420
gccagcccag gcttctccag cctcctcact gataacccac caacagacca caagctgatt    45480
tgactacagg cagggagcag aggggcagta tcaactgtgc agtgagacat aggtgttggc    45540
aaaagaggct gctcccagcc caaggatttg tcaatttaat ctttccagca accctgggtg    45600
gtaagtgcta ttatcatacc cattttatct atgagaaact gaggcagaga gatttgaaaa    45660
tgtgcccacg atggcacagc taatgtcaat ccctggattt gaatccagga ggtcggtctc    45720
tgcagcctgt gctcttaaac actgcaccat cctgccttaa agcactgtcg tcacacaaga    45780
ggccttccag gacctggcgg tttagggcac aaacagccct cacagggaga gaagcaggga    45840
agtgcagagt ctaggctcca gaggtggagt caaacccttg ctcccctgcc cactgactgg    45900
gtgaccttgg gcgtgaatat cacctctctg ggcctcagtt tcttcctctg ttgaatgagg    45960
ggttgggctg cctcttttaag ggccaaccag ctgcagtggc ttatgagtct ctgatctaaa   46020
ttcacacaaa acacaagtac ctgccatctg gcccatccct gagagctggt tctcaggatc    46080
atggagcaag gaggccagag ccagcactgc ccagccttcc aggagaaaca gccggagtag    46140 gcagggccc  caaagtcaaa gagcatcgac tccacatcct gcccaatgat ccttcttgcc    46200
tgtgcattca ctgcaccccc tcctctgtct gctgcccaca cactgacctg gatgtagctc    46260
ccaagctgag ccgagctcat ggcctcttgg ggttgagcct gggtgattga ggcaagtgag    46320
gagggatgcc aggcagatgc ttggggatct gtctgctgat atttggtgct catcttgtgc    46380
ccggaaccta gttggtgcat tctgaggata ggggaatctg tagcctcccc accacacaga    46440
```

```
ccatgggccc catgggtcac ttggtgtggt ctagggacct gcatgctgtg ggtggctcca   46500
ctcagtctgg cgaggcctgc cacggggctc tcctctgctc ccaccttcca tggggaccag   46560
ccgtggctct gctgcccttg tgcttagcat cctggcccct cagcctgggg atgcccctgg   46620
ctcccactca ctgtgtgtga ctcccgagga aggccacata gttcagggac tacctcactg   46680
tgtgttcagg tgccacctca ctgtcttgtt tctacaccct ggagccattg tccccacagc   46740
atcccccatc aagccaggtc ccctgagctg tgtgtcctcc cttctcccct agctaaaggg   46800
ccaacctgcg ctccgcagaa tctggggagg cctcttacct tctaggtaag cattacatga   46860
ggacactgcc aggctccagg ccaacactgc ttctcaacac cacctgcttt cttcttgttg   46920
tccgtgggct ccctccacca tcttgtggct gatttccagg aacagccttc tcttgagctg   46980
gatgggcccc tcctgtgggg tcagagcact gggtggagac accttgggct tcatccccca   47040
gggcctgggc ctgctccagt ggagacttgg aagagatgag gtgggcccta aaggacttga   47100
ggctggggct gagactttca gcaaggcaga tgccgcctct ccagaccatc tagacgtcac   47160
tggtgcccct gcagcccctg acgcttgtgc cgctgaagca gggcagggtc aagatcctct   47220
aaagtcttcc tcagcctcct gcttgtccct gaacaggggt gccctggctg ctagggctgc   47280
cggcctcctg tctgcatccc gtaccctggc cgtgccttct cccgccctac ccctcacttc   47340
tgacccttgg attccgacca ttcatcccc tactcctcgg ctctgaccct caagaccctc    47400
tgctgtgttg ccctaaagcc ctccctttgc ttccaggatt tccggaaata tgaggaaggc   47460
tttgacccct actctatggt aagagatgac gcttctctcc tggacaagta acccaggaa    47520 cagggcagtg tgggggttag agggtttgat agtggtgcat tctgggcctt ggggtcctgg   47580
gatgaggtgg ggcacagagg agccccagtg atgccccagc tgctcttccc acgaagattc   47640
cttccaaagg gcactccagt gtgaactgta tggtgcacat gcacgtgtgt gtgtccactg   47700
tccccatggg gcctgggacc cccagttgaa gaccagtagg ggtggggctg ggcacggtcc   47760
ccttgcccat gtgctctgtg gggcccagtg tcccataggt gcctggattc cccttccagc   47820
cctaccccaa gcgccatcct tcaggccagc tcaaagcttc ccactgtctt tttctctcta   47880 gttcaccca gagcagatca tggggaagga tgtccggctc ctacgcatca agaaggtacc    47940
tgggcatgtg gaggccggtg ggccgccatc cctctctgtg cctgcccctc ctcccttggt   48000
ctcctgcctc tactctcaag gtcactcctg ggtggtctct caggtcccca ctgtcctccc   48060
ctctcccacg gagacgcccc tctgttgtag ggccgcatac ccaggcccca cttggcacca   48120
aggctgcgtt ttctccagat ggcactgccg gtgaccccat ggcttcttcc actcttactg   48180
tggctctgtc aagagactcc ttggtgccca ggtgtccaca ggctgctgtc tgcttggctc   48240
cctaaggcct gttttcctct aaccaggagg gatccttaga cctggccctg gaaggcggtg   48300
tggactcccc cattgggaag gtggtcgttt ctgctgtgta tgagcgggga gctgctgagc   48360
ggcatggtga gtggagacta gccacaccca ggtttgggga tgatacagtg gttagacggg   48420
gccctcccgg aaagcaaaca ggtgaccact tggagtgggc tgacggttgc tggagaatgc   48480
cctcccactc gggtccatcc atccgactgc ctgtccaatc cctgggggca tgggatggcg   48540
ccgggacctg tgagtacaca gccaagccag atgccaccgt gccctcaggg ggtccccagc   48600
cagggtggga gacggactca gaattgccag atactgaaag tcacagcatg gtctgctaag   48660
ggctgacggg gaactcagag tggagggaag ccatgggaac cctgaggggc tctaacccca   48720
ccaagaggag atgggaggcc aggagtgctc ctcagagggg cgaaccctga gctgagcata   48780
```

```
gtcaatgtca gcctcgcgaa ggggagaaag ggctttcgag gaagaggagc agcacgtgga    48840
aacccccgaa accttgcctg tcctttcagt gatggtagga gccgaacgtt tggccagaac    48900
tagccatgtg ccagaagcta ttcatctggt ttgcagccct gtgtctgagc gtttcatgga    48960
tattaactca cttaatcctc acaacaaccc tgaaagcagg ttctgttatt attcttattt    49020
tacagctgag gaaactgagg ctcagagagg ttaaagtatt tgttcaagga cccacagcca    49080
ggagaaggtg gaggcaggac ttgaatccag gcagtttggt cattttgctt tactgtccgg    49140
cacaagtgcc acctctgtct gaggtcttct gcagccttgt cccttccag agggccagag     49200 gcccccatac cctgtgtctc tcttctcatt ttgccttgtt ctttatcccc ttatctacaa    49260
aaacaccctc tgctgatgag tgaaaccttt gcagacccca ggcacagtct cttgcttcaa    49320
accatcaccc cgttcacctg tcggacagtg tctgaaaccc caccattggt gatttcttct    49380
tccatgtcaa ggaagctcct gagtcctttg tggccctttg tggagatgta ggtgcccttg    49440
gaggaggagc cccaggcctc ttaccttccc aggccagagt gggggaccct atgagcagat    49500
cccttccagg cagtcctagg ctggagccag gctgtaccat aagctggagg tggtagaatg    49560
gaggtggtaa gaggtaaggg gcaggaaaca gggatgggaa aggcccttgg gggctggcaa    49620
ccagacctct gtgggttact aaggtgaggt atgggcattg ggagccctgg atacaagtcc    49680
agctctgcac ccatgacctt ggtgacttca cactttaagc tttcatttca gccatagaag    49740
ggggacctgc ccagctgggc agctgcccca gcccatcagt gcccaccag gccccacctt      49800 cttcttctgt cttcatttct ctgtcacctg gtgacacttc tgtgatacct gcctgctgtg    49860
tctagcagag agaggggacc aggatggatg ggtgactctc ctgggtcctt cccacttaca    49920
aagccccaac ccaaccactg ccttattgcc cctgagactc tgtcatggat ttgtacaaaa    49980
tgaaaaggtg aaagtcaccc atccccagtt gcactgcaca gaggcaactg ctttctgtgg    50040
tttggtcctg cactgctttg aacataacta gtcactgatg aagcttccct aggagcacgt    50100
gtgttttaag ccaccatggc caccattgtc agtatcatac accacattcc tatgggcctt    50160
catgccacaa ggctcctggg tgatctattt caatgtaacc tggagagtgt tctgtggaca    50220
tcaggactgg gagaaattcc tccaaaaagg gctctgatgt caaagaggtg tggaaaacca    50280
cgcacaatct gtctacctct tggaaagctg cagtgcatgt tagcacattc aagactgaca    50340
aatcctgcag tgagtagctc tgttcagctt ataactcagc tttccccaaa attattagat    50400
cccaggcaac tctttcagga gcaccttatt acagcttcat ttattcaaca aatatctact    50460
gaggtcctat tttgtgtcag gcattatgtt aagtgctggg gatattatgg tgaaccaaaa    50520
agacaatccc tgcccacgtg gagctgacag tgtggtggga gagaccatca gtaaacaaac    50580
agattaatga ttacgaattg tggaaaatgc caaataagaa aagattggga tgctgtgaga    50640
gaataggcaa gatctacatt cgactgagcg ggggtcagag aagccccttc tgacatttcc    50700
tctcagacct agaagaagag aaagcaaggt agggaacagc gacatgaagc ctctgaggca    50760
ggagagagca tggcagctca gggacctgaa cagaccagca tgactggcaa cagggagggc    50820
cggctggcag aattgactca ggcctcatac tgtgctggaa atgcaggtct gtgtccctct    50880
gtaataacag aggctcatca tcaatgatat ccaggttctc ctgagctggg gtgagggggt    50940
gtggaaggga cagggactaa atgcccttg actagccact aaccaggtgg ctagtttccc      51000
ctcatgcttt ctgagtccac atgagctttc agaacccagg ctcaggtctc ttctgctgtc    51060
tggcaatgac ccccctttgc caagccctgg gccaggcacg tgtcacatac agcccagttg    51120
gccaatcagc ctcatctgcc tgcaggtggc attgtgaaag gggacgagat catggcaatc    51180
```

```
aacggcaaga ttgtgacaga ctacaccctg gctgaggctg aggctgccct gcagaaggcc    51240
tggaatcagg gcggggtaag aataaggccc ctccctcctt tcctccctca cctgcctgcc    51300
tcaaaccctg gcctctgcag ccaggtctca caataggatg cctcattcca gggtgggcat    51360
ctggagtcca ggcaacactt tggtgacacc ataccccatc cagcctgtgg tttaaatctg    51420
acaagatggg attcagaaaa atagatgtca attcctgacc ttggatccaa aaagccagtg    51480
gcttaaacag actcttgaag ccagggcatg gcaggtcacc caagaaaaag acttaaggtc    51540
ttttctaagt gcacactgaa caagaatcaa gagaattctg ggggctacca gaaagcatta    51600
acaaaagcag agaacccagg atgaaggagg gctggtggg  aatctgctct gcactcatta    51660
gacacccacc tggatcacgg ccactgcata agattgccca ggctgtgcac tacataatct    51720
gaggggggtgc ccttttacag actgtagtgt gaatggtgcc tgctcatggt gtgcaatgca   51780
caacctgtgc aactgtatgc aggcagccga gcctgaggta ttaagttcag tgccgaggaa    51840
gctgaccaga tgggcctggg acccacatga agggatgtgg agaagagaag actcacgggt    51900
aacatgatga ctatctttga ttatctgaag gtctgcatta gggcagaggg agcagaagtg    51960
ttctctctga ttcttgaggg aagacctgga ttggatggag ggaagtcctg gggaaagaga    52020
gagagatttc agctcaatat taggaaccag ctcatggtag aggggcccag tgatatttcc    52080
aatacttttc aggggataca cctaagccaa ggagggagaa tgaggggcaa gtcaaggatg    52140
gcagtaaaag ggattcaggt gttaggatca aaaagctggg ccagaagtcc cccacttgat    52200
tgtgcatcag aaagtgcgtc ggaattaccc agagaggttg ttaaaagtac tatttcccag    52260
gactcaccct tgacttctgg gggccaagtc tacgagccta cacttttaag aagttccccc    52320
aagtgattct gaggttgctg cctgtccccg gtccatagat tgacatttgg gagctgagtg    52380
tcattcaagg gccttgcagc cctgtcctct atggtcccga agcctcagag actagaaacg    52440
tcctcagacc atggaagtca cagtgggccc caggtgggcc cgtggaaga  aggtgcagcc    52500
tggctgatcc taggccatgg ggcccagaaa tggggatgga gtgccggggc agatgcacca    52560
tccaactgag tgtgccccag agtcacacgg cttctcccca caggactgga tcgaccttgt    52620
ggttgccgtc tgccccccaa aggagtatga cgatgagctg taagtgtgtg caagcaccta    52680
gcctgagacc tcttcttcct tctccagaat ctcagccacc tttctccagc ccatccccag    52740
ccttctccca gcctgaagga atggcccaag cacgcagctt tcatagcca  gagctcctag    52800
aaaactcctg gactagagcc aagtcattgt ccttaagcag tgtctgagct gcctcccggg    52860
cagtcttgtc caaattcttc tctactatgg ggaattgagg catgaggtct tagaccgggt    52920
aagcagagac gttgggaaaa agactcagga ttgttaattc cccactcaga actttatccc    52980
ctgccccatt attagatggt tagaaggtgt ctgtgtccat ccttcactct ctggaaggtc    53040
ttcctgatgt ctaactgcat tcactcatac tgtgcctcta ggcagccggg accacaggct    53100
tttgtccccca cgctgtggga tctccaggga gctttggcct agactgtctc tctctgtgat   53160
tccctgtgtg tctgtctctt gtgtcctgtg ggtctctctg tcttctctcc tcctccctct    53220
ctgtctttct ttcaccctt  ccttcctt cc tgtcaacatc ttatctgccc cctccttcc    53280
ccttcatccc ggtcccctt  ctctctcact gtctcctatt ctttcttcct gtttctcttc    53340
atccctgtct ctgagtccct gttcctctgt ccttgtcatt ctgcatccat tcttacctct    53400
ttgtctgcct ttctctgttt ctctgcctct gtgtggtgtc tcacctccat cctcacctca    53460
tcccatcacc tccccagccc tcacccaccc accactcacc cactcactga ccatgccctg    53520
```

```
cctccctgtc gtggctgggc ctgcttgctc cccgtgccca gcagaatctg agctctacac   53580
atgtcttgga gaaaccaggg tctcgcagct cctaattctg gaacccaggg gctaggcaga   53640
acccgaggca ggagcccagt gaaaggagaa gccccatgga gctctgcctg ggagtaacca   53700
agcctgtttt gtgtttcttg ctctgctctg tatatataga gcttctcttc cctcctccgt   53760
agctgaaagc ccccaaccgg tccgaaagct ccttgaagac cgtgctgccg tgcacagaca   53820
cgggttcctc ctgcagctgg agcccacggt gaataggcag gcgggccaca gggcctgtg    53880 tgtccctgct gcttgcagtg gccatctgct gcccacgctg tcagcaggtt ctttggactg   53940
gcgtctggag ggtacacaag gcgccatccc tgaagtgctg cctggggcct gctgttggcc   54000
acagtggaat tcctcagact caaagccctc ccctcaggga agtggtgcaa agcccagtct   54060
gtagtacttg cttgggaccc aggtgtcctg actcatcacg gccctgggac ctgctttggg   54120
tcccaagcag cacccaaatg agcaggatga agccctgggc aacattctct gagggacaca   54180
gacaatgcct cgaaccaggc atgtggggct gaaggagccc acaggaagcc tggctggaat   54240
tgcccccaag agatgtcctc aacagaatgt gaaaattccc cttcctgtga atgccaacct   54300
cctgggagct cttgctccac catggccccc acacttggcc agaaccaggg ctattaagag   54360
gttttgaagg ctggtccaaa gaaccagggt tggtggatta gagttgctca tgtcctgttg   54420
tgccctgtca tggcctgagc cgtgcttaga ccaaacggtc ttctctgcct tctcccttcc   54480
ttggctctgg gctctatctg tgggatatac cgtggaaccc agctgtagga tgtgtttctc   54540
accctgtgat agggatgtgc ccgtggacag agctggcagg tggctgtgaa actggtgttt   54600
ggtgtggcct gaagccacag atggcagcat ctggggcaga cccaagcctg gacttgactt   54660
ttctgttaca actttcccaa aacattaggg cctcatgctc ccaagacact tggccgggta   54720
gaccatggct tctggggtgg cctgcatggc cctatgtttt ctgttacttg ccttttgcaa   54780
aggactcttg cccctgttcc tcccagtctc ctccttcccc catcccaggt gtccctcccg   54840 cttctccct ggcctcctgt gtgctgtggc tgtggctggt gtgtagccac ttggggcctg    54900
cacccagagg ggtctccaaa gggtggcagg gccttgtgct gccagagtgg gtactccccc   54960
ttgtggggcc ttgctctggc tgggctgagt gtgcacccac aaagcctgta tccacctggg   55020
ctgtttccac ttccctgcag gaccttcttc tgaagtccaa aaggggaaac caaattcacc   55080
gttaggaaac agtgagctcc ggccccacct cgtgaacaca aagcctcgga tcagccttga   55140
gagaggccac actacacaca ccagatggca tccttgggac ctgaatctat cacccaggaa   55200
tctcaaactc cctttggccc tgaaccaggg ccagataagg aacagctcgg gccactcttc   55260
tgaaggccaa cgtggaggaa agggagcagc cagccatttg ggagaagatc tcaaggatcc   55320
agactctcat tcctttcctc tggcccagtg aatttggtct ctcccagctc tggggggactc  55380 cttccttgaa ccctaataag accccactgg agtctctctc tctccatccc tctcctctgc   55440
cctctgctct aattgctgcc aggattgtca ctccaaacct tactctgagc tcattaataa   55500
aatagattta ttttccagct tataggagtg agtgtggatt tgggcagcag attcaaggct   55560
gcaaatcaaa aaaccataag gtttgtggcc cctattcaag ggtgatagac agatcccagt   55620
gctgtgatct gggtctgaca tgaagggtgt gatcaaatgg ccaggctggg cttggagcag   55680
aggttgagaa agcaggagat gggctgggct gggcttcaat gtcttctcag cagagatggt   55740
aggagatgaa gtctgtgtgg cagggatttt gctcaattcc agaaagcaga gctgaaggca   55800 ggagcccga agggtcacct catgatatgg ggtgcccagc ttctttcaag aacgacacag   55860
ccaccaatgc ttctcctgag gtcaccacga cagcatgtga gggaggaaga tggcagggtc   55920
```

```
cactccctcc gtggaagcac atcccacaga agctcatggg aaatgcaagg gcttgaggca    55980
ggaaggcata actccggggg cccagcaggg ggaatgtcac agttcttctg gtgacaggga    56040
ccagggctgc tagctctgag gaagagggtg gggctgtatc agcacgactc gcctgacccc    56100
gtctctgttt ccccattcca aattcctgtg gtacaatctg atcaggccaa atcacctgag    56160
cgggcgaccc ttgggttagg gaccagtcac aggtccaatc agctgtggcc gggggtgggg    56220
tcacatccca cccaacatgg ctgctgaggc agcaaggacc gtgggcagca agtcatgatc    56280 accacccta ccagaggatg actatgacat ctctcctccc ccaccaaacc ctgggtatgg    56340
aaaggaagtg gactggggtc ccaagggaag gcagtcttag ggagagtgcc tctgtgtgag    56400
gggaccacag gaaaacccct tcctgaggtg ggacactgca gagagcccct cggggacaca    56460
cccactgccc atcccccagg ttcagcccta tgttcagctg aatccccac ttcatcccac    56520 agtggatgca gactaagctg gatcccgaga acttggtaat aaaacagaca ggctctcaac    56580
acctcccaga atcatggcag gggagagggg ctcagaccaa aatgcagcga ctaccatgtg    56640
ggactgaaag aaatcaatgg gtggggacag agagagggag cagagaaact gccaaacttt    56700
ctgatgtcct cgatgaagac aaagccacag tgaccttcaa attactgcg ctcagagaca    56760 gcagccacac agacgagctc cctgtgtttt cctgtcaggc acctaacctg gttctggaga    56820
aaattccaaa acccaggtaa gaggagggag ctcctatttg ctgtcaccca tgtgcctggc    56880
ctaggctaga cccttgtctg ctgtttcaaa ctgcaacacc tgggcttcat gcctggccat    56940
cccaggagcc tggtgatagc agcccacact cagatggcat tgactaagtg ccaggtattg    57000
ttctaagcac tcagctcata cattccatca acaactccat gaggcaggta gtattattat    57060
caacaacctc attttattaa gagacagttg atataaaaag aggtgaagtc acttgcccca    57120
ggtcacacgg tgaggaagta gtagagctgc gactccagcc aggcactctg gtcccagaga    57180
ctgtgcacac ccgttccac catatgctct agagggcaag gcagctccca tcggaatgtc    57240
tcaaattcca ggccgttggc agaacacttc tccccaccac tgaagaacag tgactgttct    57300
gctgttgggt agtggtcact tcctcttgtg ccctacaaaa acttctgctg aggccttcag    57360
ctagtcagtg cctggaatct caccattgga aattcacctg tagcaggagt gaatgagttt    57420
atcagccctt atccggactt ggtgagtgag acggtaaaga ggctttgagc tcctgattag    57480
aggagaaggg cagggaggat gagcactggg ccgggcagga ag                      57522
```

<210> SEQ ID NO 2
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 2
agctgatcat attctacctg gtgct                                          25

<210> SEQ ID NO 3
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 3
atattccacc tggtgcttca gtggg                                              25

<210> SEQ ID NO 4
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 4
agctgatcat attctacctg gtgct                                              25

<210> SEQ ID NO 5
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 5
acggccacgt ccatggtc                                                      18

<210> SEQ ID NO 6
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 6
cgagcacggc cacgtcca                                                      18

<210> SEQ ID NO 7
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 7
tcccacgagc acggccac                                                      18

<210> SEQ ID NO 8
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 8
aggtctccca cgagcacg                                                      18

<210> SEQ ID NO 9
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 9
gcttcaggtc tcccacga                                                      18

<210> SEQ ID NO 10
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 10
gaccagcttc aggtctcc                                                  18

<210> SEQ ID NO 11
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 11
ttgatgacca gcttcagg                                                  18

<210> SEQ ID NO 12
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 12
gttcattgat gaccagct                                                  18

<210> SEQ ID NO 13
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 13
gctgggttca ttgatgac                                                  18

<210> SEQ ID NO 14
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 14
agacggctgg gttcattg                                                  18

<210> SEQ ID NO 15
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 15
gaggcagacg gctgggtt                                                  18

```
<210> SEQ ID NO 16
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 16
aaacagaggc agacggct                                                18

<210> SEQ ID NO 17
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 17
gcatcaaaca gaggcaga                                                18

<210> SEQ ID NO 18
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 18
gaatggcatc aaacagag                                                18

<210> SEQ ID NO 19
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 19
cggccgaatg gcatcaaa                                                18

<210> SEQ ID NO 20
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 20
atcagcggcc gaatggca                                                18

<210> SEQ ID NO 21
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 21
gtgggatcag cggccgaa                                                18
```

<210> SEQ ID NO 22
<211> LENGTH: 18
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 22
cttcagtggg atcagcgg                18

<210> SEQ ID NO 23
<211> LENGTH: 18
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 23
tgcttcagtg ggatcagc                18

<210> SEQ ID NO 24
<211> LENGTH: 18
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 24
tggtgcttca gtgggatc                18

<210> SEQ ID NO 25
<211> LENGTH: 18
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 25
acctggtgct tcagtggg                18

<210> SEQ ID NO 26
<211> LENGTH: 25
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 26
atattctacc tggtgcttca gtggg                25

<210> SEQ ID NO 27
<211> LENGTH: 18
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 27
ctacctggtg cttcagtg                18

<210> SEQ ID NO 28

```
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 28
ttctacctgg tgcttcag                                                   18

<210> SEQ ID NO 29
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 29
atattctacc tggtgctt                                                   18

<210> SEQ ID NO 30
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 30
agctgatcat attctacctg gtgct                                           25

<210> SEQ ID NO 31
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 31
atcatattct acctggtg                                                   18

<210> SEQ ID NO 32
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 32
tgatcatatt ctacctgg                                                   18

<210> SEQ ID NO 33
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 33
agctgatcat attctacc                                                   18

<210> SEQ ID NO 34
<211> LENGTH: 18
```

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 34
tcagctgatc atattcta                                               18

<210> SEQ ID NO 35
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 35
gggtcagctg atcatatt                                               18

<210> SEQ ID NO 36
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 36
gggggtcagc tgatcata                                               18

<210> SEQ ID NO 37
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 37
cgccgggggg tcagctga                                               18

<210> SEQ ID NO 38
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 38
tggagcgccg gggggtca                                               18

<210> SEQ ID NO 39
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 39
gcacctggag cgccgggg                                               18

<210> SEQ ID NO 40
<211> LENGTH: 18
<212> TYPE: DNA
```

```
<213> ORGANISM: Artificial Sequence
<220> FEATURE:
<223> OTHER INFORMATION: Description of Artificial Sequence: Synthetic
      oligonucleotide

<400> SEQUENCE: 40
cctctgcacc tggagcgc                                                    18

<210> SEQ ID NO 41
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 41
ggcttcctct gcacctgg                                                    18

<210> SEQ ID NO 42
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 42
ctggtggctt cctctgca                                                    18

<210> SEQ ID NO 43
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 43
ccagcctggt ggcttcct                                                    18

<210> SEQ ID NO 44
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 44
tgcctccagc ctggtggc                                                    18

<210> SEQ ID NO 45
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 45
ccccctgcct ccagcctg                                                    18

<210> SEQ ID NO 46
<211> LENGTH: 18
<212> TYPE: DNA
<213> ORGANISM: Artificial Sequence
```

<220> FEATURE:
<223> OTHER INFORMATION: Description of Artificial Sequence: Synthetic
      oligonucleotide

<400> SEQUENCE: 46
ctccaccccc tgcctcca                                                    18

<210> SEQ ID NO 47
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 47
gatctctcca cccctgc                                                     18

<210> SEQ ID NO 48
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 48
agggtgatct ctccaccc                                                    18

<210> SEQ ID NO 49
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 49
cgcccagggt gatctctc                                                    18

<210> SEQ ID NO 50
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 50
tgccccgccc agggtgat                                                    18

<210> SEQ ID NO 51
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 51
agcactgccc cgcccagg                                                    18

<210> SEQ ID NO 52
<211> LENGTH: 15
<212> TYPE: DNA
<213> ORGANISM: Artificial Sequence
<220> FEATURE:

```
<223> OTHER INFORMATION: Description of Artificial Sequence: Synthetic
      oligonucleotide

<400> SEQUENCE: 52
atattctacc tggtg                                                    15

<210> SEQ ID NO 53
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 53
catattctac ctggt                                                    15

<210> SEQ ID NO 54
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 54
tcatattcta cctgg                                                    15

<210> SEQ ID NO 55
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 55
atcatattct acctg                                                    15

<210> SEQ ID NO 56
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 56
gatcatattc tacct                                                    15

<210> SEQ ID NO 57
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 57
tgatcatatt ctacc                                                    15

<210> SEQ ID NO 58
<211> LENGTH: 15
<212> TYPE: DNA
<213> ORGANISM: Artificial Sequence
<220> FEATURE:
```

<223> OTHER INFORMATION: Description of Artificial Sequence: Synthetic
      oligonucleotide

<400> SEQUENCE: 58
ctgatcatat tctac                                                           15

<210> SEQ ID NO 59
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 59
gctgatcata ttcta                                                           15

<210> SEQ ID NO 60
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 60
agctgatcat attct                                                           15

<210> SEQ ID NO 61
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 61
atcatattct ac                                                              12

<210> SEQ ID NO 62
<211> LENGTH: 52
<212> TYPE: DNA
<213> ORGANISM: Homo sapiens

<400> SEQUENCE: 62
cgccgggggg tcagctgatc atattcyacc tggtgcttca gtgggatcag cg                  52

<210> SEQ ID NO 63
<211> LENGTH: 71
<212> TYPE: DNA
<213> ORGANISM: Homo sapiens

<400> SEQUENCE: 63
ggccgctgat cccactgaag caccaggtgg aatatgatca gctgaccccc cggcgctcca          60
ggtgcagagg a                                                               71

<210> SEQ ID NO 64
<211> LENGTH: 57
<212> TYPE: DNA
<213> ORGANISM: Homo sapiens

<400> SEQUENCE: 64
cccactgaag caccaggtag aatatgatca gctgaccccc cggcgctcca ggtgcag             57